(12) United States Patent
Mun et al.

(10) Patent No.: US 10,840,455 B1
(45) Date of Patent: Nov. 17, 2020

(54) COMPOUND FOR ORGANIC ELECTRONIC ELEMENT, ORGANIC ELECTRONIC ELEMENT USING THE SAME, AND ELECTRONIC DEVICE THEREOF

(71) Applicant: DUK SAN NEOLUX CO., LTD., Cheonan-si, Chungcheongnam-do (KR)

(72) Inventors: Soung Yun Mun, Cheonan-si (KR); Min Ji Jo, Cheonan-si (KR); Sun Hee Lee, Cheonan-si (KR); Yong Wook Park, Cheonan-si (KR); Chi Hyun Park, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 16/563,549

(22) Filed: Sep. 6, 2019

(51) Int. Cl.
| | |
|---|---|
| *H01L 51/50* | (2006.01) |
| *H01L 51/00* | (2006.01) |
| *C09K 11/06* | (2006.01) |
| *C07D 307/91* | (2006.01) |
| *C07D 333/76* | (2006.01) |
| *C07C 211/61* | (2006.01) |
| *H01L 51/52* | (2006.01) |

(52) U.S. Cl.
CPC .......... *H01L 51/006* (2013.01); *C07C 211/61* (2013.01); *C07D 307/91* (2013.01); *C07D 333/76* (2013.01); *C09K 11/06* (2013.01); *H01L 51/0061* (2013.01); *C07C 2603/18* (2017.05); *C07C 2603/40* (2017.05); *C09K 2211/1007* (2013.01); *C09K 2211/1011* (2013.01); *C09K 2211/1014* (2013.01); *C09K 2211/1018* (2013.01); *H01L 51/0055* (2013.01); *H01L 51/0058* (2013.01); *H01L 51/0073* (2013.01); *H01L 51/0074* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5278* (2013.01)

(58) Field of Classification Search
None
See application file for complete search history.

(56) References Cited

U.S. PATENT DOCUMENTS

2009/0027311 A1 * 1/2009 Lee ............... G09G 3/3233
345/76

FOREIGN PATENT DOCUMENTS

| CN | 109336834 A | * | 2/2019 | ............ C09K 11/06 |
| KR | 2017088601 | * | 8/2017 | ............ H01L 51/50 |
| WO | WO 2019/004587 | * | 1/2019 | ............ H01L 51/50 |

* cited by examiner

*Primary Examiner* — Gregory D Clark
(74) *Attorney, Agent, or Firm* — Vorys, Sater, Seymour & Pease LLP

(57) ABSTRACT

Provided are a compound for an organic electronic element that can improve the luminous efficiency, stability and life span of the element, an organic electronic element comprising the same, and an electronic device thereof.

16 Claims, 2 Drawing Sheets ial layer and the intrinsic properties (mobility, interface characteristics, etc.) of the material are achieved, long life and high efficiency can be achieved at the same time.
COMPOUND FOR ORGANIC ELECTRONIC ELEMENT, ORGANIC ELECTRONIC ELEMENT USING THE SAME, AND ELECTRONIC DEVICE THEREOF

BACKGROUND

Technical Field

The present invention relates to compound for organic electronic element, organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

In the organic electroluminescent device, the most problematic is the lifetime and the efficiency. As the display becomes large, the efficiency and the lifetime problem must be solved. Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase.

However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time.

Further, recently, in organic electroluminescent devices, in order to solve the emission problem in the a hole transport layer, an emitting-auxiliary layer must be present between the hole transport layer and an emitting layer, and it is necessary to develop different emitting-auxiliary layers according to the respective emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value. As a result, the exciton generated in the emitting layer is transferred to the hole transport layer, resulting in charge unbalance in the emitting layer, and light is emitted at the interface of the hole transport layer.

When light is emitted at the interface of the hole transport layer, the color purity and efficiency of the organic electronic device are lowered and the life span is shortened. Therefore, it is urgently required to develop an emitting-auxiliary layer having a high T1 value and a HOMO level between the HOMO energy level of the hole transport layer and the HOMO energy level of the emitting layer.

On the other hand, it is necessary to develop a hole injection layer material having stable characteristics, that is, a high glass transition temperature, against joule heating generated when the device is driven, while delaying penetration of the metal oxide from the anode electrode (ITO), which is one of the causes of shortening the lifetime of the organic electronic device, into the organic layer. The low glass transition temperature of the hole transport layer material has a characteristic that when the device is driven, the uniformity of the surface of the thin film is lowered, which has been reported to have a great influence on the lifetime of the device. In addition, OLED devices are mainly formed by a deposition method, and it is necessary to develop a material that can withstand long time in deposition, that is, a material having high heat resistance characteristics.

That is, in order to sufficiently exhibit the excellent characteristics of the organic electronic element, a material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electronic element has not been sufficiently developed yet. Therefore, development of new materials is continuously required, and development of materials for the hole transport layer or the emitting-auxiliary layer is urgently required.

As a precedent reference, U.S. Pat. No. 8,334,058 B2 is referred to.

DETAILED DESCRIPTION OF THE INVENTION

Summary

In order to solve the problems of the background art described above, the present invention has revealed a compound having a novel structure, and that when the compound is applied to an organic electronic element, the luminous efficiency, stability and lifetime of the device are greatly improved.

Accordingly, it is an object of the present invention to provide a novel compound, an organic electronic element using the same, and an electronic device.

Technical Solution

In one aspect, the present invention provides a compound represented by Formula (1).

Formula (1)

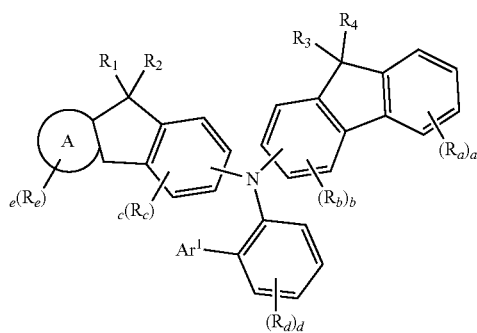

In another aspect, the present invention provides an organic electronic element using the compound represented by Formula (1) and an electronic device thereof.

Effects of the Invention

By using the compound according to the present invention, it is possible to achieve a high luminous efficiency, a low driving voltage, and a high heat resistance of the element, and can greatly improve the color purity and lifetime of the element.

DETAILED DESCRIPTION

Figure 1:
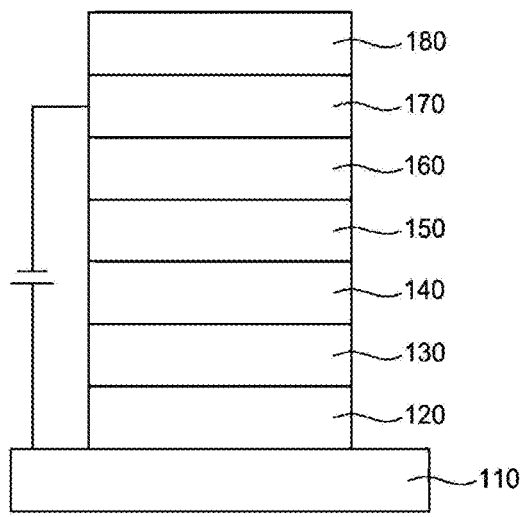
FIG. 1 to FIG. 3 illustrate an example of an organic electronic element according to the present invention.

Hereinafter, some embodiments of the present invention will be described in detail. Further, in the following description of the present invention, a detailed description of known functions and configurations incorporated herein will be omitted when it may make the subject matter of the present invention rather unclear.

[24] In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphadic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes compound below.

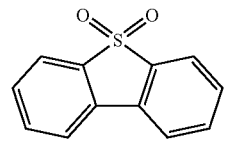

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

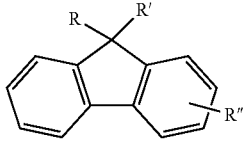

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_2$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

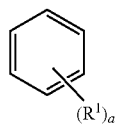

wherein, when a is an integer of zero, the substituent $R^1$ is absent, when a is an integer of 1, the sole substituent $R^1$ is linked to any one of the carbon constituting the benzene ring, when a is an integer of 2 or 3, each substituent $R^1$'s may be the same and different, when a is an integer of 4 to 6, and is linked to the benzene ring in a similar manner, whereas the indication of hydrogen bound to the carbon forming the benzene ring is omitted.

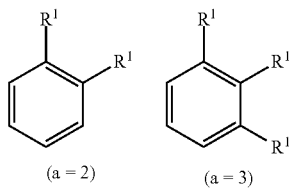

Hereinafter, a compound according to an aspect of the present invention and an organic electronic element comprising the same will be described.

According to a specific example of the present invention, there is provided a compound represented by Formula (1).

Formula (1)

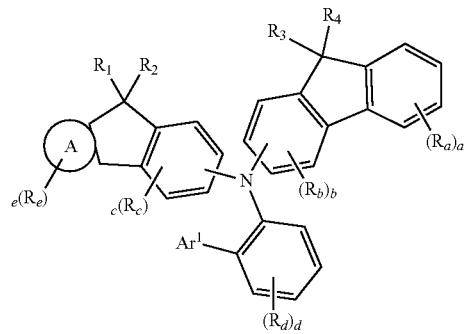

Formula (1)

{In Formula (1),
1) $R_1$ and $R_2$ are each independently an unsubstituted $C_1$-$C_{60}$ alkyl group,
2) $R_3$ and $R_4$ are each independently an $C_6$-$C_{60}$ aryl group,
3) A is $C_{10}$ aryl group.
4) $Ar^1$ is a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; or a $C_6$-$C_{60}$ aryloxy group;
5) $R_a$, $R_b$, $R_c$, $R_d$ and $R_e$ are each independently selected from the group consisting of hydrogen; deuterium; halogen; a $C_6$-$C_{60}$ aryl group; a $C_6$-$C_{60}$ arylene group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{20}$ alkynyl group; a $C_1$-$C_{60}$ alkoxyl group; and a $C_6$-$C_{60}$ aryloxy group;
6) a and d are each independently an integer of 0 to 4, b and c are an integer of 0 to 3, and e is an integer of 0 to 6,
wherein, the aryl group, arylene group, fluorenyl group, heterocyclic group, fused ring group, and aryloxy group may be substituted with one or more substituents selected from the group consisting of deuterium; halogen; silane group; siloxane group; boron group; germanium group; cyano group; nitro group; $C_1$-$C_2$ alkylthio group; $C_1$-$C_2$ alkyl group; $C_2$-$C_2$ alkenyl group; $C_2$-$C_{20}$ alkynyl group; $C_1$-$C_{20}$ alkoxyl group; $C_6$-$C_{20}$ aryl group; $C_6$-$C_{20}$ aryl group substituted with deuterium; $C_6$-$C_{20}$ arylthiophene group; a fluorenyl group; $C_2$-$C_2$ heterocyclic group; $C_3$-$C_{20}$ cycloalkyl group; $C_7$-$C_{20}$ arylalkyl group and $C_8$-$C_{20}$ arylalkenyl group}

Also, the compound represented by Formula (1) includes a compound represented by any one of the following formulas A-1 to A-3.

Formula A-1

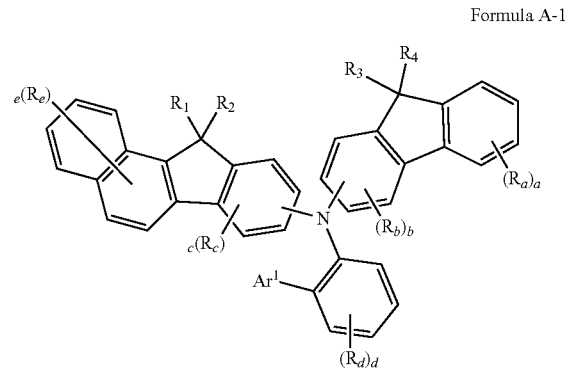

Formula A-2

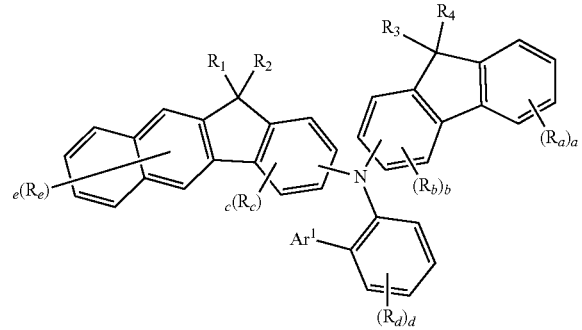

Formula A-3

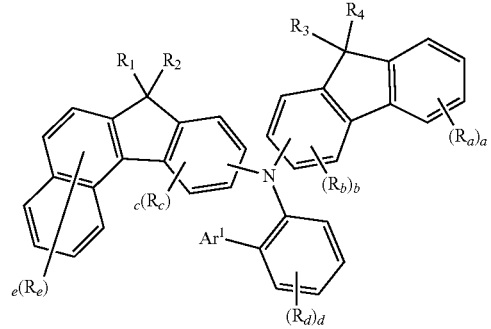

{In Formulas A-1 to A-3, $R_1$, $R_2$, $R_3$, $R_4$, $Ar^1$, $R_a$, $R_b$, $R_c$, $R_d$, $R_e$, a, b, c, d and e are the same as defined above.}

Also, the compound represented by Formula (1) includes a compound represented by any one of the following formulas B-1 to B-3.

Formula B-1

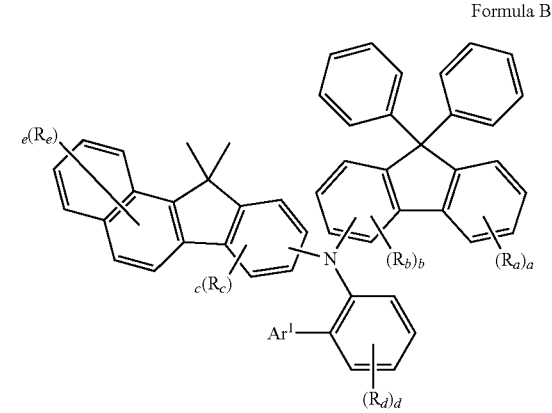

Formula B-2

Formula B-3

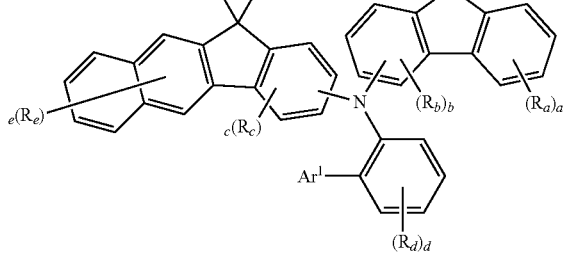

{In Formulas B-1 to B-3, $Ar^1$, $R_a$, $R_b$, $R_c$, $R_d$, $R_e$, a, b, c, d and e are the same as defined above.}

Also, the compound represented by Formula (1) includes a compound represented by Formula C.

Formula C

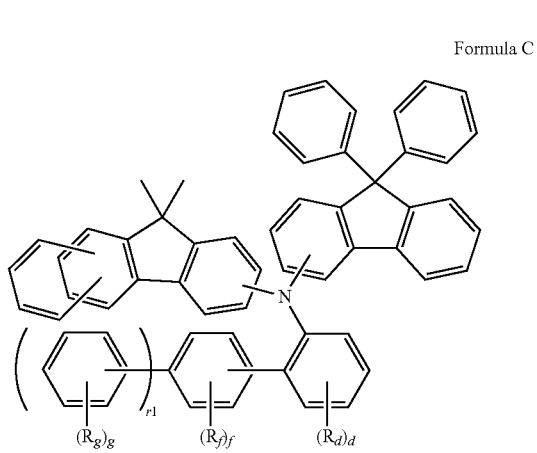

{In Formula C,
1) $R_d$ and d are the same as defined above,
2) $R_f$ and $R_g$ are each independently selected from the group consisting of hydrogen; deuterium; halogen; a $C_6$-$C_{60}$ aryl group; a $C_6$-$C_{60}$ arylene group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxyl group; and a $C_6$-$C_{60}$ aryloxy group; or plurality of $R_f$ or plurality of $R_g$ or $R_f$ and $R_g$ may be bonded to each other to form ring, 3) f is an integer of 0 to 4, g is an integer of 0 to 5, r1 is 0 or 1.}

Also, the compound represented by Formula (1) includes a compound represented by Formula D-1 or Formula D-2.

Formula D-1

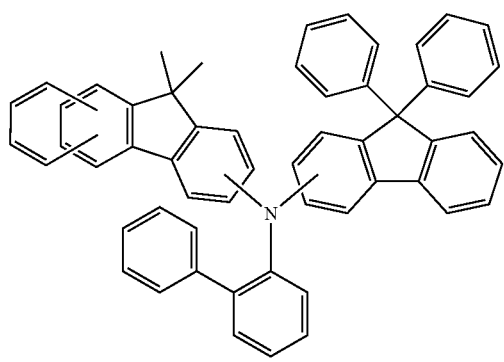

Formula D-2

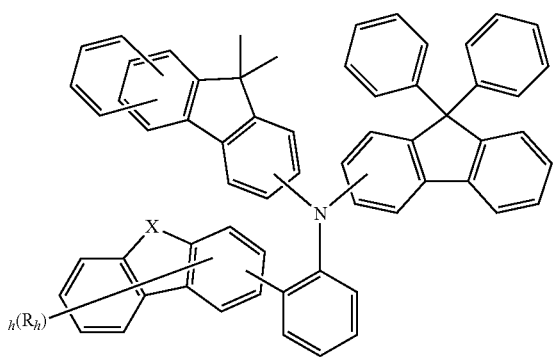
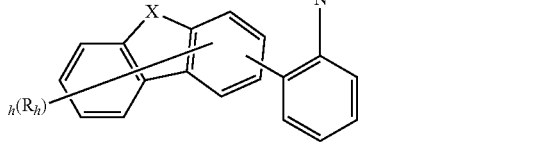

{In Formula D-1 and D-2, $R_h$ is each independently selected from the group consisting of hydrogen; deuterium; halogen; a $C_6$-$C_{60}$ aryl group; a $C_6$-$C_{60}$ arylene group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxyl group; and a $C_6$-$C_{60}$ aryloxy group; or plurality of $R_h$ may be bonded to each other to form ring, h is an integer of 0 to 7, X is CR'R", O, S or N, R' and R" are each independently selected from the group consisting of hydrogen; a $C_6$-$C_{24}$ aryl group; a fluorenyl group; a $C_6$-$C_{60}$ arylene group; a fluorenyl group; a $C_2$-$C_{24}$ heterocyclic group including at least one heteroatom of O, N, S, Si or P; a fused ring group of a $C_3$-$C_{24}$ aliphatic ring and a $C_6$-$C_{24}$ aromatic ring; a $C_1$-$C_{20}$ alkyl group; a $C_2$-$C_{20}$ alkenyl group; a $C_2$-$C_{20}$ alkynyl group; a $C_1$-$C_{20}$ alkoxyl group; and a $C_6$-$C_{30}$ aryloxy group; and R' and R" may be bonded to each other to form a spiro.

In a specific aspect of the invention, the compound represented by Formula (1) may comprise a compound represented by any of Formulas (P-1) to (P-52) below, but is not limited thereto.

P-1

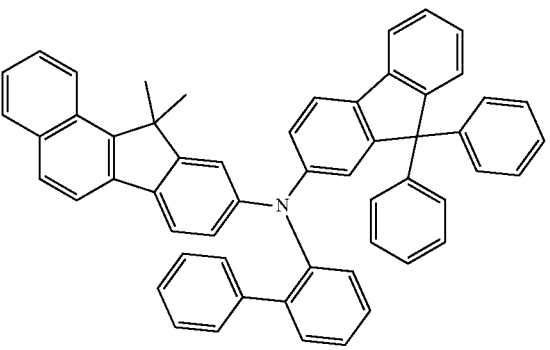

P-2

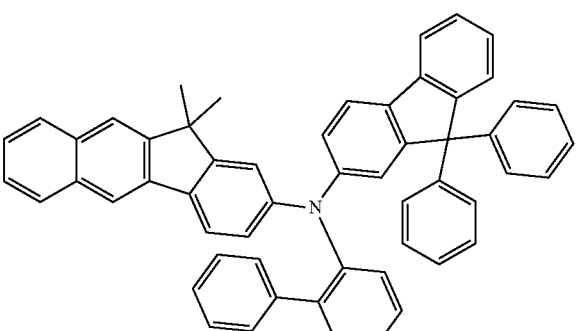

P-3

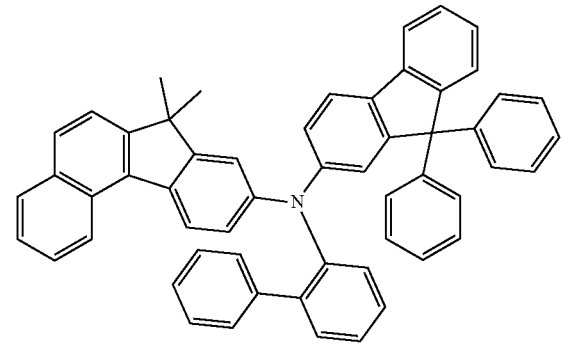

P-4

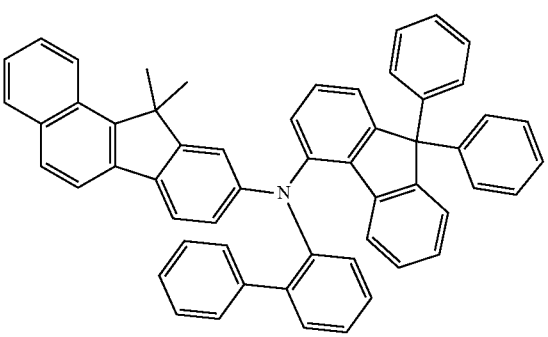

P-5
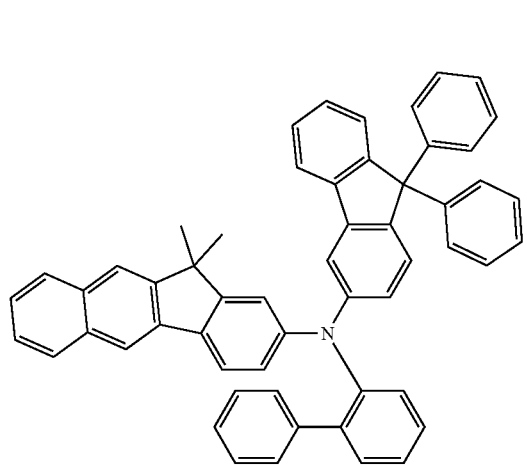
P-8
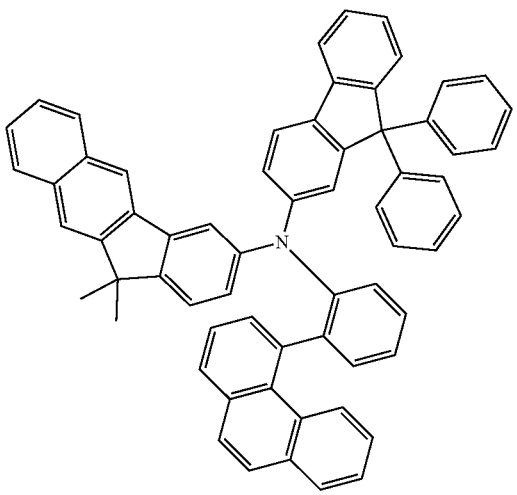
P-6
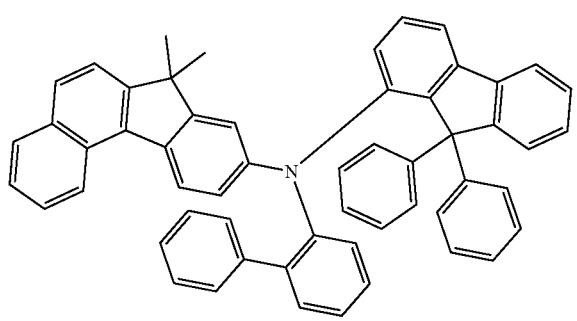
P-9
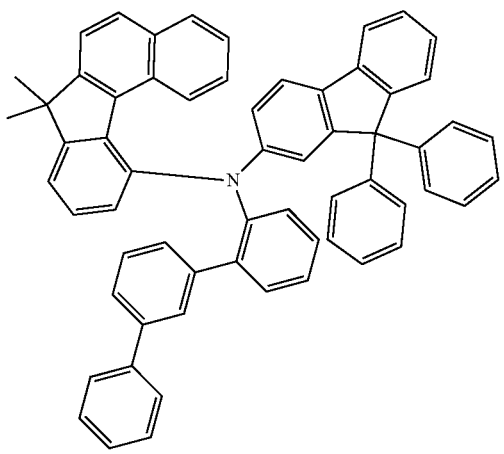
P-7
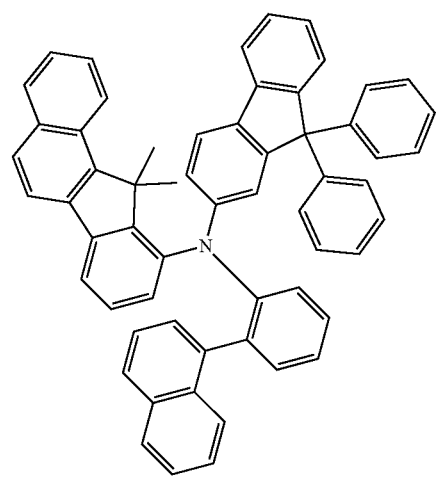
P-10
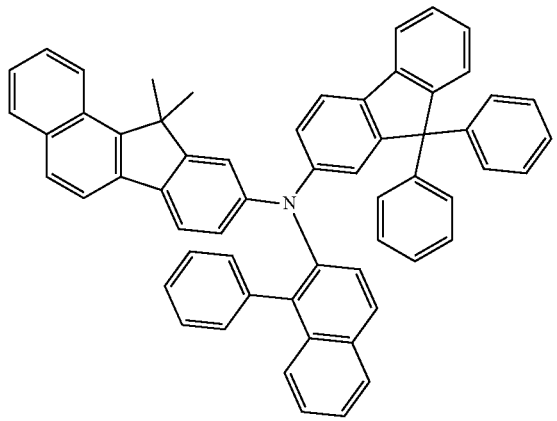

P-11
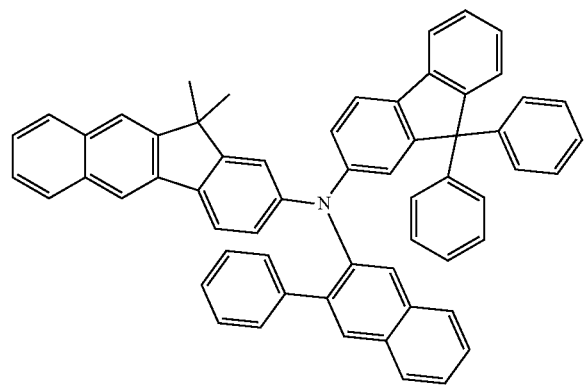
P-12
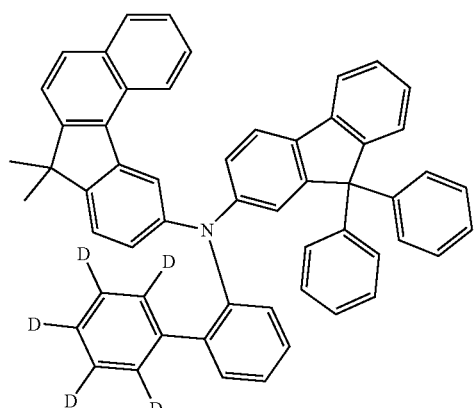
P-13
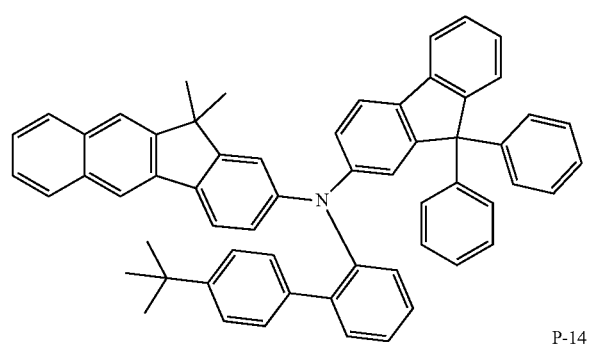
P-14
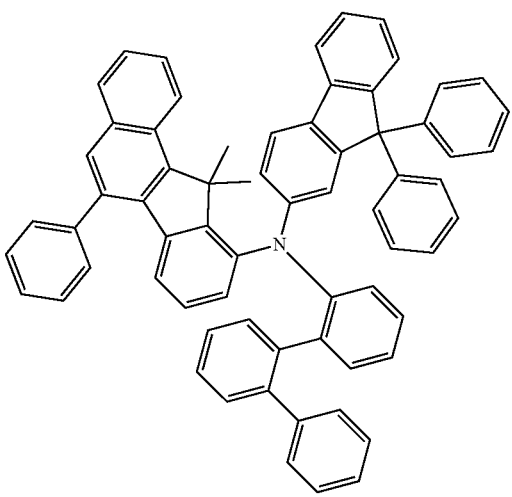
P-15
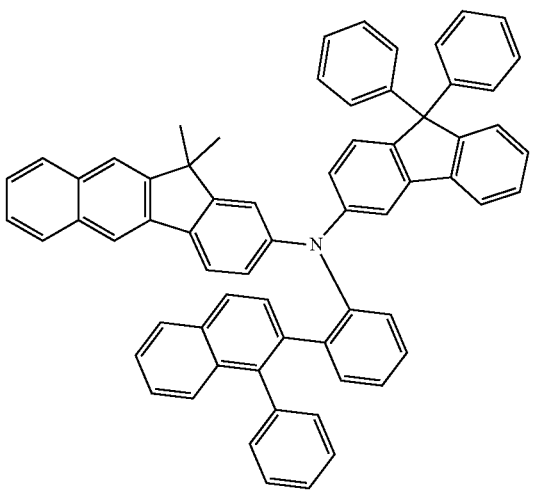
P-16
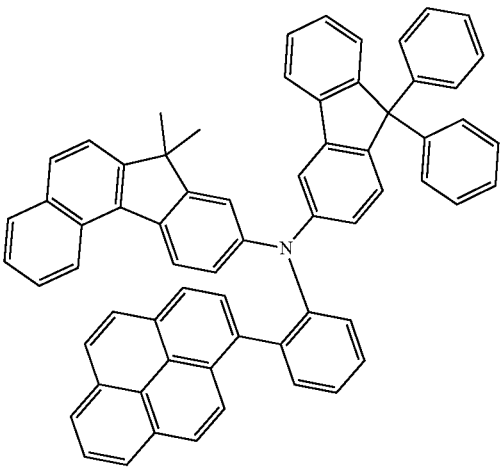
P-17
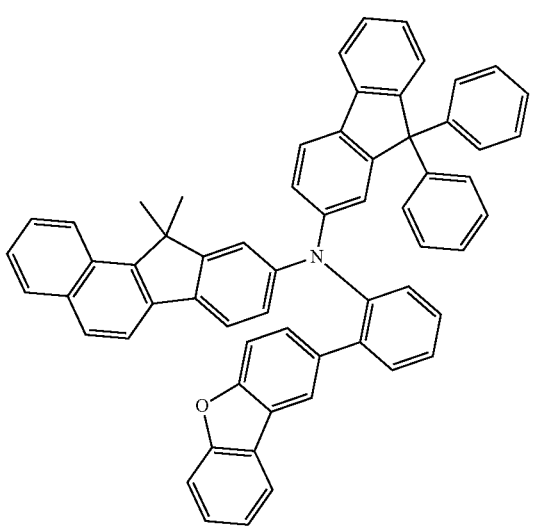

P-18
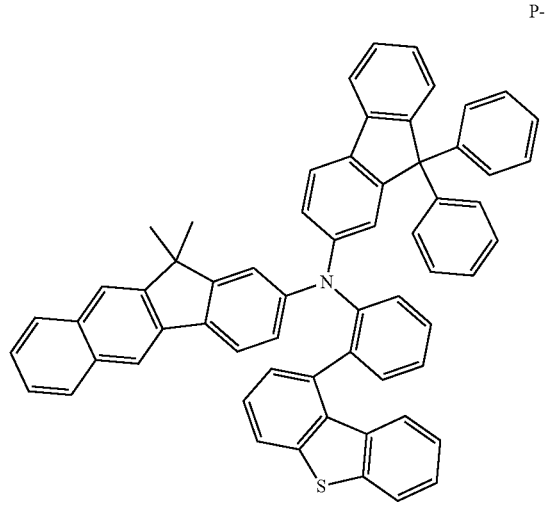
P-19
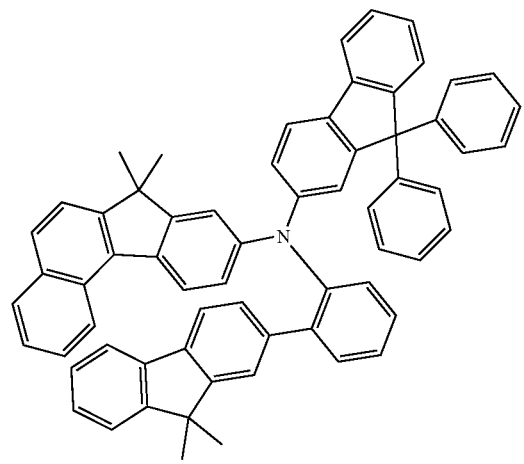
P-20
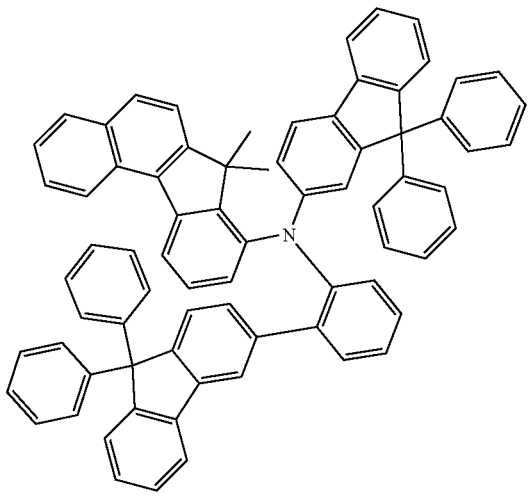
P-21
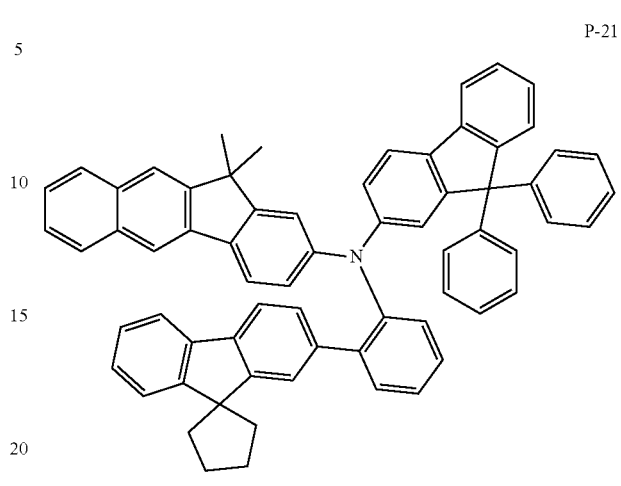
P-22
P-23
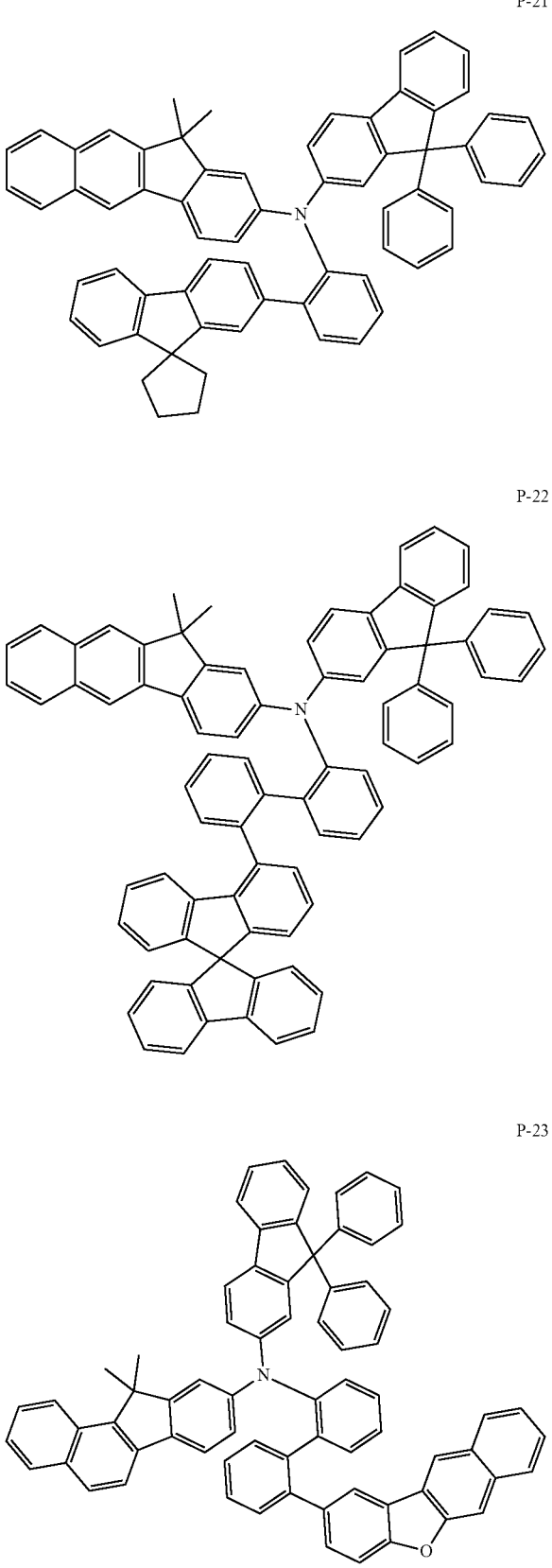

P-24
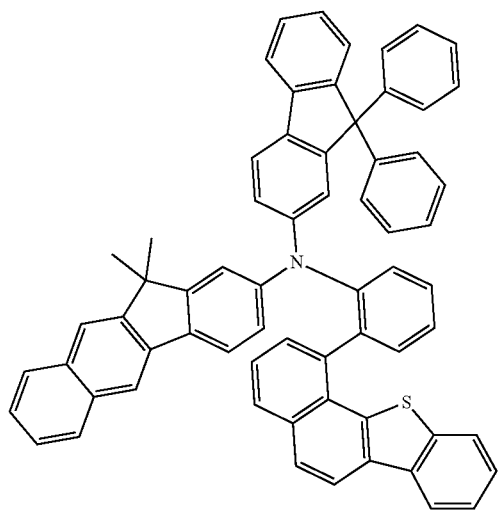
P-25
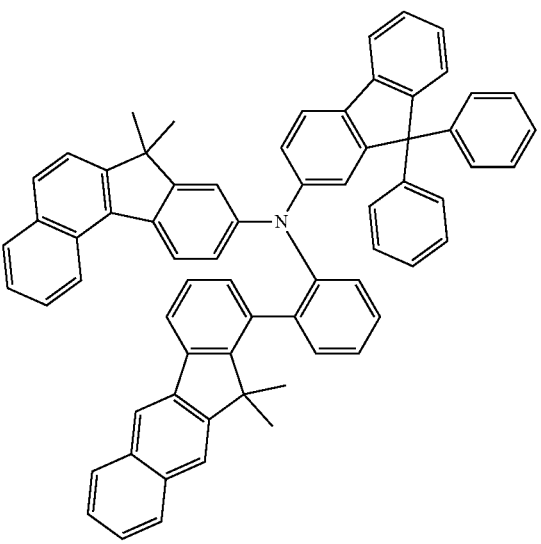
P-26
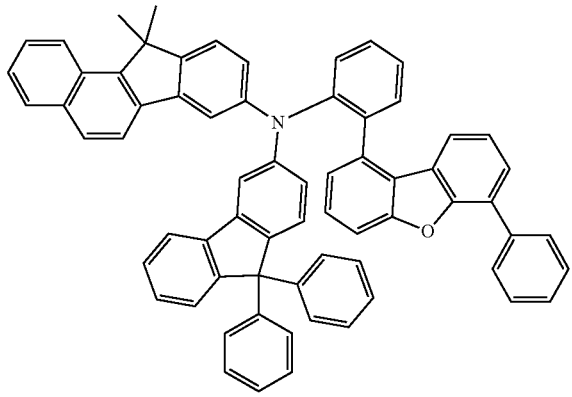
P-27
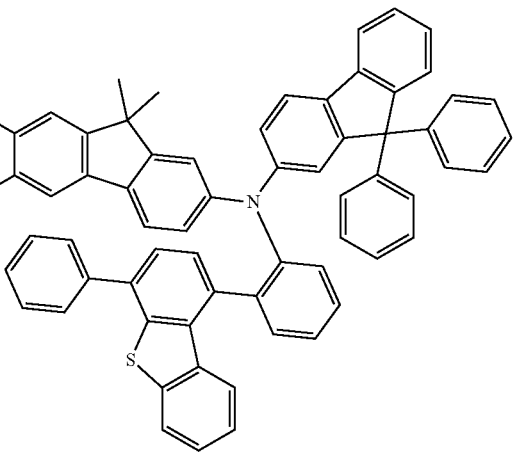
P-28
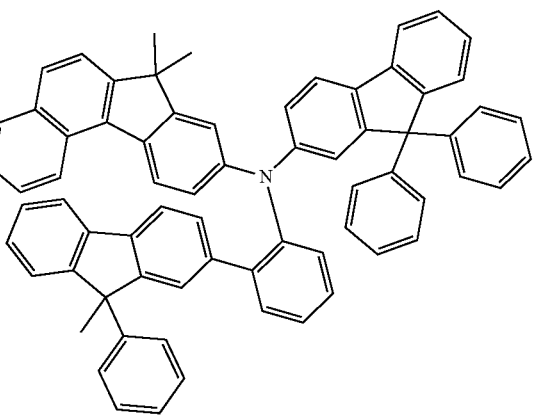
P-29
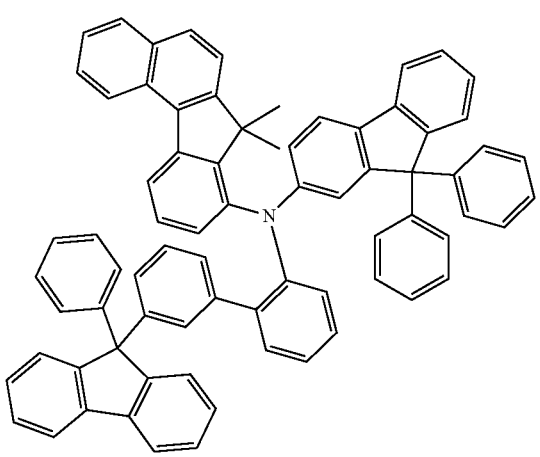

P-30
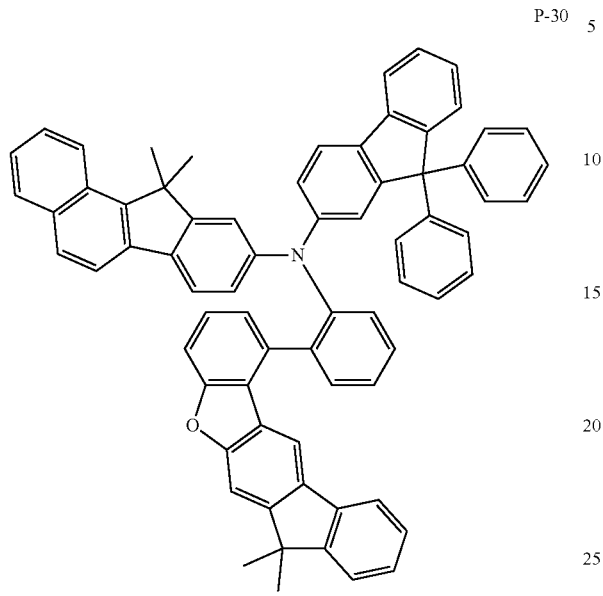
P-33
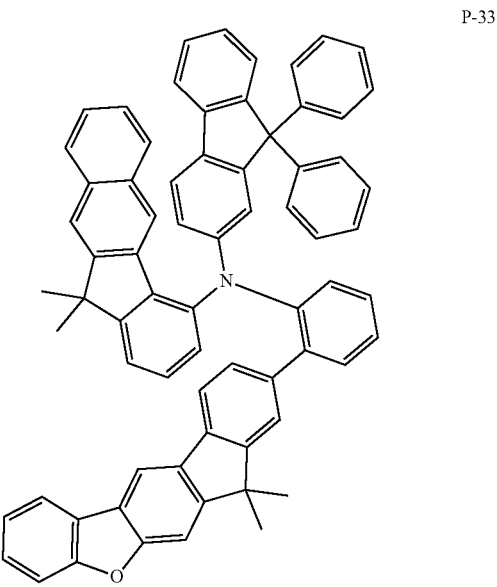
P-31
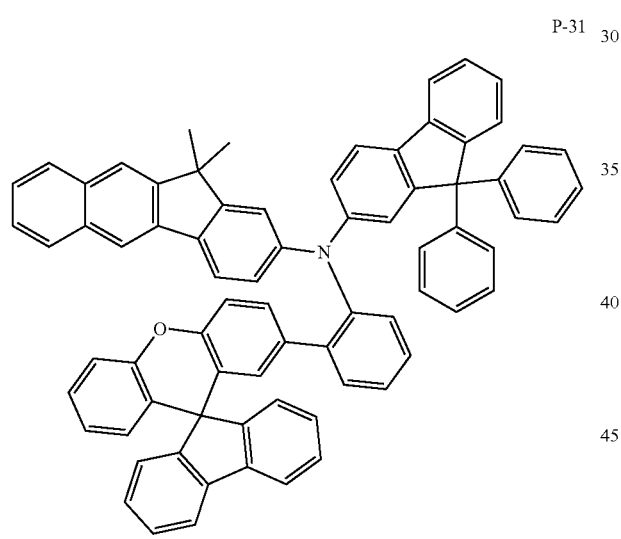
P-34
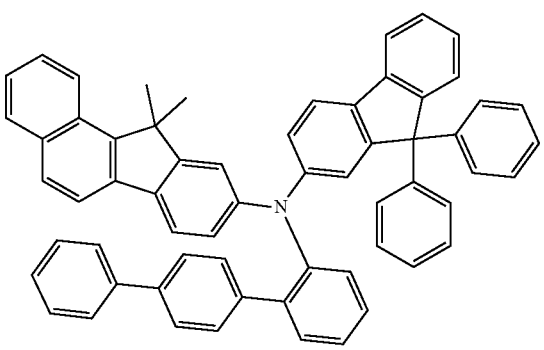
P-32
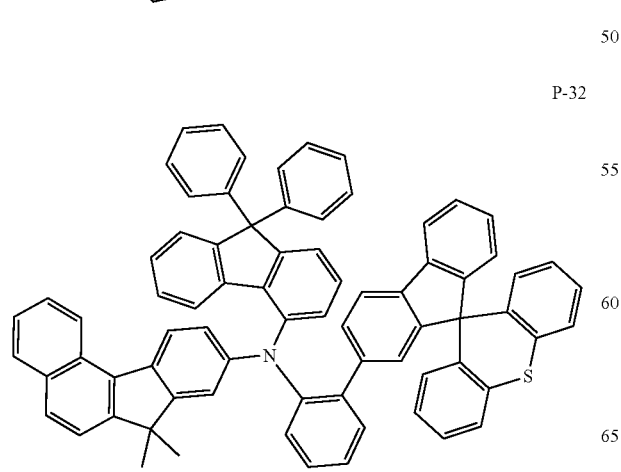
P-35
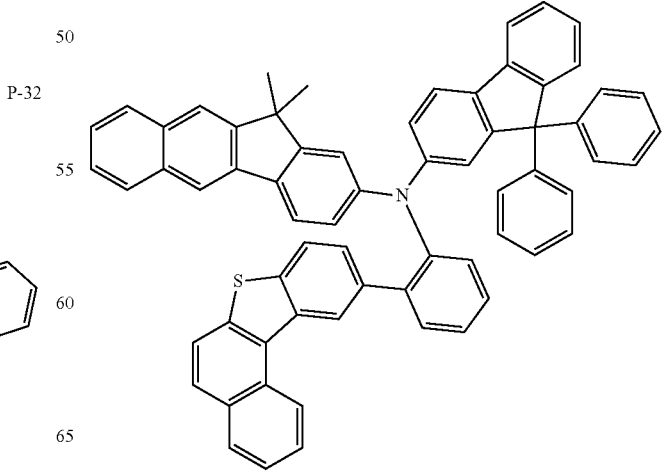

P-36
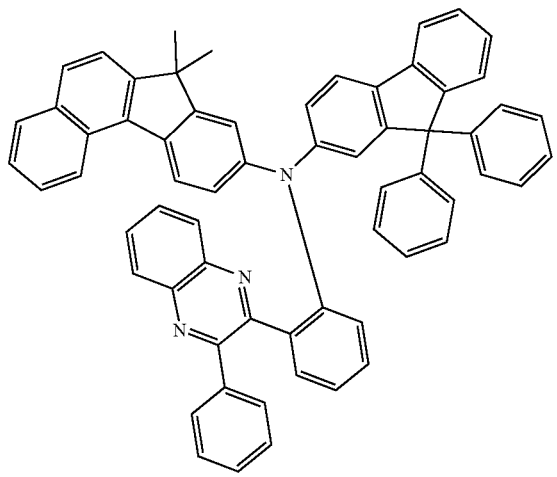
P-37
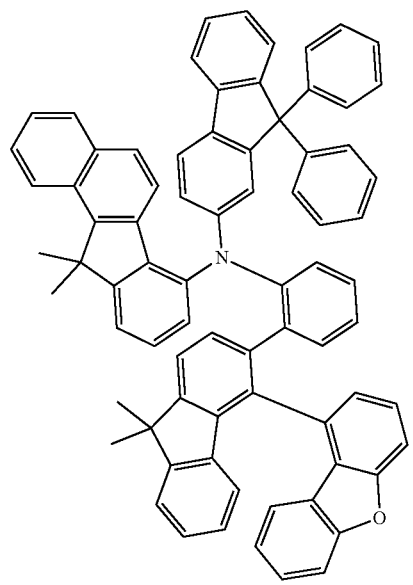
P-38
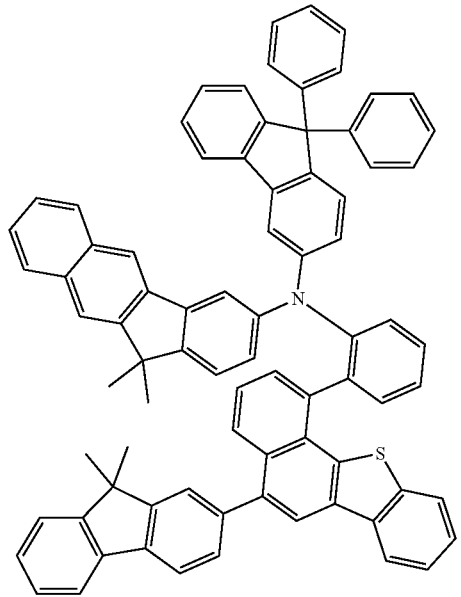
P-39
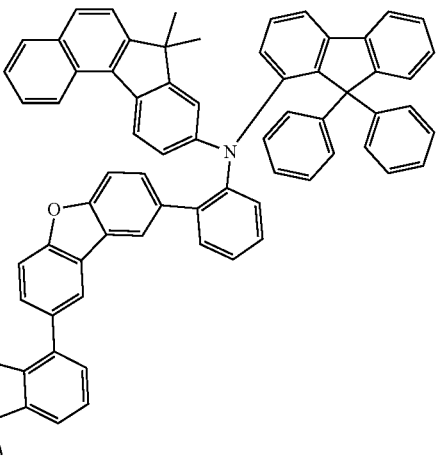
P-40
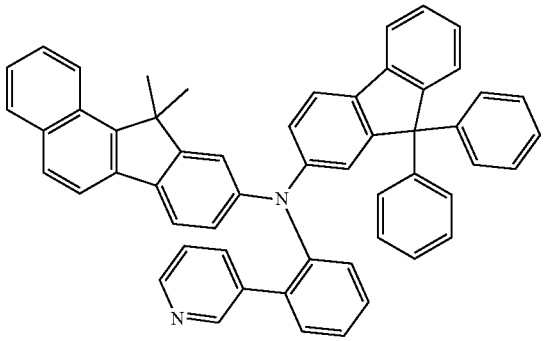
P-41
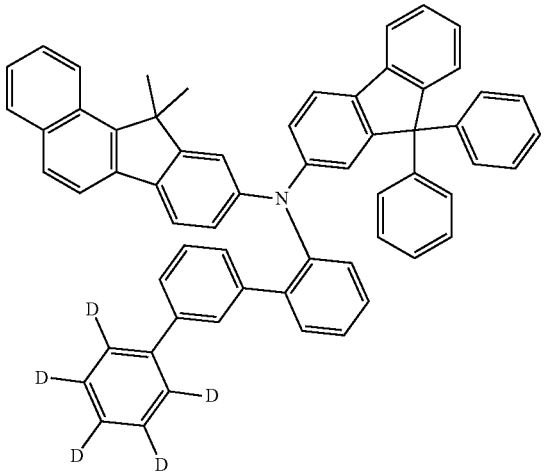

P-42
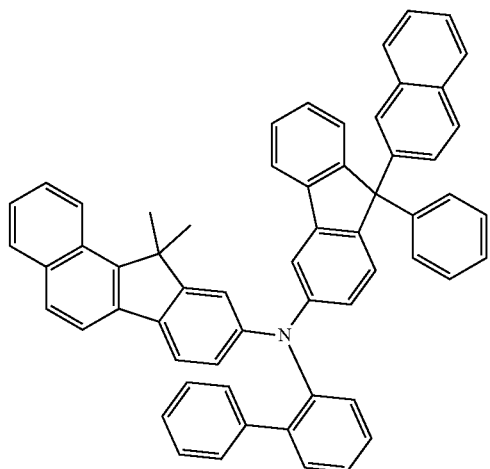
P-43
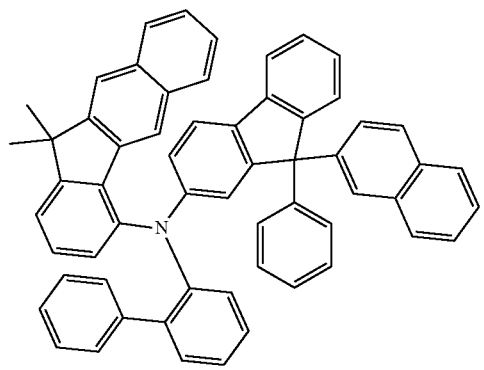
P-44
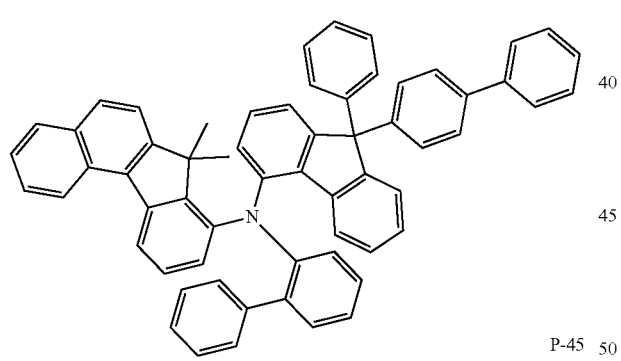
P-45
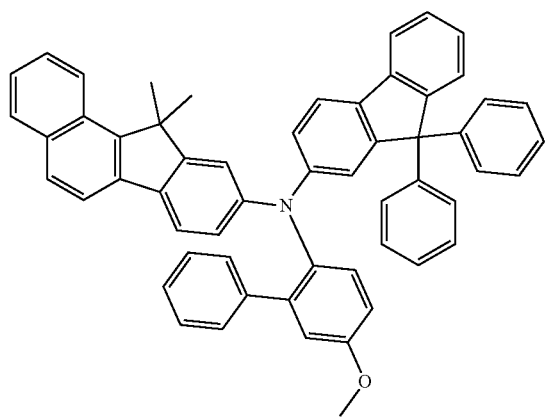
P-46
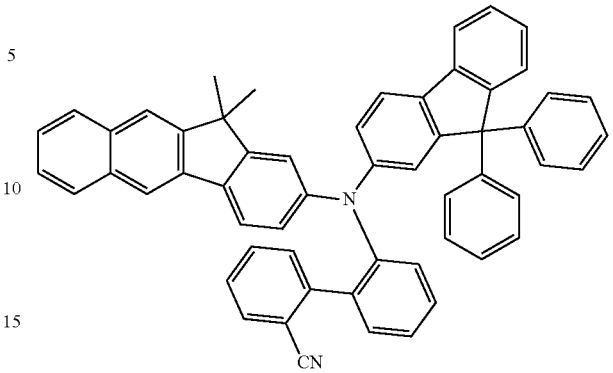
P-47
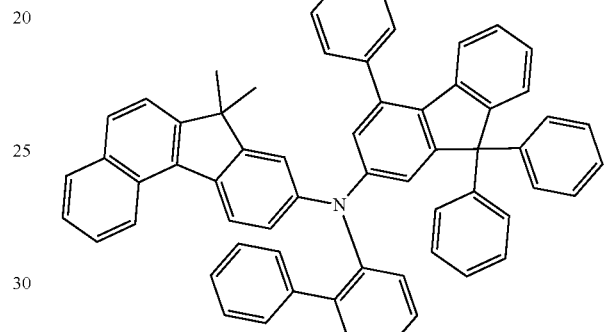
P-48
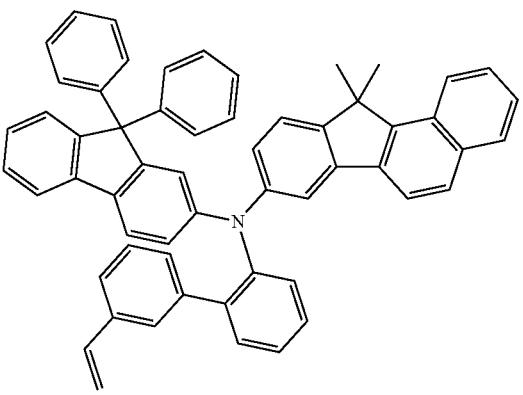
P-49
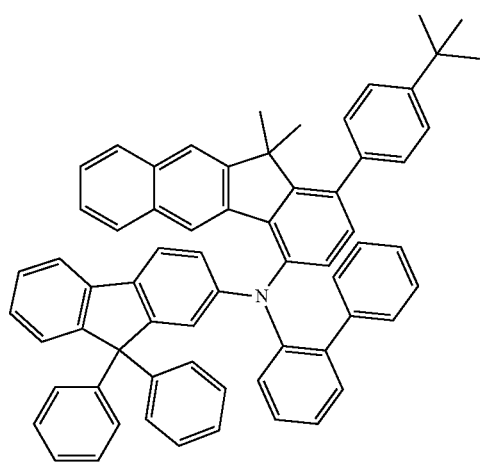

-continued

P-50
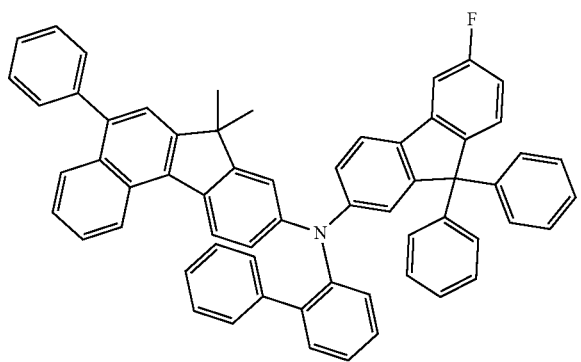

P-51
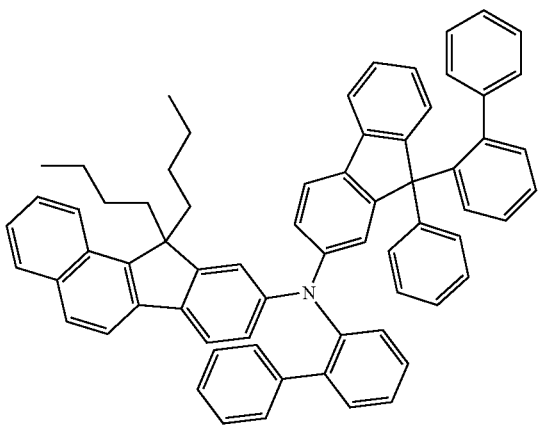

P-52
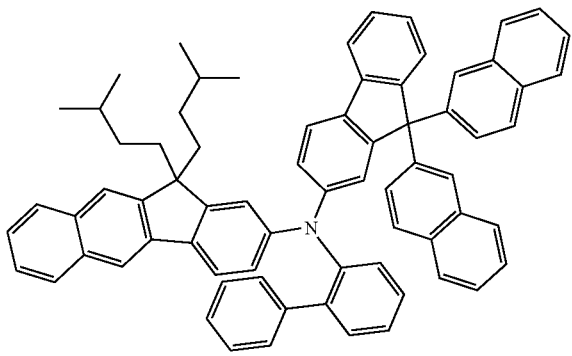

Referring to FIG. 1, the organic electronic element (100) according to the present invention includes a first electrode (110) and a second electrode (170), and an organic material layer including single compound or 2 or more compounds represented by Formula(1) between the first electrode (110) and the second electrode (170). Here, the first electrode (110) may be an anode or a positive electrode, and the second electrode (170) may be a cathode or a negative electrode. In the case of an inverted organic electronic element, the first electrode may be a cathode, and the second electrode may be an anode.

Figure 2:
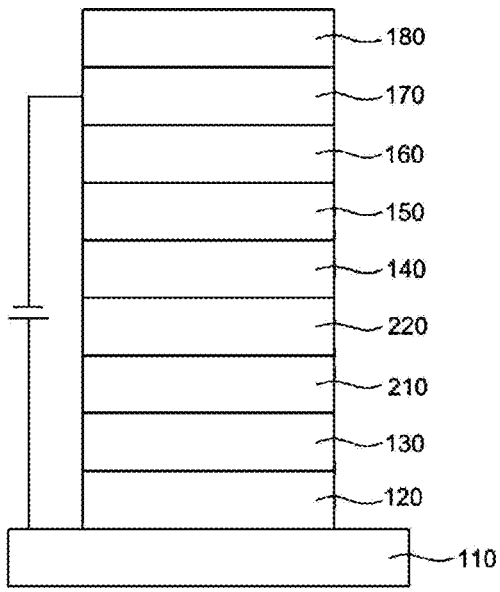

The organic material layer may include a hole injection layer (120), a hole transport layer (130), an emitting layer (140), an electron transport layer (150), and an electron injection layer (160) formed in sequence on the first electrode (110). Here, the remaining layers except the emitting layer (140) may not be formed. The organic material layer may further include a hole blocking layer, an electron blocking layer, an emitting-auxiliary layer (220), a buffer layer (210), etc., and the electron transport layer (150) and the like may serve as a hole blocking layer. (see FIG. 2) Also, the organic electronic element according to an embodiment of the present invention may further include a protective layer or a light efficiency enhancing layer (180). The light efficiency enhancing layer may be formed on a surface not in contact with the organic material layer on both surfaces of the first electrode or on a surface not in contact with the organic material layer on both surfaces of the second electrode. The compound according to an embodiment of the present invention applied to the organic material layer is a hole injection layer (120), a hole transport layer (130), an emitting-auxiliary layer (220), an electron transport auxiliary layer, an electron transport layer (150), an electron injection layer (160), the host or dopant of the emitting layer (140), or the light efficiency enhancing layer material. Preferably, for example, the compound according to Formula (1) of the present invention can be used as a material of the emitting-auxiliary layer.

Figure 3:
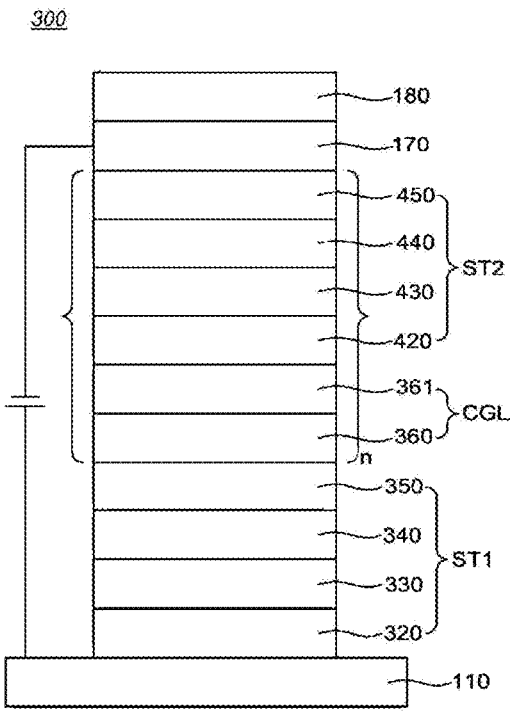
Figure 4:
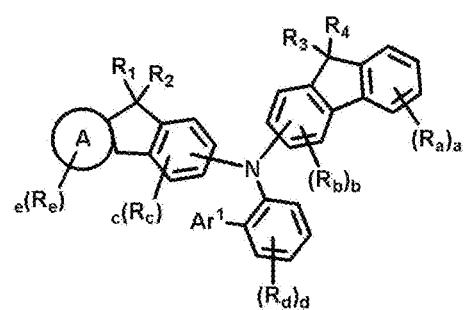
FIG. 4 shows the formula according to one aspect of the present invention.

The organic material layer may include 2 or more stacks including a hole transport layer, an emitting layer, and an electron transport layer sequentially formed on the anode, and may further include a charge generation layer formed between the 2 or more stacks (see FIG. 3).

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (120), the hole transport layer (130), the emitting layer (140), the electron transport layer (150), and the electron injection layer (160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound as an electron transport material.

As another specific example, the present invention provides an organic electronic element that is used by mixing the same or different compounds of the compound represented by Formula (1) to the organic material layer.

In another aspect, the present invention provides an emitting-auxiliary layer composition comprising a compound represented by Formula (1), and provides an organic electronic element comprising the emitting-auxiliary layer.

The present invention also provides an electronic device comprising a display device including the organic electronic element; and a control unit for driving the display device.

According to another aspect, the present invention provides an display device wherein the organic electronic element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis Examples of the compound represented by Formula (1) of the present invention and preparation examples of the organic electronic element of the present invention will be described in detail by way of example, but are not limited to the following examples.

Synthesis Example 1

Final products represented by Formula(1) according to the present invention is prepared by reacting Sub 1 and Sub 2 as shown in Reaction Scheme 1 below.

<Reaction Scheme 1>
Hal=Br, Cl or I

Sub 1-1
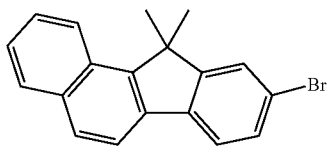

Sub 1-2
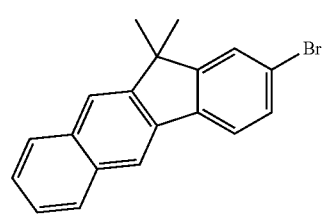

Sub 1-3
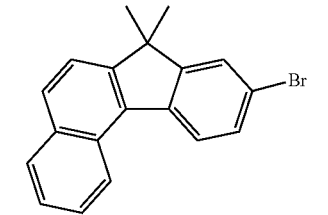

Sub 1-4
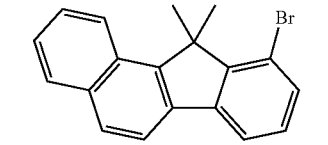

Sub 1-5
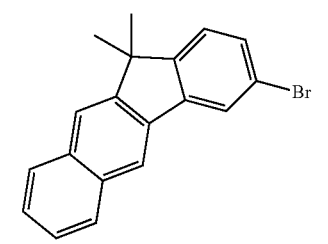

Sub 1-6
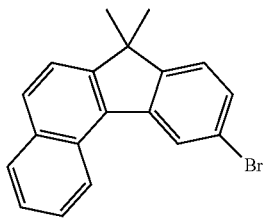

Sub 1-7
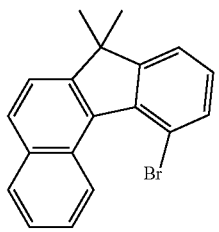

Sub 1-8
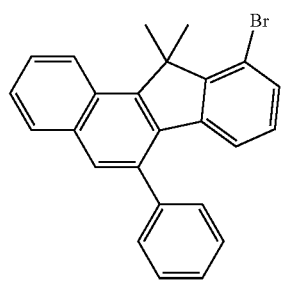

Sub 1-9
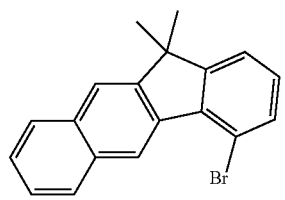

Sub 1-10
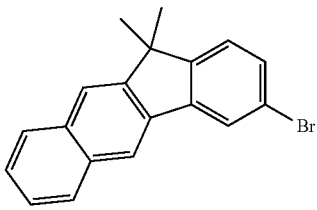

Sub 1-11
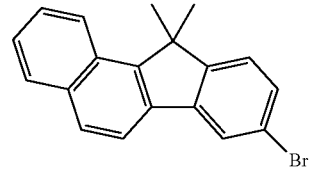

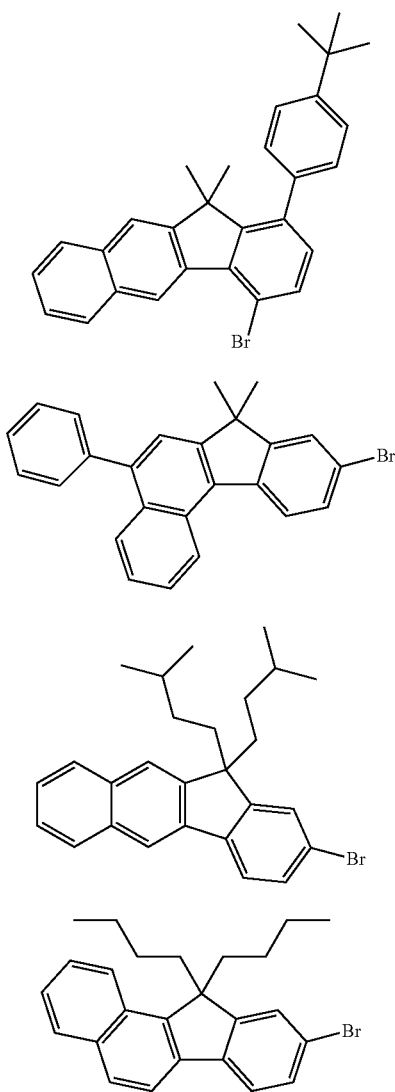
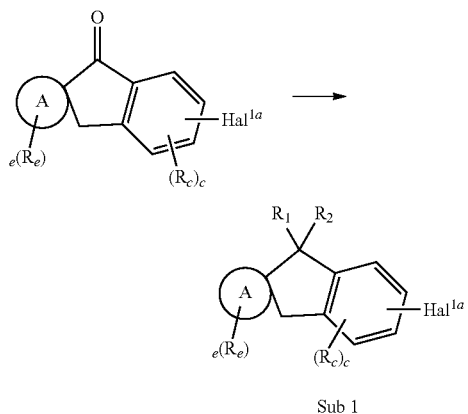
Examples of Sub 1 are as follows, but are not limited thereto. In addition, Table 1 shows Cas Number or FD-MS (Field Desorption-Mass Spectrometry) values of some compounds belonging to Sub 1.
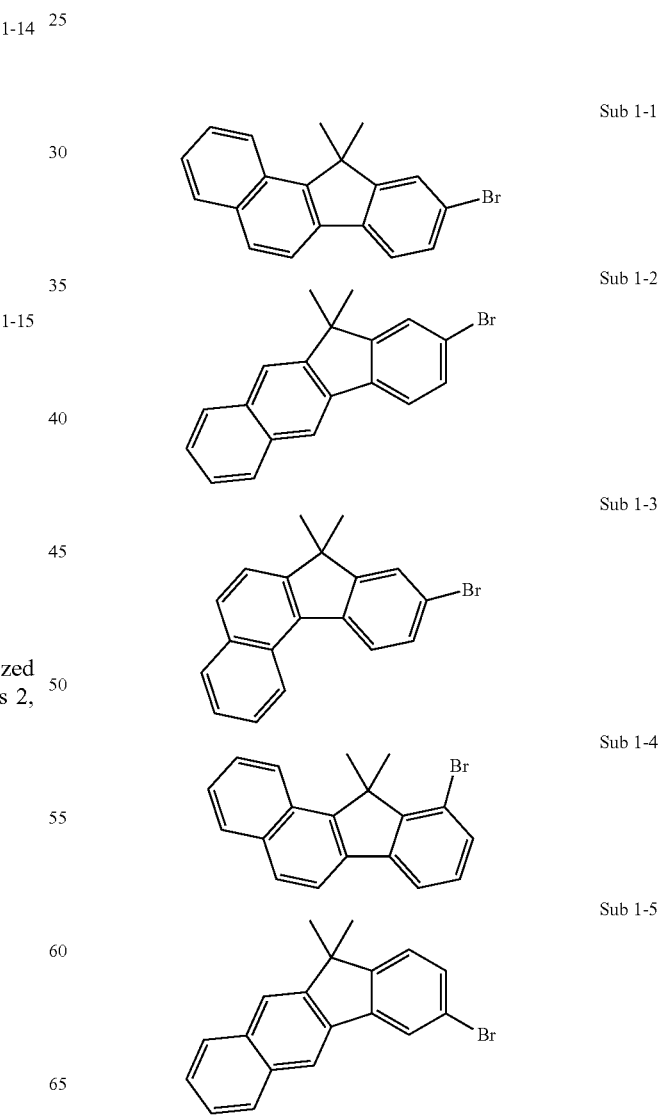
I. Synthesis Example of Sub 1
The Sub 1 of the Reaction Scheme 1 can be synthesized by the reaction path of the following Reaction Schemes 2, but is not limited thereto.
<Reaction Scheme 2>
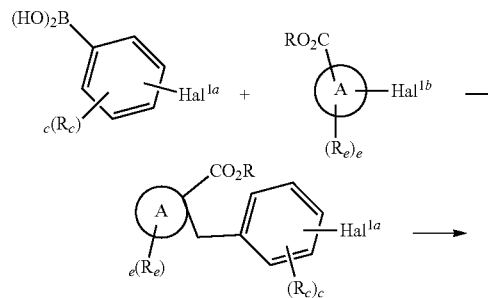

-continued
Sub 1-6
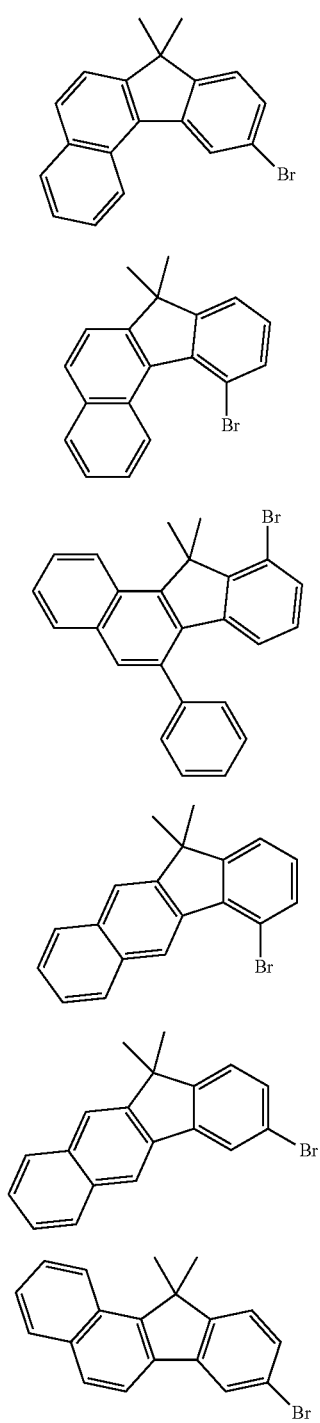
Sub 1-7
Sub 1-8
Sub 1-9
Sub 1-10
Sub 1-11
Sub 1-12
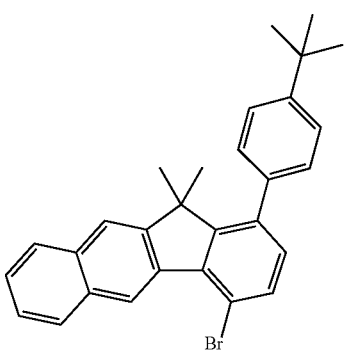
Sub 1-13
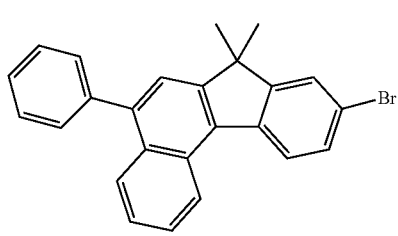
Sub 1-14
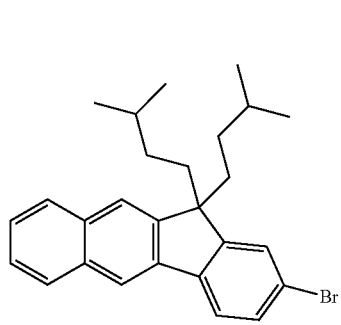
Sub 1-15
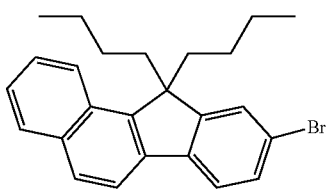
TABLE 1
| compound | CAS RN/FD-MS | compound | CAS RN/FD-MS |
|---|---|---|---|
| Sub 1-1 | 1198396-29-0 | Sub 1-2 | 1198396-39-2 |
| Sub 1-3 | 1198396-46-1 | Sub 1-4 | 1674335-28-4 |
| Sub 1-5 | 1674334-59-8 | Sub 1-6 | 1674334-02-1 |
| Sub 1-7 | 1674334-41-8 | Sub 1-8 | m/z = 398.07($C_{25}H_{19}Br$ = 399.33) |
| Sub 1-9 | 1674334-75-8 | Sub 1-10 | 1674334-59-8 |

TABLE 1-continued

| compound | CAS RN/FD-MS | compound | CAS RN/FD-MS |
|---|---|---|---|
| Sub 1-11 | 1674335-13-7 | Sub 1-12 | m/z = 454.13($C_{29}H_{27}Br$ = 455.44) |
| Sub 1-13 | 1263204-42-7 | Sub 1-14 | m/z = 434.16($C_{27}H_{31}Br$ = 435.45) |
| Sub 1-15 | m/z = 406.13($C_{25}H_{27}Br$ = 407.40) | | |

II. Synthesis Example of Sub 2

The Sub 2 of the Reaction Scheme 1 can be synthesized by the reaction path of the following Reaction Schemes 3, but is not limited thereto.

<Reaction Scheme 3>

Hal=Br, Cl or I

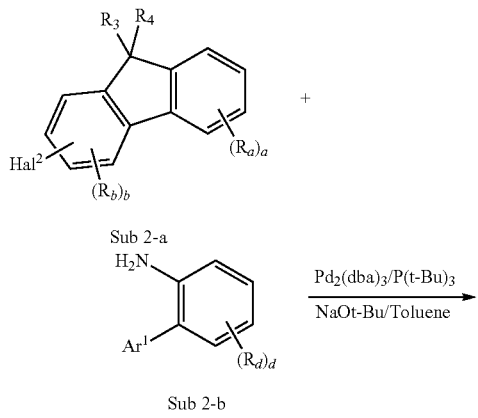

Sub 2-a

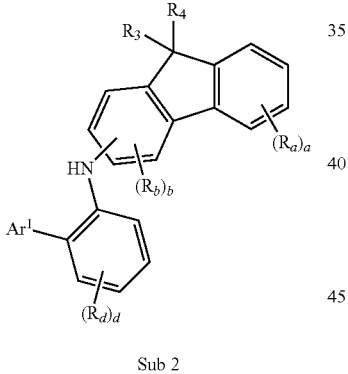

Sub 2

The Sub 2-a and Sub 2-b can be synthesized by the reaction path of the following Reaction Schemes 4 and 5, respectively, but is not limited thereto.

<Reaction Scheme 4>

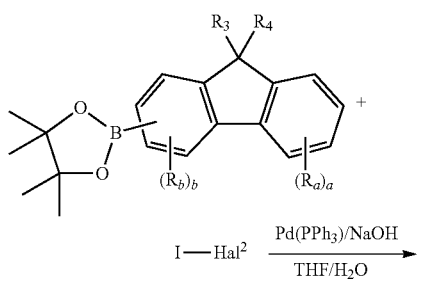

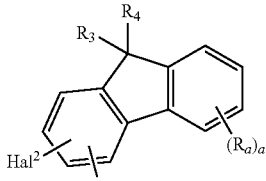

Sub 2-a

<Reaction Scheme 5>

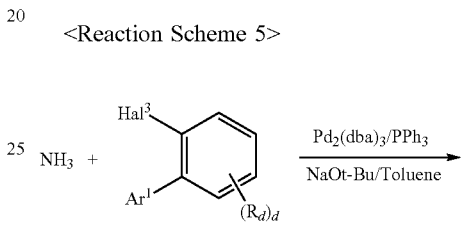

Sub 2-b

1. Synthesis Example of Sub 2-1

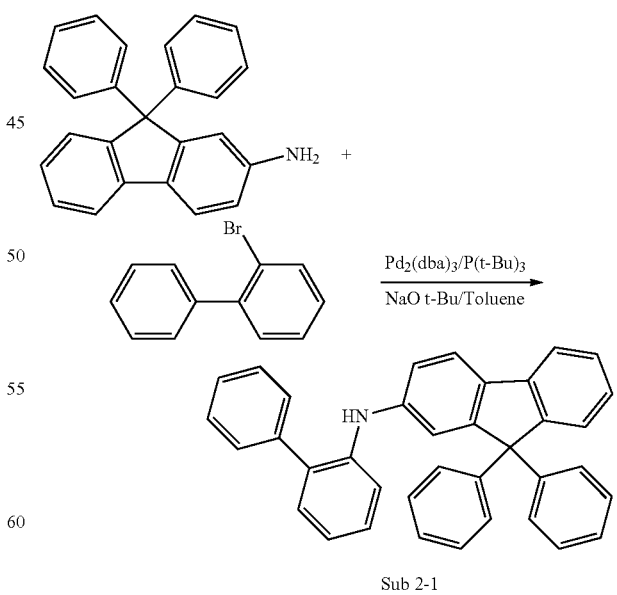

Sub 2-1

In a round bottom flask, 9,9-diphenyl-9H-fluoren-2-amine (35 g, 104.97 mmol), 2-bromo-1,1′-biphenyl (24.47 g, 104.97 mmol), $Pd_2(dba)_3$ (2.88 g, 3.15 mmol), P(t-Bu)$_3$ (1.70 g, 8.40 mmol), NaOt-Bu (30.27 g, 314.91 mmol), toluene (1050 ml) were added and stirred at 100° C. When the reaction was complete, the reaction mixture was extracted with CH₂Cl₂ and water. The organic layer was dried over MgSO₄ and concentrated. The resulting compound was separated by silicagel column chromatography and recrystallization to obtain 43.33 g (yield: 85%) of Sub 2-1.

2. Synthesis Example of Sub 2-17

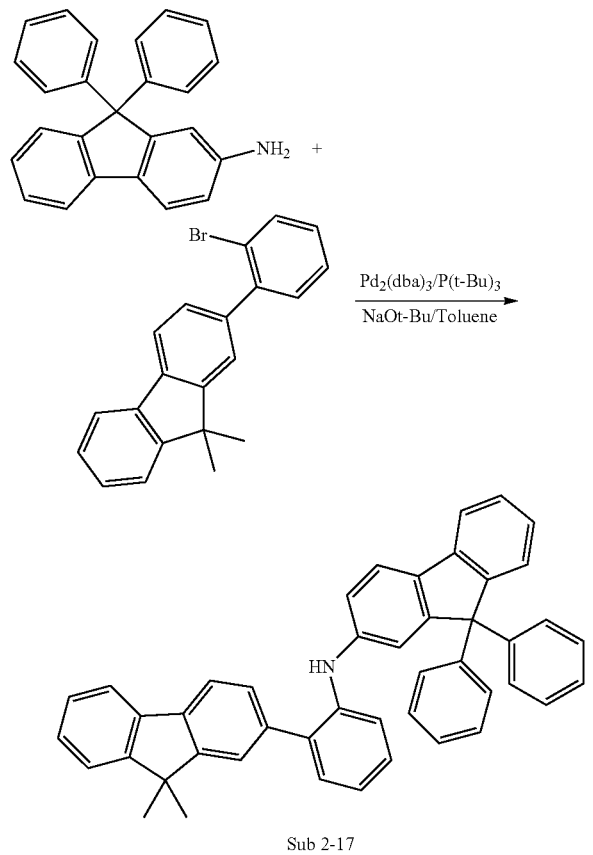

Sub 2-17

9,9-diphenyl-9H-fluoren-2-amine (30 g, 89.97 mmol), 2-(2-bromophenyl)-9,9-dimethyl-9H-fluorene (31.43 g, 89.97 mmol), Pd₂(dba)₃ (2.47 g, 2.70 mmol), P(t-Bu)₃ (1.46 g, 7.20 mmol), NaOt-Bu (25.94 g, 269.92 mmol), Toluene (900 ml) were added, and carried out in the same manner as Sub 2-1 to obtain 41.69 g of Sub 2-17 (yield: 77%)

3. Synthesis Example of Sub 2-24

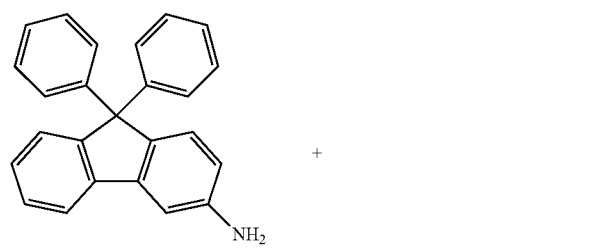

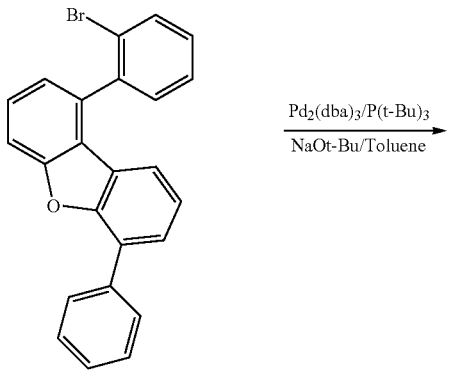

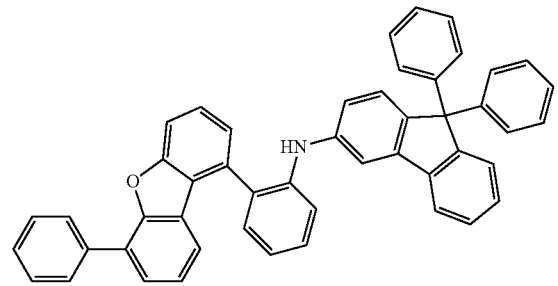

Sub 2-24

9,9-diphenyl-9H-fluoren-3-amine (26 g, 77.98 mmol), 1-(2-bromophenyl)-6-phenyldibenzo [b,d]furan (31.14 g, 77.98 mmol), Pd₂(dba)₃ (2.14 g, 2.34 mmol), P(t-Bu)₃ (1.26 g, 6.24 mmol), NaOt-Bu (22.48 g, 233.93 mmol), Toluene (780 ml) were added, and carried out in the same manner as Sub 2-1 to obtain 40.66 g of Sub 2-24 (yield: 80%)

4. Synthesis Example of Sub 2-28

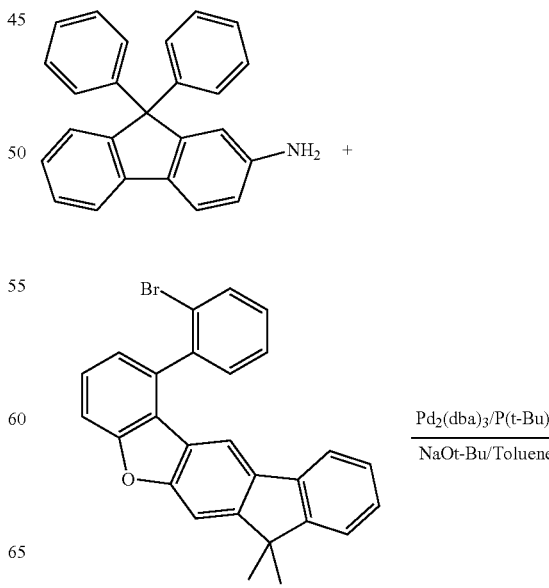

-continued

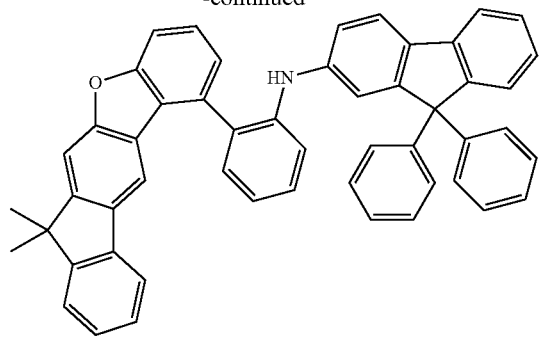

Sub 2-28

9,9-diphenyl-9H-fluoren-2-amine (31 g, 92.97 mmol), 1-(2-bromophenyl)-7,7-dimethyl-7H-fluoreno[2,3-b]benzofuran (40.85 g, 92.97 mmol), Pd₂(dba)₃ (2.55 g, 2.79 mmol), P(t-Bu)₃ (1.50 g, 7.44 mmol), NaOt-Bu (26.81 g, 278.92 mmol), Toluene (930 ml) were added, and carried out in the same manner as Sub 2-1 to obtain 47.60 g of Sub 2-28 (yield: 74%)

5. Synthesis Example of Sub 2-35

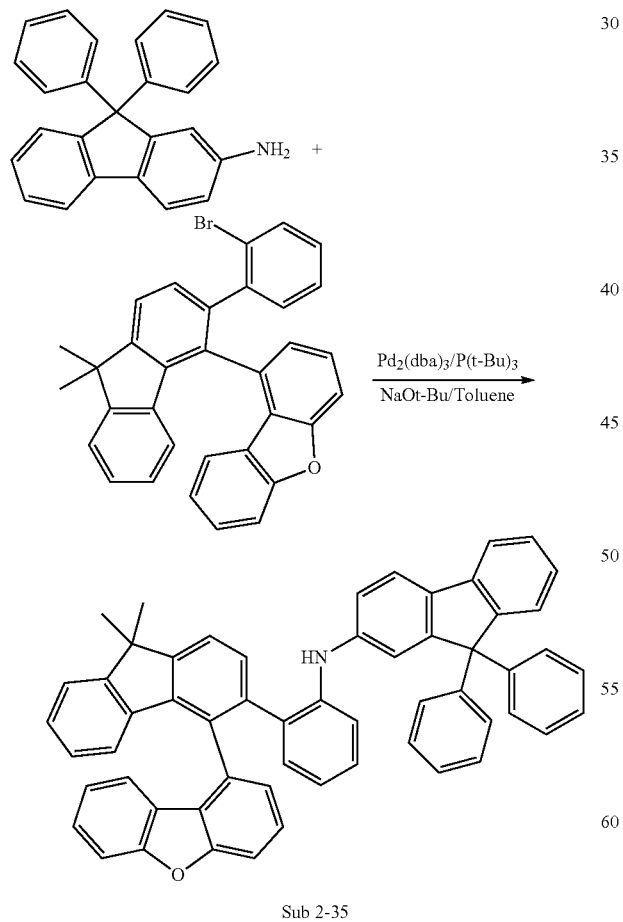

Sub 2-35

9,9-diphenyl-9H-fluoren-2-amine (22 g, 65.98 mmol), 1-(3-(2-bromophenyl)-9,9-dimethyl-9H-fluoren-4-yl) dibenzo[b,d]furan (34.01 g, 65.98 mmol), Pd₂(dba)₃ (1.81 g, 1.98 mmol), P(t-Bu)₃ (1.07 g, 5.28 mmol), NaOt-Bu (19.02 g, 197.94 mmol), Toluene (660 ml) were added, and carried out in the same manner as Sub 2-1 to obtain 35.98 g of Sub 2-35 (yield: 71%)

Examples of Sub 2 are as follows, but are not limited thereto. In addition, Table 2 shows FD-MS (Field Desorption-Mass Spectrometry) values of some compounds belonging to Sub 2.

Sub 2-1

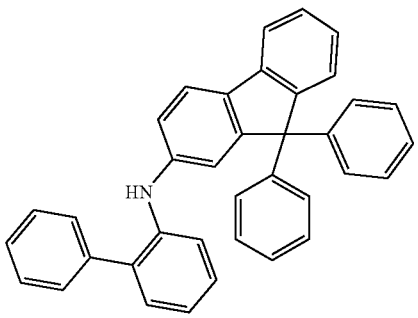

Sub 2-2

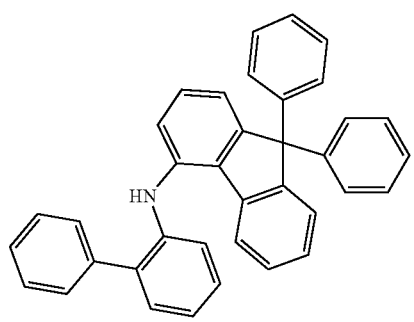

Sub 2-3

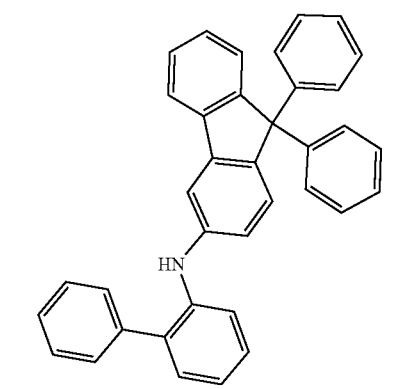

Sub 2-4

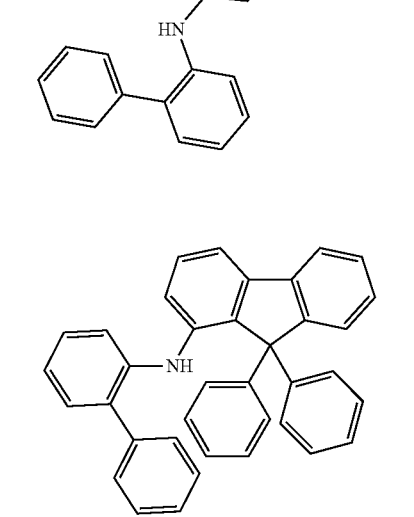

Sub 2-5
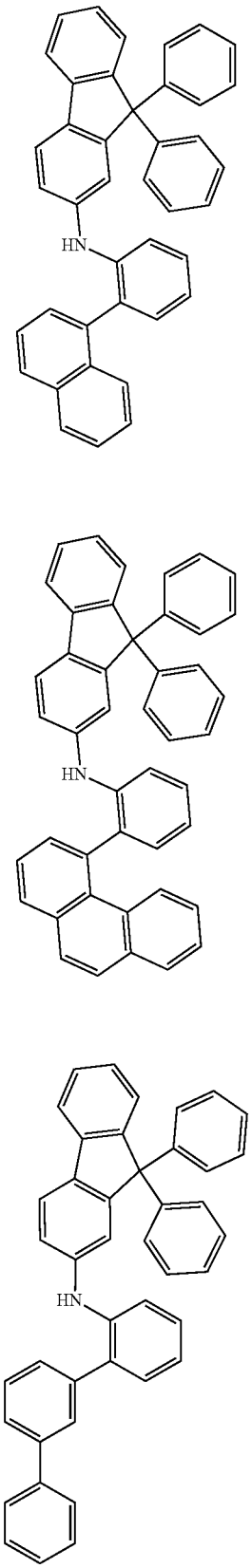
Sub 2-6
Sub 2-7
Sub 2-8
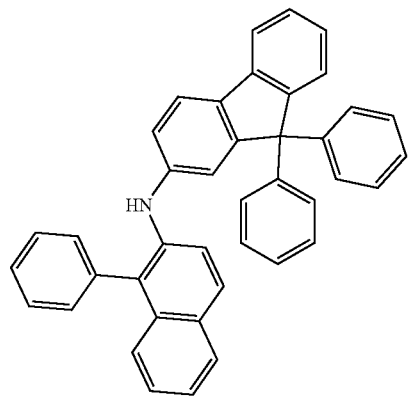
Sub 2-9
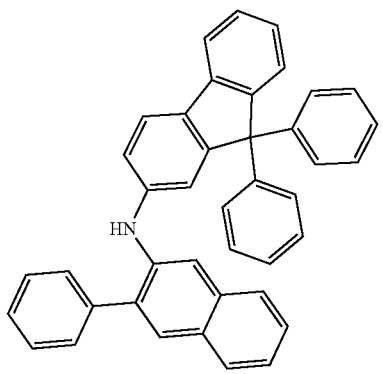
Sub 2-10
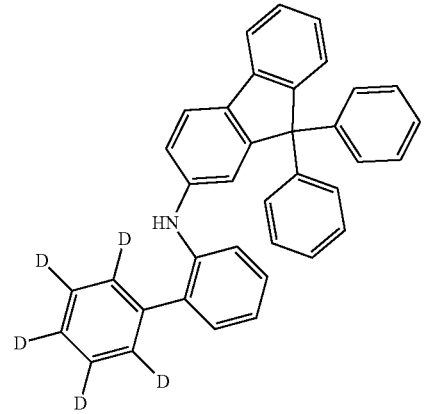
Sub 2-11
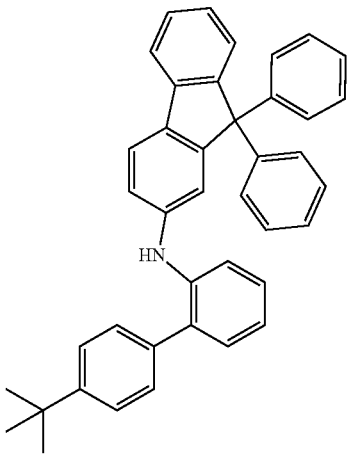

Sub 2-12
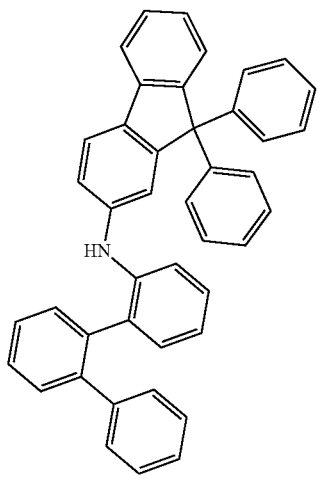
Sub 2-13
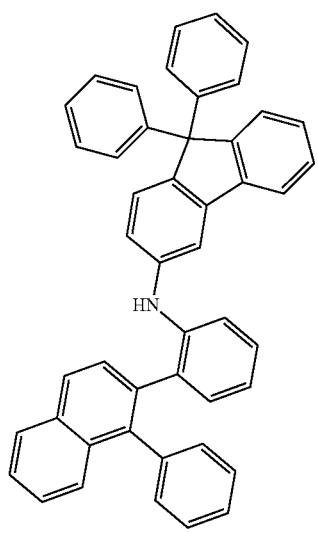
Sub 2-14
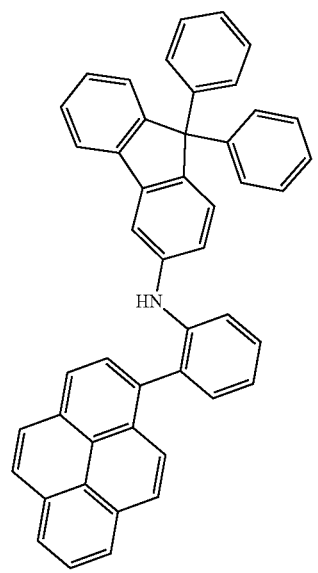
Sub 2-15
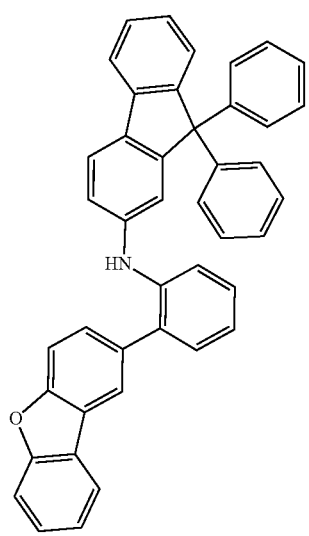
Sub 2-16
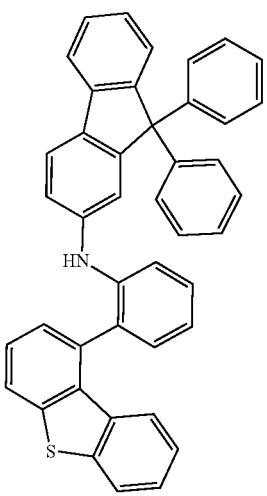
Sub 2-17
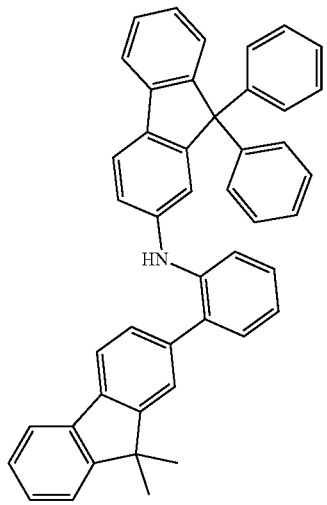

Sub 2-18
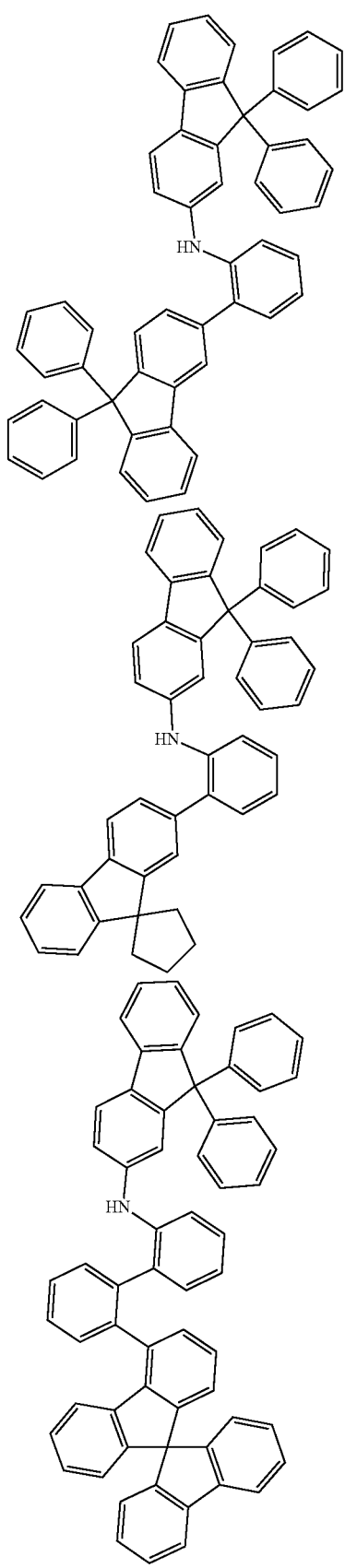
Sub 2-19
Sub 2-20
Sub 2-21
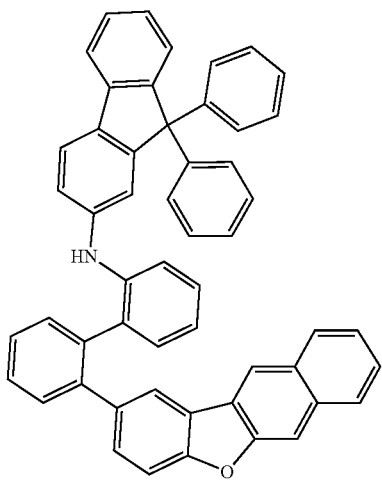
Sub 2-22
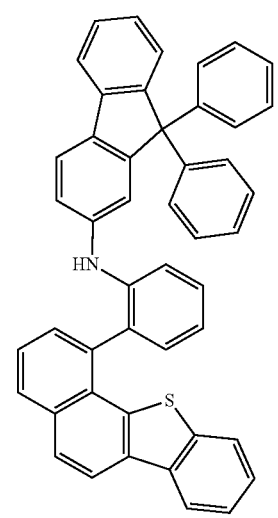
Sub 2-23
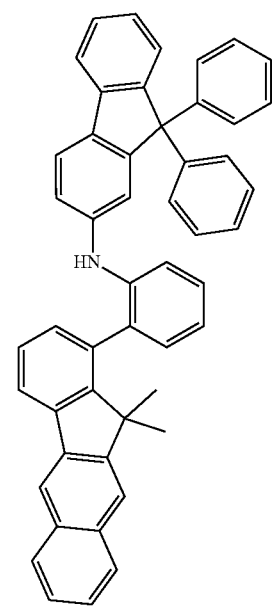

Sub 2-24
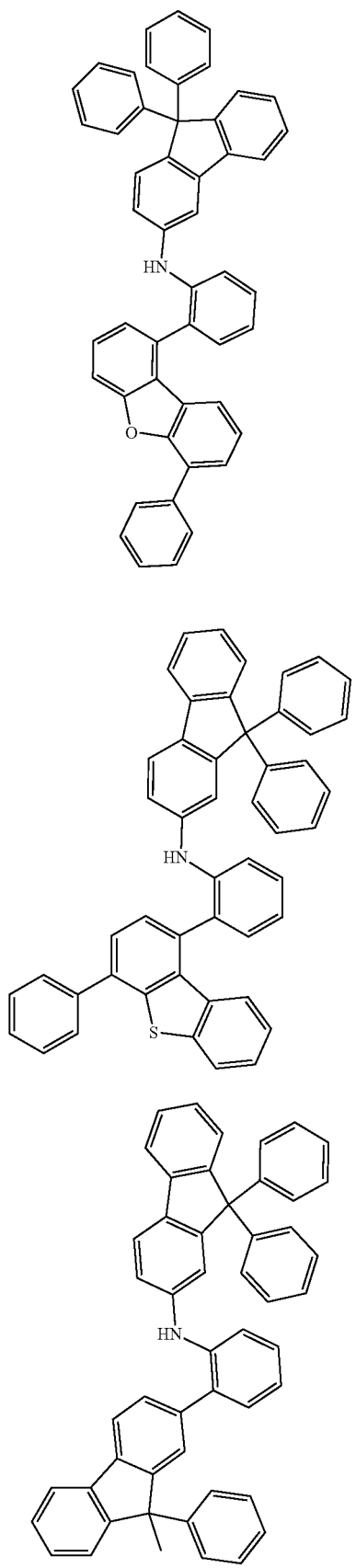
Sub 2-25
Sub 2-26
Sub 2-27
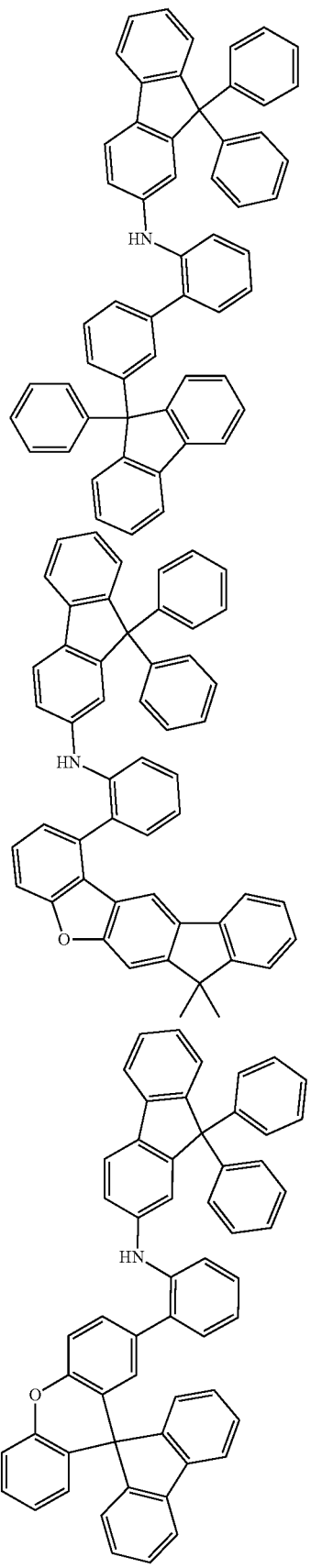
Sub 2-28
Sub 2-29

Sub 2-30
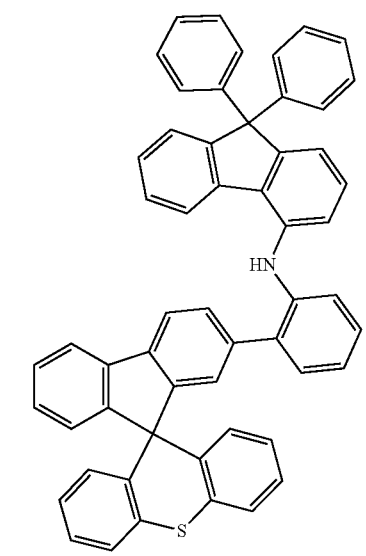
Sub 2-33
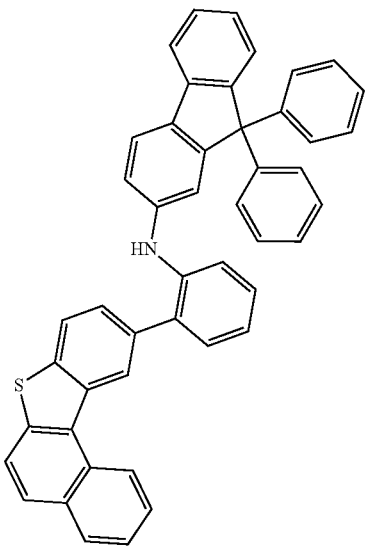
Sub 2-31
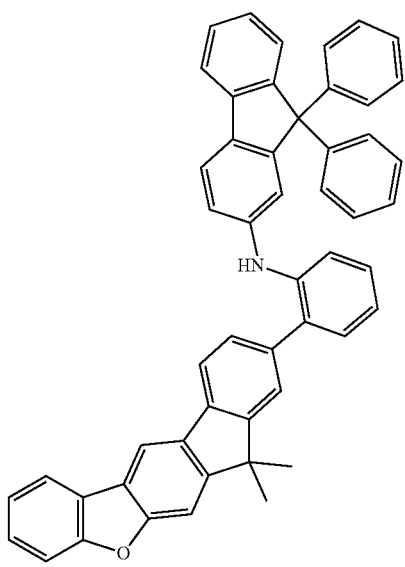
Sub 2-34
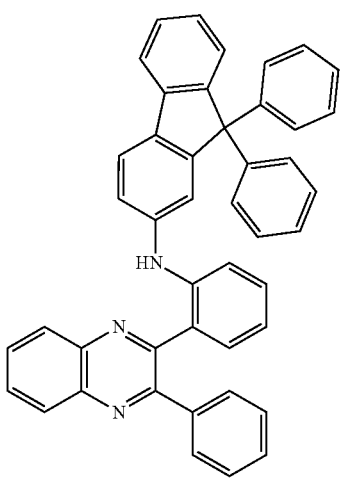
Sub 2-32
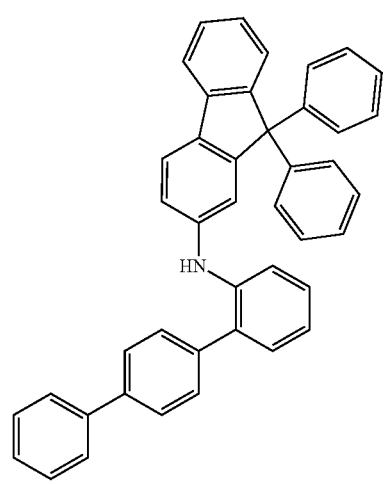
Sub 2-35
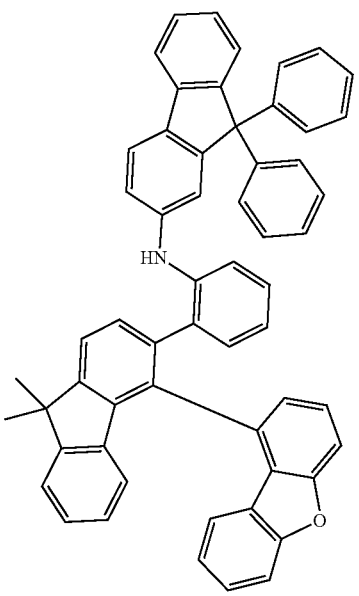

Sub 2-36
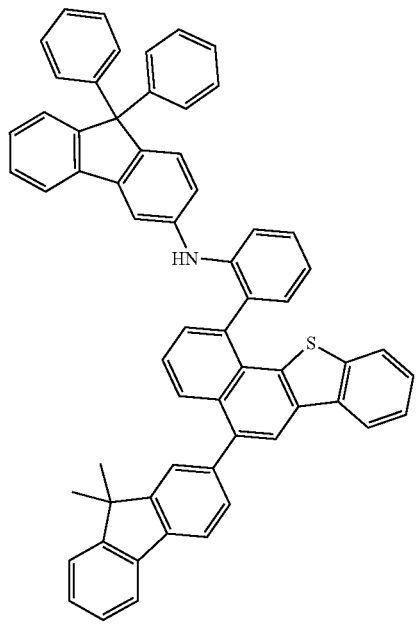
Sub 2-37
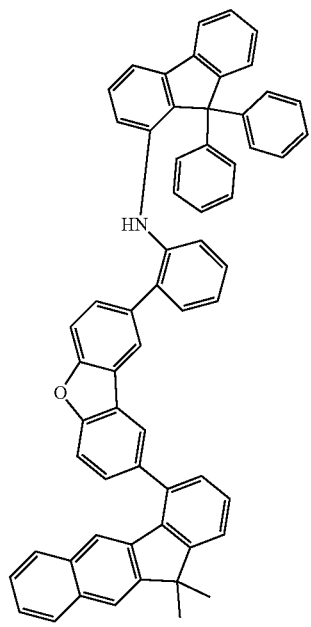
Sub 2-38
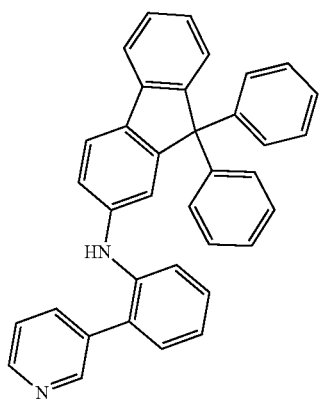
Sub 2-39
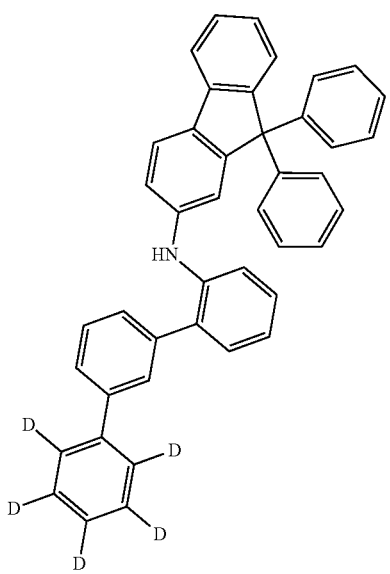
Sub 2-40
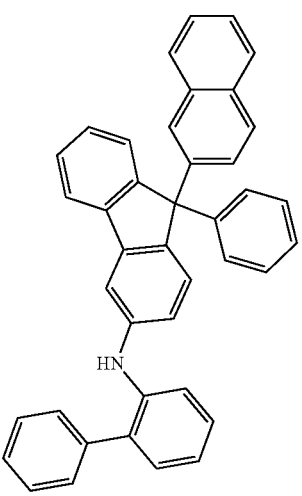
Sub 2-41
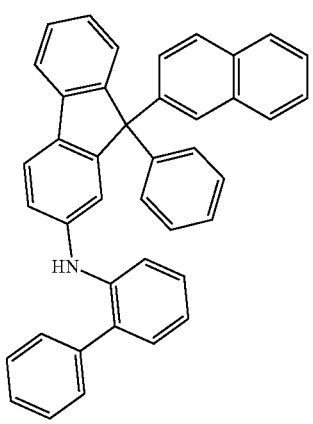

Sub 2-42
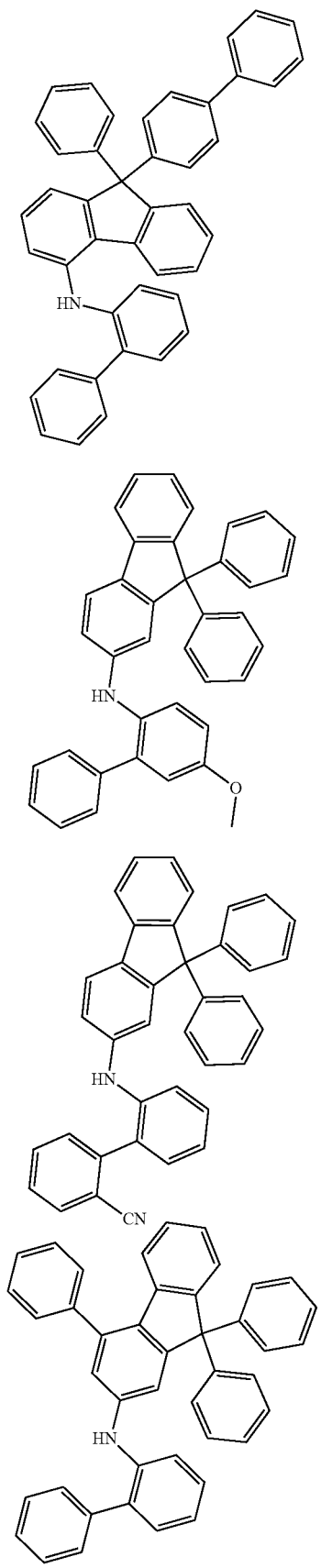
Sub 2-43
Sub 2-44
Sub 2-45
Sub 2-46
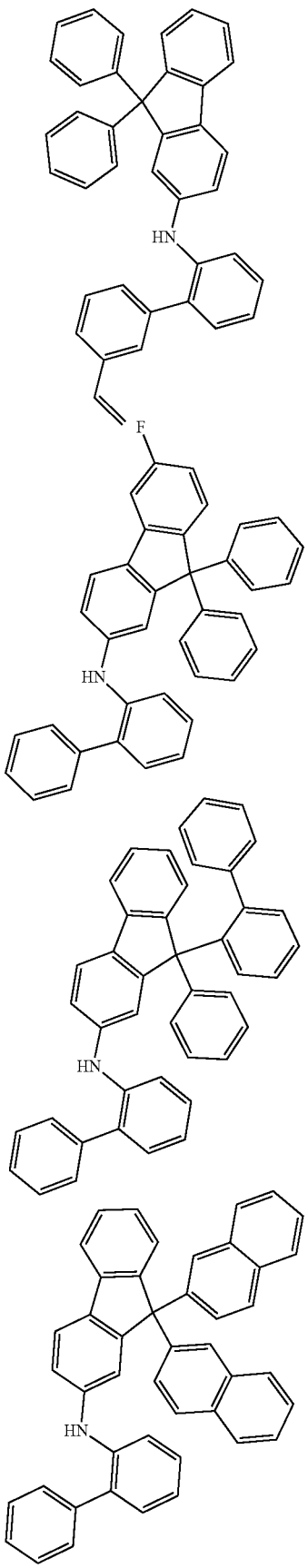
Sub 2-47
Sub 2-48
Sub 2-49

TABLE 2

| compound | FD-MS | compound | FD-MS |
|---|---|---|---|
| Sub 2-1 | m/z = 485.21($C_{37}H_{27}N$ = 485.63) | Sub 2-2 | m/z = 485.21($C_{37}H_{27}N$ = 485.63) |
| Sub 2-3 | m/z = 485.21($C_{37}H_{27}N$ = 485.63) | Sub 2-4 | m/z = 485.21($C_{37}H_{27}N$ = 485.63) |
| Sub 2-5 | m/z = 535.23($C_{41}H_{29}N$ = 535.69) | Sub 2-6 | m/z = 585.25($C_{45}H_{31}N$ = 585.75) |
| Sub 2-7 | m/z = 561.25($C_{43}H_{31}N$ = 561.73) | Sub 2-8 | m/z = 535.23($C_{41}H_{29}N$ = 535.69) |
| Sub 2-9 | m/z = 535.23($C_{41}H_{29}N$ = 535.69) | Sub 2-10 | m/z = 490.25($C_{37}H_{22}D_5N$ = 490.66) |
| Sub 2-11 | m/z = 541.28($C_{41}H_{35}N$ = 541.74) | Sub 2-12 | m/z = 561.25($C_{43}H_{31}N$ = 561.73) |
| Sub 2-13 | m/z = 611.26($C_{47}H_{33}N$ = 611.79) | Sub 2-14 | m/z = 609.25($C_{47}H_{31}N$ = 609.77) |
| Sub 2-15 | m/z = 575.22($C_{43}H_{29}NO$ = 575.71) | Sub 2-16 | m/z = 591.2($C_{43}H_{29}NS$ = 591.77) |
| Sub 2-17 | m/z = 601.28($C_{46}H_{35}N$ = 601.79) | Sub 2-18 | m/z = 725.31($C_{56}H_{39}N$ = 725.94) |
| Sub 2-19 | m/z = 627.29($C_{48}H_{37}N$ = 627.83) | Sub 2-20 | m/z = 799.32($C_{62}H_{41}N$ = 800.02) |
| Sub 2-21 | m/z = 701.27($C_{53}H_{35}NO$ = 701.87) | Sub 2-22 | m/z = 641.22($C_{47}H_{31}NS$ = 641.83) |
| Sub 2-23 | m/z = 651.29($C_{50}H_{37}N$ = 651.85) | Sub 2-24 | m/z = 651.26($C_{49}H_{33}NO$ = 651.81) |
| Sub 2-25 | m/z = 667.23($C_{49}H_{33}NS$ = 667.87) | Sub 2-26 | m/z = 663.29($C_{51}H_{37}N$ = 663.86) |
| Sub 2-27 | m/z = 725.31($C_{56}H_{39}N$ = 725.94) | Sub 2-28 | m/z = 691.29($C_{52}H_{37}NO$ = 691.87) |
| Sub 2-29 | m/z = 739.29($C_{56}H_{37}NO$ = 739.92) | Sub 2-30 | m/z = 755.26($C_{56}H_{37}NS$ = 755.98) |
| Sub 2-31 | m/z = 691.29($C_{52}H_{37}NO$ = 691.87) | Sub 2-32 | m/z = 561.25($C_{43}H_{31}N$ = 561.73) |
| Sub 2-33 | m/z = 641.22($C_{47}H_{31}NS$ = 641.83) | Sub 2-34 | m/z = 613.25($C_{45}H_{31}N_3$ = 613.76) |
| Sub 2-35 | m/z = 767.32($C_{58}H_{41}NO$ = 767.97) | Sub 2-36 | m/z = 833.31($C_{62}H_{43}NS$ = 834.09) |
| Sub 2-37 | m/z = 817.33($C_{62}H_{43}NO$ = 818.03) | Sub 2-38 | m/z = 486.21($C_{36}H_{26}N_2$ = 486.62) |
| Sub 2-39 | m/z = 566.28($C_{43}H_{26}D_5N$ = 566.76) | Sub 2-40 | m/z = 535.23($C_{41}H_{29}N$ = 535.69) |
| Sub 2-41 | m/z = 535.23($C_{41}H_{29}N$ = 535.69) | Sub 2-42 | m/z = 561.25($C_{43}H_{31}N$ = 561.73) |
| Sub 2-43 | m/z = 515.22($C_{38}H_{29}NO$ = 515.66) | Sub 2-44 | m/z = 510.21($C_{38}H_{26}N_2$ = 510.64) |
| Sub 2-45 | m/z = 561.25($C_{43}H_{31}N$ = 561.73) | Sub 2-46 | m/z = 511.23($C_{39}H_{29}N$ = 511.67) |
| Sub 2-47 | m/z = 503.2($C_{37}H_{26}FN$ = 503.62) | Sub 2-48 | m/z = 561.25($C_{43}H_{31}N$ = 561.73) |
| Sub 2-49 | m/z = 585.25($C_{45}H_{31}N$ = 585.75) | | |

III. Synthesis Example of Final Products

Sub 1 (1 eq.) was dissolved in toluene in a round bottom flask, and Sub 2 (1 eq.), $Pd_2(dba)_3$ (0.03 eq.), P(t-bu)$_3$ (0.08 eq.), NaOt-Bu (3 eq.) were added and stirred at 100° C. After the reaction was completed, the reaction mixture was extracted with $CH_2Cl_2$ and water. The organic layer was dried over $MgSO_4$ and concentrated. The resulting organic material was separated by silicagel column chromatography and recrystallization to obtain the final product.

1. Synthesis Example of P-1

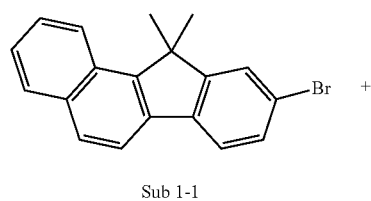

Sub 1-1

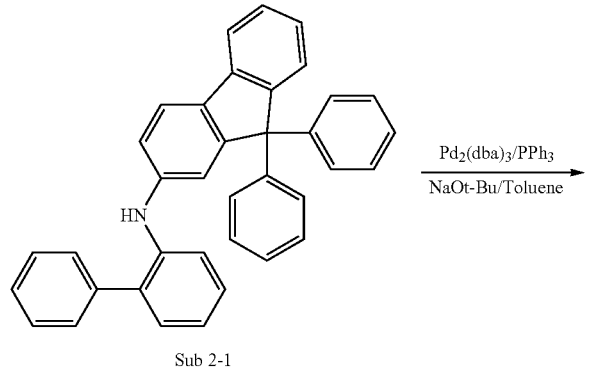

Sub 2-1

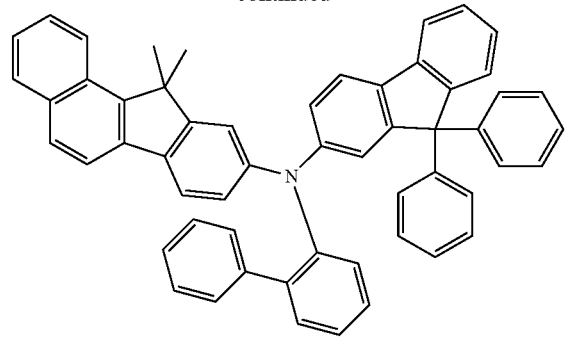

P-1

Sub 1-1 (40 g, 123.75 mmol) was dissolved in toluene (1238 ml) in a round bottom flask, and Sub 2-1 (60.10 g, 123.75 mmol), $Pd_2(dba)_3$ (3.40 g, 3.71 mmol), P(t-Bu)$_3$ (2.00 g, 9.90 mmol), NaOt-Bu (35.68 g, 371.25 mmol) were added and stirred at 100° C. After the reaction was completed, the reaction mixture was extracted with $CH_2Cl_2$ and water. The organic layer was dried over $MgSO_4$ and concentrated. The resulting organic material was separated by silicagel column chromatography and recrystallization to obtain P-1 (75.67 g, yield: 84%).

2. Synthesis Example of P-17

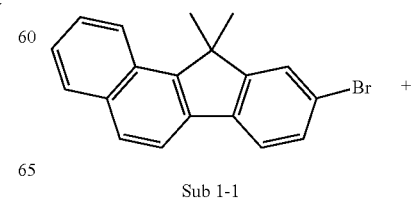

Sub 1-1

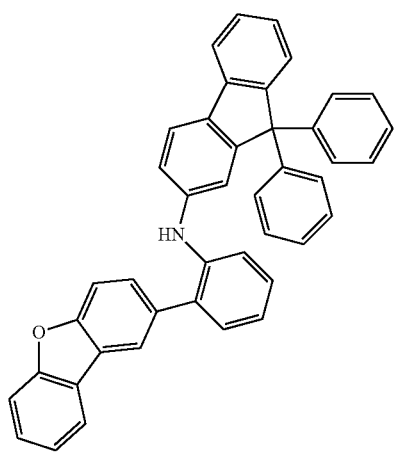
Sub 2-15
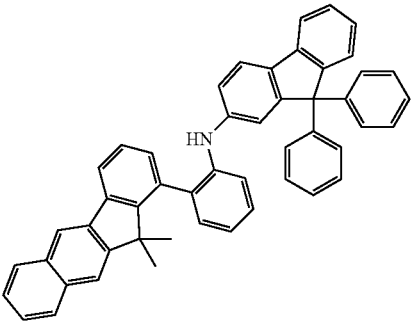
Sub 2-23
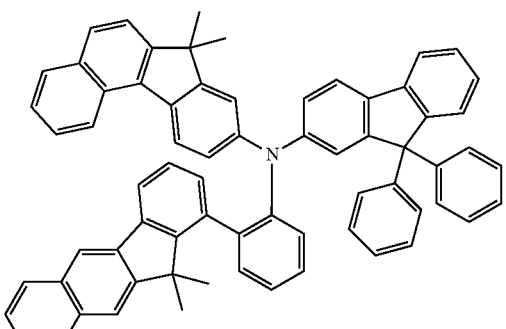
P-25
Sub 2-23 (68.19 g, 102.09 mmol), Pd$_2$(dba)$_3$ (2.80 g, 3.06 mmol), P(t-Bu)$_3$ (1.65 g, 8.17 mmol), NaOt-Bu (29.44 g, 306.28 mmol), Toluene (1021 ml) were added to Sub 1-3 (33 g, 102.09 mmol) and carried out in the same manner as P-1 to obtain 73.94 g of P-25 (yield: 81%)
4. Synthesis Example of P-27
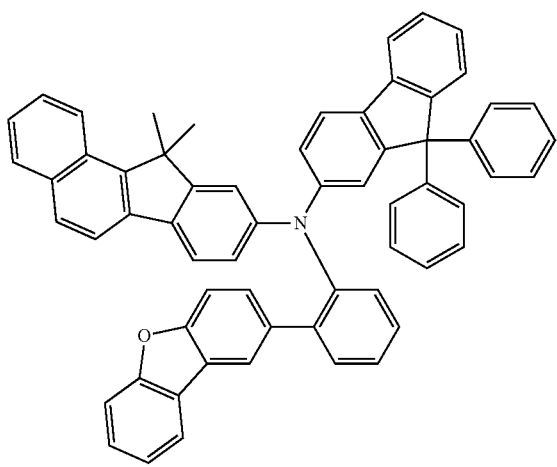
P-17
Sub 2-15 (62.37 g, 108.28 mmol), Pd$_2$(dba)$_3$ (2.97 g, 3.25 mmol), P(t-Bu)$_3$ (1.75 g, 8.66 mmol), NaOt-Bu (31.22 g, 324.85 mmol), Toluene (1083 ml) were added to Sub 1-1 (35 g, 108.28 mmol) and carried out in the same manner as P-1 to obtain 69.98 g of P-17 (yield: 79%)
3. Synthesis Example of P-25
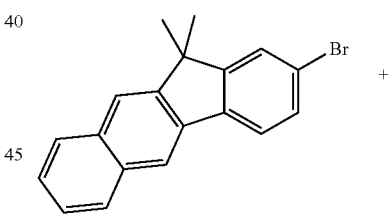
Sub 1-2
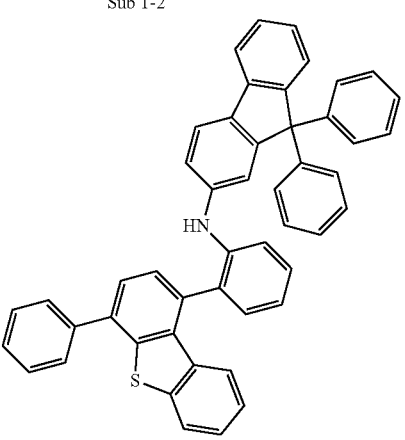
Sub 2-25
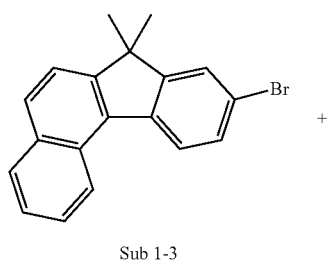
Sub 1-3

-continued

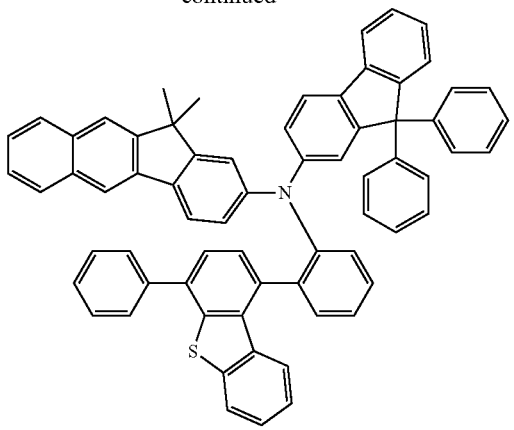

P-27

Sub 2-25 (78.52 g, 117.56 mmol), Pd₂(dba)₃ (3.23 g, 3.53 mmol), P(t-Bu)₃ (1.90 g, 9.41 mmol), NaOt-Bu (33.90 g, 352.69 mmol), Toluene (1176 ml) were added to Sub 1-2 (38 g, 117.56 mmol) and carried out in the same manner as P-1 to obtain 77.04 g of P-27 (yield: 72%)

5. Synthesis Example of P-50

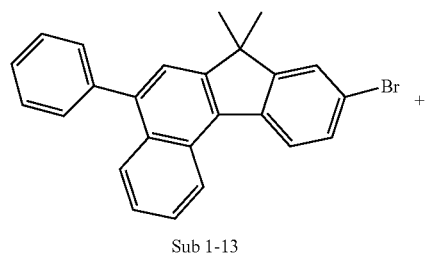

Sub 1-13

-continued

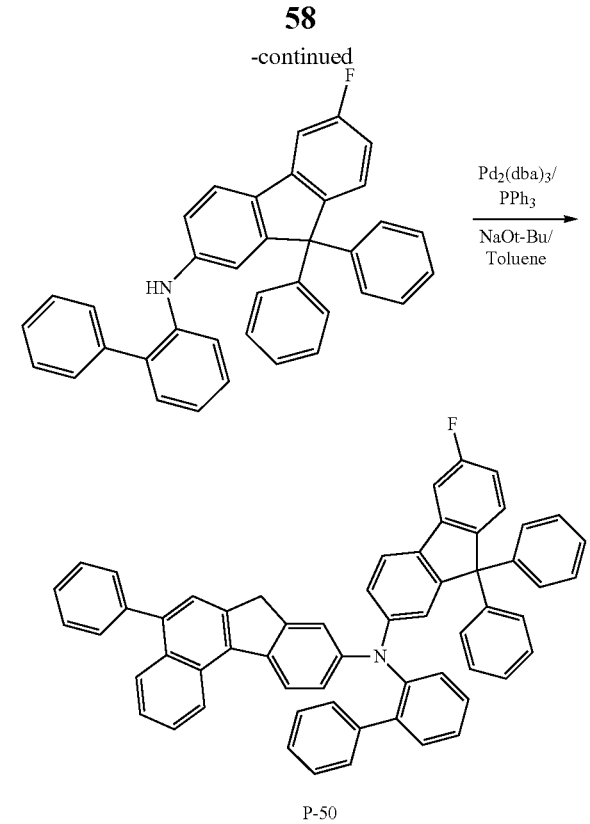

P-50

Sub 2-47 (37.83 g, 75.13 mmol), Pd₂(dba)₃ (2.06 g, 2.25 mmol), P(t-Bu)₃ (1.22 g, 6.01 mmol), NaOt-Bu (21.66 g, 225.38 mmol), Toluene (751 ml) were added to Sub 1-13 (30 g, 75.13 mmol) and carried out in the same manner as P-1 to obtain 43.23 g of P-50 (yield: 70% o)

FD-MS values of the compounds P-1 to P-52 of the present invention prepared according to the synthesis examples as described above are shown in Table 3.

TABLE 3

| compound | FD-MS | compound | FD-MS |
|---|---|---|---|
| P-1 | m/z = 727.32($C_{56}H_{41}N$ = 727.95) | P-2 | m/z = 727.32($C_{56}H_{41}N$ = 727.95) |
| P-3 | m/z = 727.32($C_{56}H_{41}N$ = 727.95) | P-4 | m/z = 727.32($C_{56}H_{41}N$ = 727.95) |
| P-5 | m/z = 727.32($C_{56}H_{41}N$ = 727.95) | P-6 | m/z = 727.32($C_{56}H_{41}N$ = 727.95) |
| P-7 | m/z = 777.34($C_{60}H_{43}N$ = 778.0 1) | P-8 | m/z = 827.36($C_{64}H_{45}N$ = 828.07) |
| P-9 | m/z = 803.36($C_{62}H_{45}N$ = 804.05) | P-10 | m/z = 777.34($C_{60}H_{43}N$ = 778.01) |
| P-11 | m/z = 777.34($C_{60}H_{43}N$ = 778.0 1) | P-12 | m/z = 732.36($C_{56}H_{36}D_5N$ = 732.98) |
| P-13 | m/z = 783.39($C_{60}H_{49}N$ = 784.06) | P-14 | m/z = 879.39($C_{68}H_{49}N$ = 880.15) |
| P-15 | m/z = 853.37($C_{66}H_{47}N$ = 854.11) | P-16 | m/z = 851.36($C_{66}H_{45}N$ = 852.09) |
| P-17 | m/z = 817.33 ($C_{62}H_{43}NO$ = 818.03) | P-18 | m/z = 833.31($C_{62}H_{43}NS$ = 834.09) |
| P-19 | m/z = 843.39($C_{65}H_{49}N$ = 844.11) | P-20 | m/z = 967.42($C_{75}H_{53}N$ = 968.26) |
| P-21 | m/z = 869.4($C_{67}H_{51}N$ = 870.15) | P-22 | m/z = 1041.43($C_{81}H_{55}N$ = 1042.34) |
| P-23 | m/z = 943.38($C_{72}H_{49}NO$ = 944.19) | P-24 | m/z = 883.33($C_{66}H_{45}NS$ = 884.15) |
| P-25 | m/z = 893.4($C_{69}H_{51}N$ = 894.17) | P-26 | m/z = 893.37($C_{68}H_{47}NO$ = 894.13) |
| P-27 | m/z = 909.34($C_{68}H_{47}NS$ = 910.19) | P-28 | m/z = 905.4($C_{70}H_{51}N$ = 906.19) |
| P-29 | m/z = 967.42($C_{75}H_{53}N$ = 968.26) | P-30 | m/z = 933.4($C_{71}H_{51}NO$ = 934.2) |
| P-31 | m/z = 981.4($C_{75}H_{51}NO$ = 982.24) | P-32 | m/z = 997.37($C_{75}H_{51}NS$ = 998.3) |
| P-33 | m/z = 933.4($C_{71}H_{51}NO$ = 934.2) | P-34 | m/z = 803.36($C_{62}H_{45}N$ = 804.05) |
| P-35 | m/z = 883.33($C_{66}H_{45}NS$ = 884.15) | P-36 | m/z = 855.36($C_{64}H_{45}N_3$ = 856.09) |
| P-37 | m/z = 1009.43 ($C_{77}H_{55}NO$ = 1010.29) | P-38 | m/z = 1075.42($C_{81}H_{57}NS$ = 1076.41) |
| P-39 | m/z = 1059.44($C_{81}H_{57}NO$ = 1060.35) | P-40 | m/z = 728.32($C_{55}H_{40}N_2$ = 728.94) |
| P-41 | m/z = 808.39($C_{62}H_{40}D_5N$ = 809.08) | P-42 | m/z = 777.34($C_{60}H_{43}N$ = 778.01) |
| P-43 | m/z = 777.34($C_{60}H_{43}N$ = 778.01) | P-44 | m/z = 803.36($C_{62}H_{45}N$ = 804.05) |
| P-45 | m/z = 757.33 ($C_{57}H_{43}NO$ = 757.98) | P-46 | m/z = 752.32($C_{57}H_{40}N_2$ = 752.96) |
| P-47 | m/z = 803.36($C_{62}H_{45}N$ = 804.05) | P-48 | m/z = 753.34($C_{58}H_{43}N$ = 753.99) |
| P-49 | m/z = 859.42($C_{66}H_{53}N$ = 860.16) | P-50 | m/z = 821.35($C_{62}H_{44}FN$ = 822.04) |
| P-51 | m/z = 887.45($C_{68}H_{57}N$ = 888.21) | P-52 | m/z = 939.48($C_{72}H_{61}N$ = 940.29) |

Evaluation of Manufacture of Organic Electronic Element

[Example 1] Green Organic Light Emitting Diode (Hole Injection Layer)

First, on an ITO layer (anode) formed on a glass substrate, $N^1$-(naphthalen-2-yl)-$N^4$,$N^4$-bis(4-(naphthalen-2-yl(phenyl)amino)phenyl)-$N^1$-phenylbenzene-1,4-diamine (hereinafter will be abbreviated as 2-TNATA) was vacuum deposited to a thickness of 60 nm to form a hole injection layer, and Compound P-1 of the present invention was vacuum-deposited to a thickness of 60 nm on the hole injection layer to form a hole transport layer.

Subsequently, an emitting layer with a thickness of 30 nm was formed on the hole transport layer by using 4,4'-N,N'-dicarbazole-biphenyl (hereinafter abbreviated as CBP) as a host and tris(2-phenylpyridine)-iridium (hereinafter abbreviated as Ir(ppy)$_3$) as a dopant in a 90:10 weight ratio.

Subsequently, (1,1'-biphenyl-4-olato)bis(2-methyl-8-quinolinolato)aluminum (hereinafter abbreviated as BAlq) is deposited to a thickness of 5 nm on the emitting layer to form a hole blocking layer, and bis(10-hydroxybenzo[h]quinolinato)beryllium (hereinafter abbreviated as BeBq2) was deposited to a thickness of 40 nm on the hole blocking layer to form an electron transport layer.

Subsequently, LiF was deposited to a thickness of 0.2 nm to form an electron injection layer, and then Al was deposited to a thickness of 150 nm to form a cathode, thereby manufacturing an organic electronic element.

[Example 2] to [Example 17] Green Organic Light Emitting Diode (Hole Injection Layer)

An organic electronic element was manufactured in the same manner as in Example 1, except that the compound of the present invention shown in Table 4 was used instead of the compound P-1 of the present invention as a hole transport layer material.

Comparative Example 1

An organic electroluminescent device was manufactured in the same manner as in Example 1, except that N,N'-Bis(1-naphthalenyl)-N,N'-bis-phenyl-(1,1'-biphenyl)-4,4'-diamine (hereinafter will be abbreviated as NPB) was used as the hole transport layer material.

[Comparative Example 2] to [Comparative Example 10]

An organic electronic element was manufactured in the same manner as in Example 1, except that one of ref 1 to ref 9 was used as the hole transport layer material.

To the OLEDs which were manufactured by examples 1 to 17 and comparative examples 1 to 10 of the present invention, a forward bias direct current voltage was applied, and electroluminescent (EL) properties were measured using PR-650 of Photoresearch Co., and T95 life was measured using a life measuring apparatus manufactured by McScience Inc. with a reference luminance of 5000 cd/m$^2$. In the following table 4, the manufacture of a device and the results of evaluation are shown.

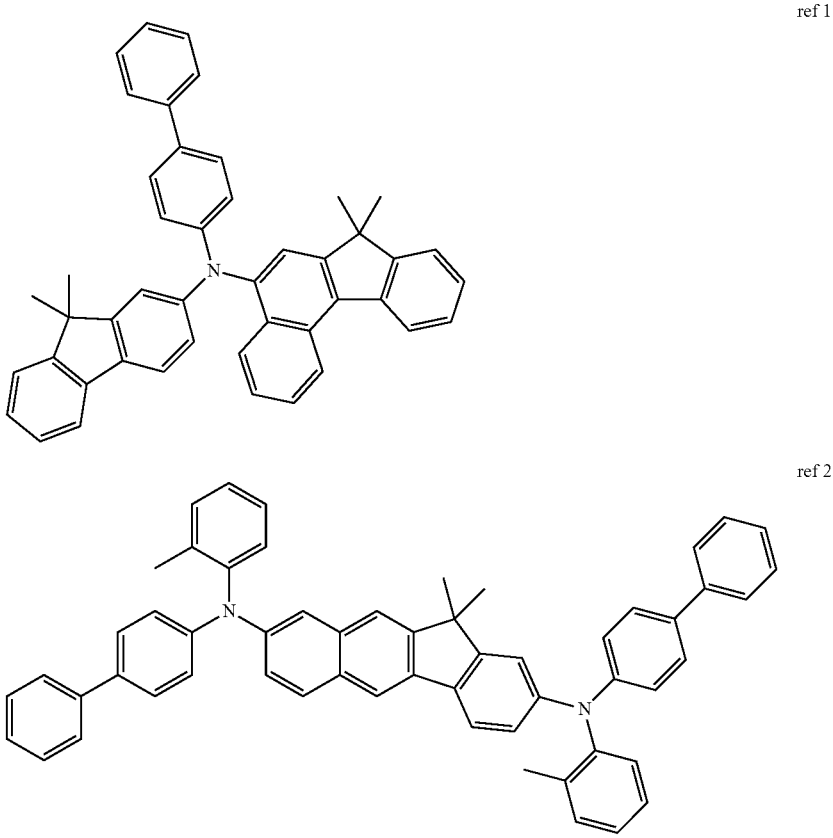

ref 1 ref 2 ref 3
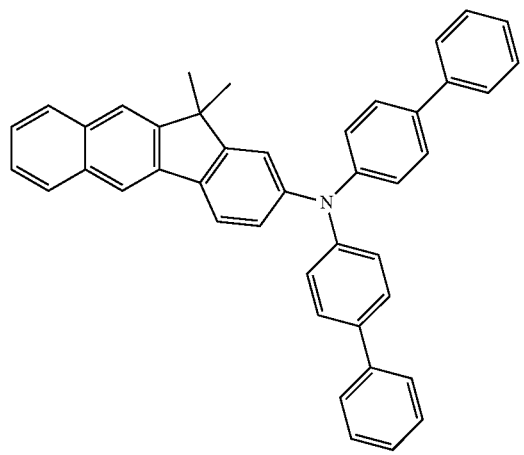
ref 4
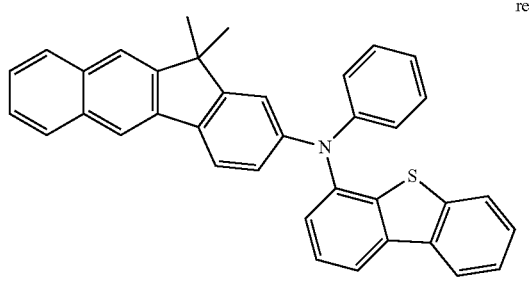
ref 5
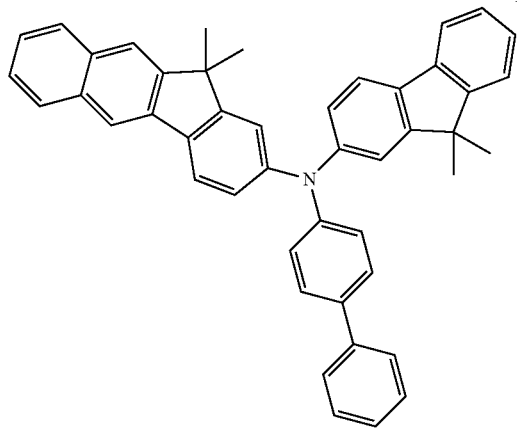
ref 6
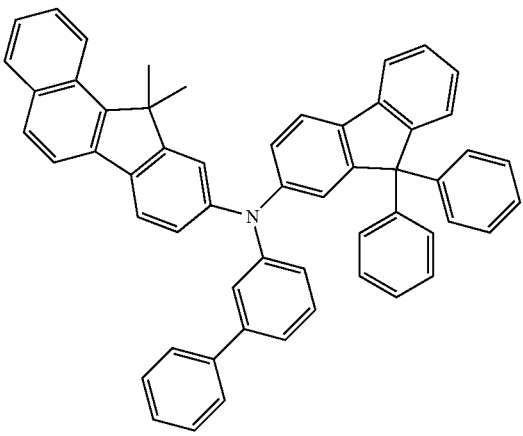

-continued
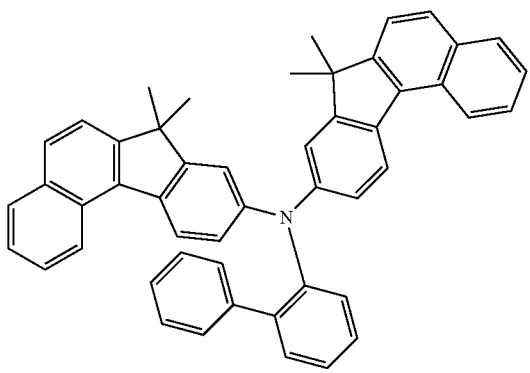
ref 7
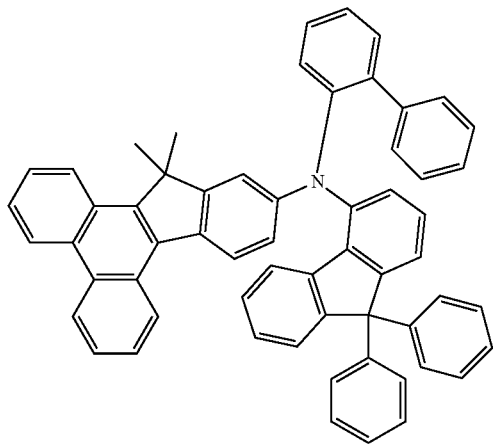
ref 8
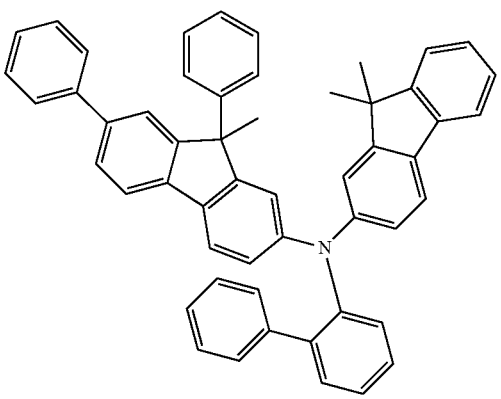
ref 9
TABLE 4
| | compound | Voltage (V) | Current Density (mA)/cm² | Brightness (cd/m²) | Efficiency (cd/A) | Lifetime T(95) | CIE X | CIE Y |
|---|---|---|---|---|---|---|---|---|
| | NPB | 6.0 | 21.5 | 5000 | 23.3 | 57.4 | 0.31 | 0.60 |
| comparative example(2) | ref 1 | 5.9 | 18.9 | 5000 | 26.4 | 72.6 | 0.32 | 0.60 |
| comparative example(3) | ref 2 | 5.9 | 19.2 | 5000 | 26.0 | 72.2 | 0.32 | 0.61 |
| comparative example(4) | ref 3 | 5.8 | 18.7 | 5000 | 26.7 | 73.5 | 0.32 | 0.60 |
| comparative example(5) | ref 4 | 5.8 | 18.1 | 5000 | 27.6 | 74.6 | 0.33 | 0.60 |

TABLE 4-continued

| compound | | Voltage (V) | Current Density (mA)/cm² | Brightness (cd/m²) | Efficiency (cd/A) | Lifetime T(95) | CIE X | CIE Y |
|---|---|---|---|---|---|---|---|---|
| comparative example(6) | ref 5 | 5.7 | 18.5 | 5000 | 27.1 | 74.8 | 0.33 | 0.61 |
| comparative example(7) | ref 6 | 5.6 | 17.5 | 5000 | 28.5 | 83.2 | 0.33 | 0.60 |
| comparative example(8) | ref 7 | 5.6 | 17.9 | 5000 | 28.0 | 80.8 | 0.33 | 0.60 |
| comparative example(9) | ref 8 | 5.6 | 17.4 | 5000 | 28.8 | 81.0 | 0.33 | 0.61 |
| comparative example(10) | ref 9 | 5.5 | 17.8 | 5000 | 28.1 | 79.7 | 0.33 | 0.60 |
| example(1) | P-1 | 5.1 | 12.9 | 5000 | 38.7 | 109.2 | 0.33 | 0.63 |
| example(2) | P-2 | 5.1 | 13.2 | 5000 | 38.0 | 107.5 | 0.33 | 0.62 |
| example(3) | P-3 | 5.1 | 13.1 | 5000 | 38.2 | 108.7 | 0.33 | 0.62 |
| example(4) | P-4 | 5.1 | 13.2 | 5000 | 37.9 | 106.4 | 0.33 | 0.63 |
| example(5) | P-11 | 5.2 | 13.4 | 5000 | 37.3 | 105.6 | 0.33 | 0.62 |
| example(6) | P-14 | 5.4 | 14.5 | 5000 | 34.4 | 100.8 | 0.33 | 0.63 |
| example(7) | P-17 | 5.2 | 12.5 | 5000 | 40.0 | 104.2 | 0.33 | 0.62 |
| example(8) | P-18 | 5.3 | 12.8 | 5000 | 39.1 | 102.1 | 0.33 | 0.63 |
| example(9) | P-19 | 5.1 | 13.0 | 5000 | 38.4 | 108.0 | 0.33 | 0.63 |
| example(10) | P-25 | 5.3 | 13.6 | 5000 | 36.8 | 101.3 | 0.33 | 0.62 |
| example(11) | P-27 | 5.4 | 14.3 | 5000 | 35.0 | 99.5 | 0.33 | 0.62 |
| example(12) | P-34 | 5.1 | 14.0 | 5000 | 35.7 | 106.5 | 0.33 | 0.63 |
| example(13) | P-37 | 5.4 | 15.5 | 5000 | 32.2 | 95.8 | 0.33 | 0.62 |
| example(14) | P-42 | 5.2 | 13.9 | 5000 | 36.1 | 103.2 | 0.33 | 0.62 |
| example(15) | P-49 | 5.4 | 15.2 | 5000 | 33.0 | 96.4 | 0.33 | 0.62 |
| example(16) | P-50 | 5.3 | 14.7 | 5000 | 34.1 | 98.3 | 0.33 | 0.62 |
| example(17) | P-51 | 5.4 | 14.8 | 5000 | 33.8 | 97.6 | 0.33 | 0.62 |

As can be seen from the results of Table 4, it can be seen that the device using the compound represented by Formula (1) of the present invention as a hole transport layer material significantly improved the electrical properties of the device compared to the case of using a comparative compound.

That is, the electrical characteristics (driving voltage, efficiency and lifespan) of Comparative Examples 2 to 10 prepared using ref 1 to ref 9 compounds containing fluorene groups in the amine group were improved rather than the device of Comparative Example 1 manufactured using NPB mainly used as a hole transport layer material, and when the compound according to Formula (1) of the present invention is used as a hole transport layer material, the light emission efficiency and lifespan of the organic light emitting diode are increased, compared with Comparative Examples 2 to 10, and the driving voltage is slightly lowered, thereby improving the electrical characteristics of the device.

First, the ref 1 to ref 9 compound and the compound of the present invention approximately have a similar basic structure in which the amine group and the fluorene group in the chemical structure are included. However, based on the compounds of the present invention, ref 1 is different in that the amine group is connected to the naphthyl portion of benzonaphthofluorene, and ref 2 is an alkyl group which contains two amine groups and corresponds to Ar1 of the present invention (hereinafter referred to as Ar group), and differs in that only fused fluorene groups are included, and ref 3 and ref 4 are different in that only the fused fluorene group is substituted for the amine group, and the configurations corresponding to the unfused fluorene group of the present invention are biphenyl and dibenzothiophene (DBT), respectively, and ref 5 differs from the compound of the present invention in that a para-phenyl linking group is introduced between N and Ar groups of the amine group.

Also, ref 6 is similar to the compound of the present invention in that the fused diphenyl fluorene group and the unfused dimethyl fluorene group are substituted in the amine group, but differs in that a meta-phenyl linking group is introduced between N of the amine group and phenyl Ar group.

Finally, ref 7 to ref 9 are the same point that the ortho-phenyl linking group is introduced between N of the amine group and phenyl Ar group, but ref 7 differs in that both fluorene groups are fused fluorene groups, ref 8 differs in that the structure corresponding to the ring A of the present invention constituting the fused fluorene group is phenanthrene instead of $C_{10}$ aryl group (naphthyl), and ref 9 differs in that both fluorene groups are unfused fluorene groups.

First, looking at Comparative Example 3, it can be seen that the two amine groups are included, showing the most downward device characteristics in the device results of Comparative Examples 2 to 10. And, looking at Comparative Example 2, it can be seen that the N of the amine group is connected to the naphthyl ring corresponding to the A ring of the present invention, showing a lower device characteristics than the device results of Comparative Examples 4 to 10. It can be seen that the difference between the number of amine groups and the position at which the amine groups are substituted with the fused fluorene group affect the electrical properties of the device.

Also, in Comparative Examples 4 to 7, it can be seen that Comparative Examples 6 and 7 in which two fluorene groups are substituted in the amine group have improved characteristics of the device as a whole than the devices of Comparative Examples 4 and 5, and it can be seen that the fluorene group among the substituents substituted in the amine group has an energy level more suitable for the hole transport layer than the substituent (dibenzothiophene) containing the simple aryl (biphenyl) or hetero atom of Comparative Example 4.

It can be seen from Comparative Examples 8 to 10 that although they all are similar in that the amine group and Ar group have an ortho-phenyl linking group, Comparative Example 10 shows improved driving voltage compared with Comparative Example 8 and Comparative Example 9, and Comparative Examples 8 and 9 show improved efficiency compared to Comparative Example 10.

To summarize the device results of these Comparative Examples 2 to 10, in the structure containing one amine group and two fluorene groups, when N of the amine group is linked to the phenyl side of the fused fluorene group, and two fluorene groups are substituted with one fused fluorene group and one unfused fluorene group, and when A ring constituting the unfused fluorene group is naphthyl, and the ortho-linking group is introduced between the N and Ar groups of the amine group, it shows the best device performance.

Therefore, in the compound of the present invention represented by Formula (1), an ortho-phenyl group linking group is necessarily present between the amine group and Ar1, and thus it is confirmed that the device characteristics of Examples 1 to 17 are significantly improved compared to Comparative Examples 1 to 7.

TABLE 5

|  | Ref 6 | compound P-1 |
|---|---|---|
| LUMO (eV) | −1.266 | −1.183 |

Referring to Table 5, Comparing the physical properties of the compound P-1 represented by Formula (1) and the ref 6 compound having an Ar group linked to a amine group by a meta-phenyl group, although the skeleton is almost similar, it can be seen that Example Compound P-1 of the present invention has a relatively higher LUMO level than the ref 6 compound. This suggests that the physical properties of the compound vary markedly depending on the type and the degree of bending of the linking group, and in the case of the compound represented by Formula (1) of the present invention, since it has an appropriate LUMO level that can prevent electrons from falling in the emitting layer, it is determined that the device characteristics are remarkably improved compared to Comparative Example 7.

In addition, in the compound of the present invention represented by Formula (1), as the fused fluorene group represents dimethyl benzo fluorene, and the non-fused fluorene group represents diphenyl fluorene, it was confirmed that the device characteristics of Examples 1 to 17 are significantly improved than Comparative Examples 8 to 10.

TABLE 6

|  | ref 7 | ref 8 | ref 9 | compound P-4 |
|---|---|---|---|---|
| Molecular Weight | 653.87 | 778.01 | 691.92 | 727.95 |

Referring to Table 6, ref 7 to ref 9 compounds and compounds of the present invention is the same point that the fluorene group is substituted in the amine group, ortho-phenyl group linking group is introduced between the amine group and Ar1 group, and has a difference in the composition of carbon number and the presence/absence of fused fluorene group. That is, in Formula (1) of the present invention, the A ring is naphthyl of $C_{10}$, whereas there is a difference in that the ref 7 compound is both dimethyl benzofluorene in the fused fluorene group, the ref 8 compound is an aryl group of more than $C_{10}$, and the ref 9 compound is different from that of $C_6$ is phenyl, thus, in the molecular weight of Table 6, it can be confirmed that the compound P-4 of the present invention has a molecular weight of between values compared to the ref 7 to ref 9 compound molecular weight. For Comparative Example 9 in which compound denaturation occurs during the deposition process of a compound due to the Tg value that increases with increasing molecular weight and Comparative Example 8 and Comparative Example 10, which have a poor thermal stability by having a relatively low molecular weight, the compound of the present invention has a molecular weight value suitable for use in the hole transport layer, it can be seen that the difference in the results of the improved device.

Meanwhile, as can be seen from the device measurement results of the exemplary compounds of the present invention, it can be seen that the characteristics of the organic electric device is changed according to the fusion form of benzofluorene. More specifically, based on the following Formula F structure, the compounds containing the benzene-fused type at the 1st and 2nd positions in the amine group can be seen that the electrical properties are slightly improved than the compound having the benzene-fused type at the other position. Referring to following Table 7, it can be seen that compound P-1 having 1,2 fused fluorene has a higher LUMO energy level than compounds P-2 and P-3, from this, the physical properties of the compound vary depending on the fusion position of benzene, and high LUMO energy level values can prevent electrons from flowing through the emitting layer, which may lead to improvement of device results.

Reference Formula F

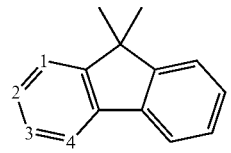

TABLE 7

|  | compound P-1 | compound P-2 | compound P-3 |
|---|---|---|---|
| LUMO (eV) | −1.183 | −1.314 | −1.300 |

Through the device results of the compounds of the present invention and the comparative compounds, the energy level of the compound (HOMO, LUMO and T, etc.) can be significantly changed depending on the position of the amine group and the fluorene group, the presence or absence of the linking group, the substitution type of the linking group, etc., this difference in compound properties suggests that different device results can be derived by acting as a major factor in improving device performance during device deposition. Furthermore, as in Formula of the present invention, a suitable structure for improving the performance of the device is that a fused fluorene is a dimethyl benzofluorene, an non-fused fluorene is a diphenyl fluorene, and the amine group and Ar1 have a structure in which the ortho-phenyl group linking group

[Example 18] Blue Organic Light Emitting Diode (Emitting-Auxiliary Layer)

After depositing 2-TNATA in a thickness of 60 nm on the ITO layer (anode) formed on the glass substrate to form a hole injection layer, NPB was vacuum-deposited on the hole injection layer to a thickness of 60 nm to form a hole transport layer.

Subsequently, the compound P-1 of the present invention was vacuum-deposited to a thickness of 20 nm on the hole transport layer to form an emitting-auxiliary layer, an emitting layer having a thickness of 30 nm was formed on the emitting-auxiliary layer by using 9,10-di(naphthalen-2-yl) anthracene as a host and BD-052X (manufactured by Idemitsu kosan) as a dopant in a weight ratio of 96:4.

Subsequently, BAlq was vacuum deposited to a thickness of 10 nm on the emitting layer to form a hole blocking layer, and Tris (8-quinolinol) aluminum (hereinafter abbreviated as Alq3) was vacuum deposited to a thickness of 40 nm on the hole blocking layer to form an electron transport layer.

Thereafter, LiF was deposited to a thickness of 0.2 nm to form an electron injection layer, and then, Al was deposited to a thickness of 150 nm to form an anode, thereby manufacturing an organic electroluminescent device.

[Example 19] to [Example 25] Blue Organic Light Emitting Diode (Emitting Auxiliary Layer)

An organic electroluminescent device was manufactured in the same manner as in Example 18, except that the compound of the present invention shown in Table 8 was used instead of the compound P-1 of the present invention as an emitting-auxiliary layer material.

Example 11

An organic electroluminescent device was manufactured in the same manner as in Example 1, except that the emitting-auxiliary layer was not formed.

[Example 12] to [Example 20]

An organic electroluminescent device was manufactured in the same manner as in Example 18, except for using one of ref 1 to ref 9 as an emitting-auxiliary layer material.

To the OLEDs which were manufactured by examples 18 to 25 and comparative example 20, a forward bias direct current voltage was applied, and electroluminescent (EL) properties were measured using PR-650 of Photoresearch Co., and T95 life was measured using a life measuring apparatus manufactured by McScience Inc. with a reference luminance of 500 d/m². In the following table 8, the manufacture of a device and the results of evaluation are shown.

TABLE 8

| | | | Current density | brightness | Efficiency | | CIE | |
|---|---|---|---|---|---|---|---|---|
| | compound | voltage | (mA/cm²) | (cd/m²) | (cd/A) | T(95) | x | |
| comparative example(11) | — | 5.7 | 14.3 | 500 | 3.5 | 52.4 | 0.132 | 0.100 |
| comparative example(12) | ref 1 | 5.6 | 11.9 | 500 | 4.2 | 70.2 | 0.130 | 0.100 |
| comparative example(13) | ref 2 | 5.6 | 12.8 | 500 | 3.9 | 68.3 | 0.130 | 0.100 |
| comparative example(14) | ref 3 | 5.5 | 11.1 | 500 | 4.5 | 73.5 | 0.131 | 0.100 |
| comparative example(15) | ref 4 | 5.5 | 10.4 | 500 | 4.8 | 76.6 | 0.132 | 0.100 |
| comparative example(16) | ref 5 | 5.4 | 10.9 | 500 | 4.6 | 80.7 | 0.131 | 0.100 |
| comparative example(17) | ref 6 | 5.3 | 10.2 | 500 | 4.9 | 90.0 | 0.131 | 0.100 |
| comparative example(18) | ref 7 | 5.3 | 9.8 | 500 | 5.1 | 88.4 | 0.131 | 0.100 |
| comparative example(19) | ref 8 | 5.3 | 9.6 | 500 | 5.2 | 87.3 | 0.132 | 0.100 |
| comparative example(20) | ref 9 | 5.2 | 10.2 | 500 | 4.9 | 85.1 | 0.131 | 0.100 |
| example(18) | P-1 | 4.6 | 5.9 | 500 | 8.5 | 113.8 | 0.130 | 0.100 |
| example(19) | P-2 | 4.6 | 6.8 | 500 | 7.3 | 111.2 | 0.132 | 0.100 |
| example(20) | P-3 | 4.6 | 6.3 | 500 | 7.9 | 112.3 | 0.130 | 0.100 |
| example(21) | P-12 | 4.7 | 7.5 | 500 | 6.7 | 110.5 | 0.132 | 0.100 |
| example(22) | P-30 | 4.7 | 7.1 | 500 | 7.0 | 109.7 | 0.132 | 0.100 |
| example(23) | P-31 | 4.8 | 7.8 | 500 | 6.4 | 108.8 | 0.130 | 0.100 |
| example(24) | P-38 | 5.0 | 8.8 | 500 | 5.7 | 105.4 | 0.130 | 0.100 |
| example(25) | P-52 | 4.9 | 8.2 | 500 | 6.1 | 107.9 | 0.131 | 0.100 |

As can be seen from the results of Table 8, the organic electroluminescent device using the compound of the present invention as a light emitting-auxiliary layer material is significantly improved the electrical characteristics of the device compared to the organic electroluminescent device of Comparative Examples 11 to 20.

These results can be seen that the characteristics of the device using the comparative compounds ref 1 to ref 9 and the compound of the present invention as the emitting-auxiliary layer is improved compared to the device without forming the emitting-auxiliary layer, and among them, it can be seen that the compound of the present invention shows an extremely high result in terms of lifespan.

It can be seen that the amine group and Ar1 have ortho-phenyl group substituents, and the characteristics of the fused fluorene group and the unfused fluorene group substituted in the amine group act as a major factor to improve the device performance in the emitting-auxiliary layer as well as the hole transport layer. As a result, it is judged that the efficiency is increased by improving the charge balance in the emitting layer, and as a result of preventing electrons from flowing from the emitting layer, the charge balance is maintained in the emitting layer, thereby improving driving voltage and lifetime.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

BRIEF DESCRIPTION OF THE DRAWINGS 100, 200, 300: organic electronic element
110: the first electrode
120: hole injection layer
130: hole transport layer
140: emitting layer
150: electron transport layer
160: electron injection layer
170: second electrode
180: light efficiency enhancing Layer
210: buffer layer
220: emitting-auxiliary layer
320: first hole injection layer
330: first hole transport layer
340: first emitting layer
350: first electron transport layer
360: first charge generation layer
361: second charge generation layer
420: second hole injection layer
430: second hole transport layer
440: second emitting layer
450: second electron transport layer
CGL: charge generation layer
ST1: first stack
ST1: second stack

What is claimed is:

1. A compound represented by Formula (1):

Formula (1)

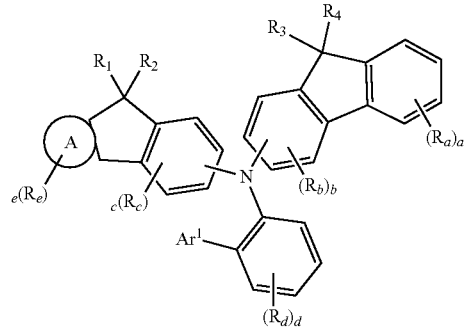

wherein:
1) $R_1$ and $R_2$ are each independently an unsubstituted $C_1$-$C_{60}$ alkyl group,
2) $R_3$ and $R_4$ are each independently an $C_6$-$C_{60}$ aryl group,
3) A is $C_{10}$ aryl group,
4) $Ar^1$ is a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring,
5) $R_a$, $R_b$, $R_c$, and $R_e$ are each independently selected from the group consisting of hydrogen; deuterium; halogen; a $C_6$-$C_{60}$ aryl group; a $C_6$-$C_{60}$ arylene group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring; and Rd is absent,
6) a is an integer of 0 to 4, b and c are each an integer of 0 to 3, e is an integer of 0 to 6, and d is 0 (zero),
wherein, the aryl group, arylene group, fluorenyl group, heterocyclic group, fused ring group, and aryloxy group may be substituted with one or more substituents selected from the group consisting of deuterium; cyano group; nitro group; $C_1$-$C_{20}$ alkyl group; $C_2$-$C_{20}$ alkenyl group; $C_6$-$C_{20}$ aryl group; $C_6$-$C_{20}$ aryl group substituted with deuterium; $C_6$-$C_{20}$ arylthiophene group; a fluorenyl group; and $C_2$-$C_{20}$ heterocyclic group.

2. The compound according to claim 1, wherein the compound represented by Formula (1) comprises a compound represented by any one of the following formulas A-1 to A-3:

Formula A-1

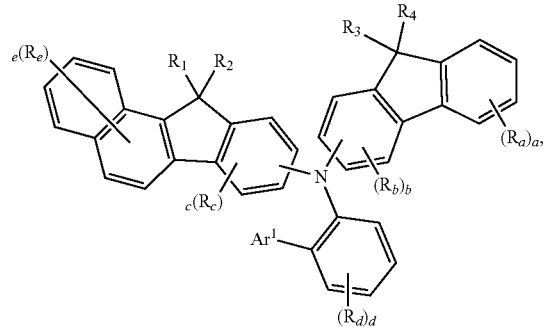

73
-continued

Formula A-2

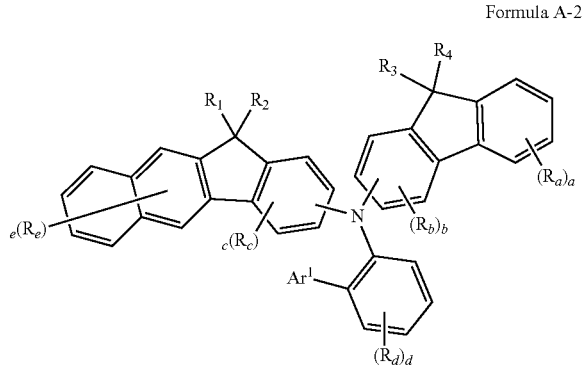

Formula A-3

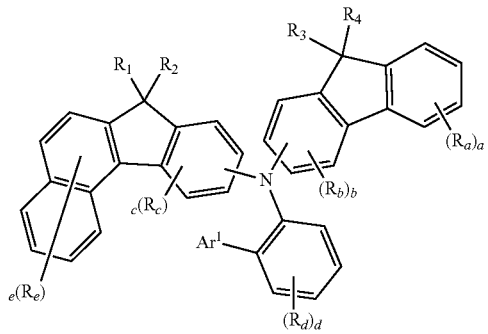

wherein $R_1$, $R_2$, $R_3$, $R_4$, $Ar^1$, $R_a$, $R_b$, $R_c$, $R_d$, $R_e$, a, b, c, d and e are the same as defined in claim 1.

3. The compound according to claim 1, wherein the compound represented by Formula (1) comprises a compound represented by any one of the following formulas B-1 to B-3:

Formula B-1

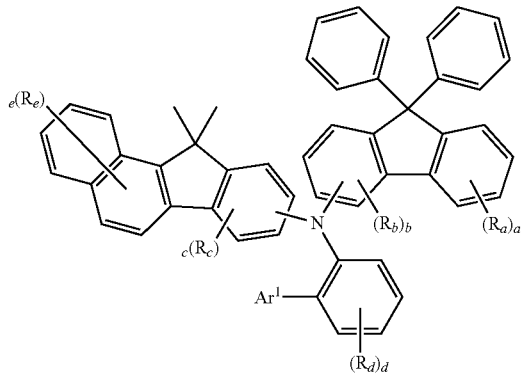

74
-continued

Formula B-2

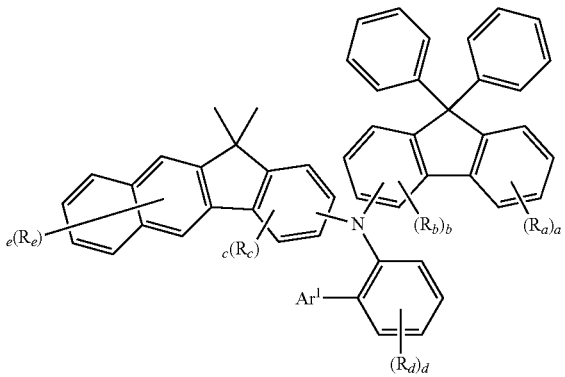

Formula B-3

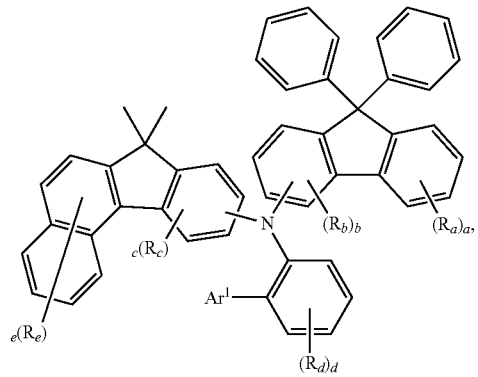

wherein $Ar^1$, $R_a$, $R_b$, $R_c$, $R_d$, $R_e$, a, b, c, d and e are the same as defined in claim 1.

4. The compound according to claim 1, wherein the compound represented by Formula (1) comprises a compound represented by Formula C:

Formula C

Formula C

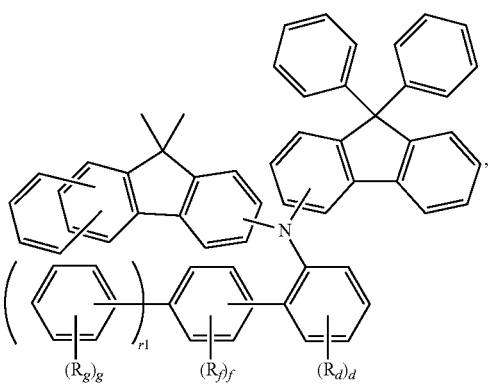

wherein:
1) $R_d$ is absent and d is 0 (zero) as defined in claim 1,
2) $R_f$ and $R_g$ are each independently selected from the group consisting of hydrogen; deuterium; halogen; a $C_6$-$C_{60}$ aryl group; a $C_6$-$C_{60}$ arylene group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

a $C_1$-$C_{60}$ alkyl group; a $C_2$-$C_{60}$ alkenyl group; a $C_2$-$C_{60}$ alkynyl group; a $C_1$-$C_{60}$ alkoxyl group; and a $C_6$-$C_{60}$ aryloxy group; or plurality of $R_f$ or plurality of $R_g$ or $R_f$ and $R_g$ may be bonded to each other to form ring, and 3) f is an integer of 0 to 4, g is an integer of 0 to 5, r1 is 0 or 1.

5. The compound according to claim 1, wherein the compound represented by Formula (1) comprises a compound represented by Formula D-1 or Formula D-2:

Formula D-1

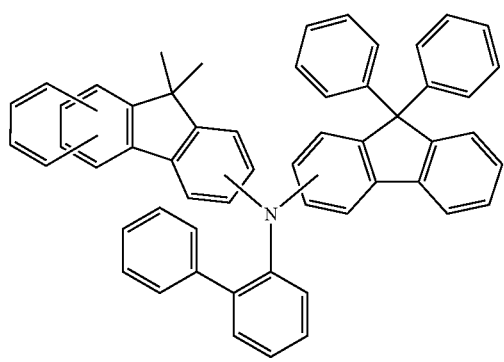

Formula D-2

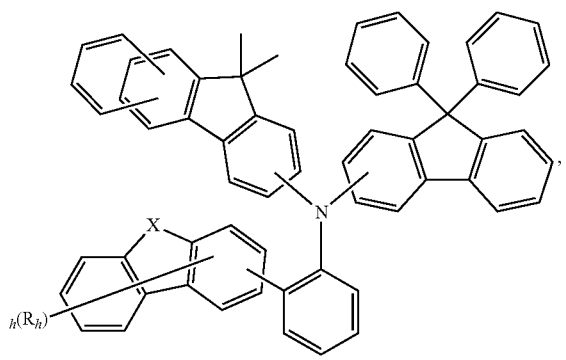

wherein:

$R_h$ is each independently selected from the group consisting of hydrogen; deuterium; halogen; a $C_6$-$C_{60}$ aryl group; a $C_6$-$C_{60}$ arylene group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxyl group; and a $C_6$-$C_{60}$ aryloxy group; or plurality of $R_h$ may be bonded to each other to form ring, h is an integer of 0 to 7, X is CR'R", O, S or N, R' and R" are each independently selected from the group consisting of hydrogen; a $C_6$-$C_{24}$ aryl group; a fluorenyl group; a $C_2$-$C_{24}$ heterocyclic group including at least one heteroatom of O, N, S, Si or P; a fused ring group of a $C_3$-$C_{24}$ aliphatic ring and a $C_6$-$C_{24}$ aromatic ring; a $C_1$-$C_{20}$ alkyl group; $C_2$-$C_{20}$ alkenyl group; $C_2$-$C_{20}$ alkynyl group; a $C_1$-$C_{20}$ alkoxyl group; and a $C_6$-$C_{30}$ aryloxy group; and R' and R" may be bonded to each other to form a spiro.

6. A compound selected from the group consisting of Formulas (P-1) to (P-52) below:

P-1

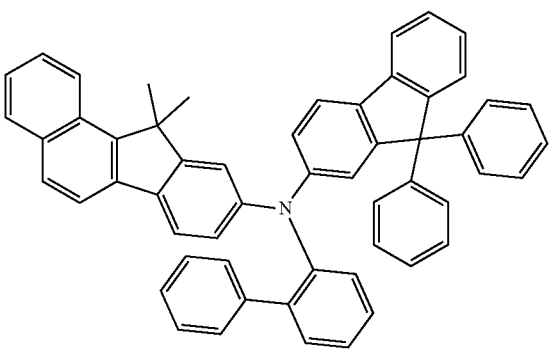

P-2

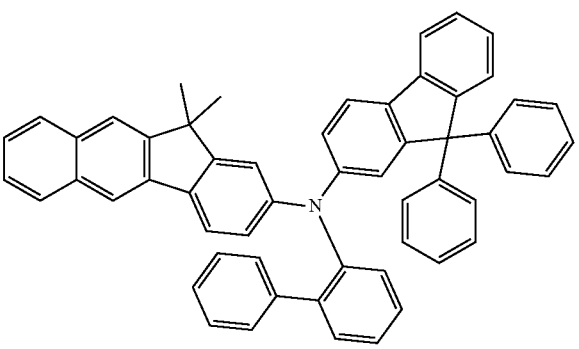

P-3

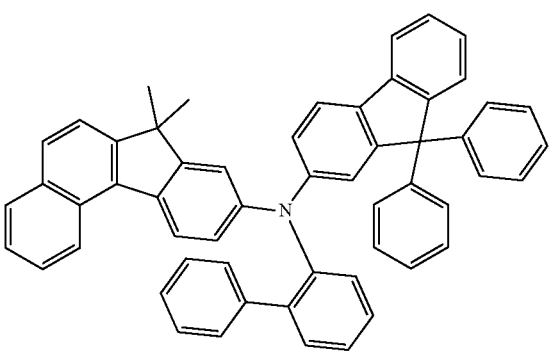

P-4

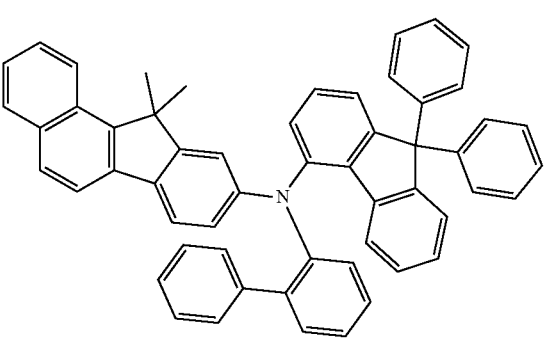

P-5
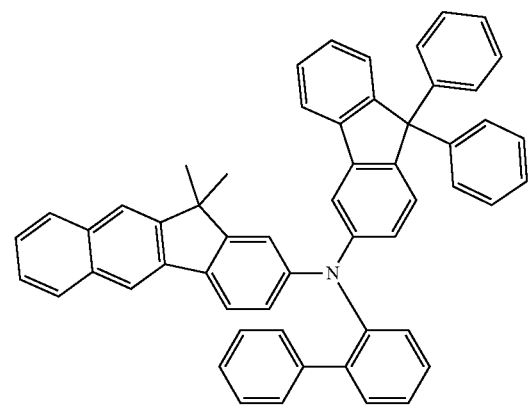
P-6
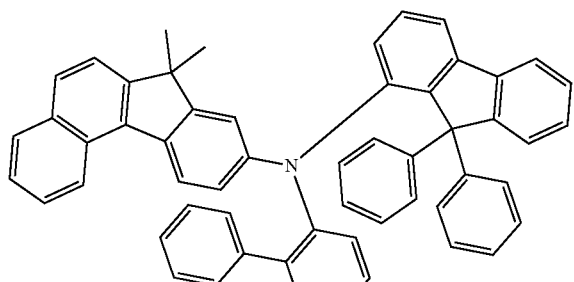
P-7
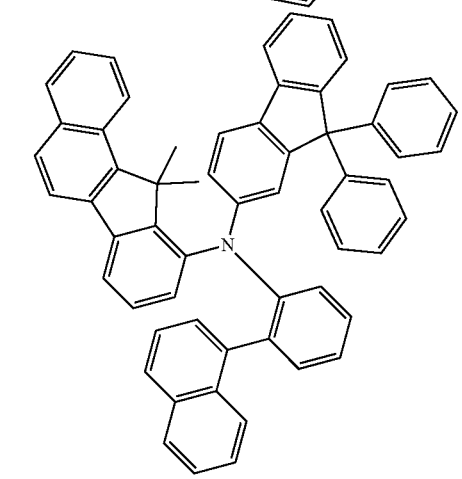
P-8
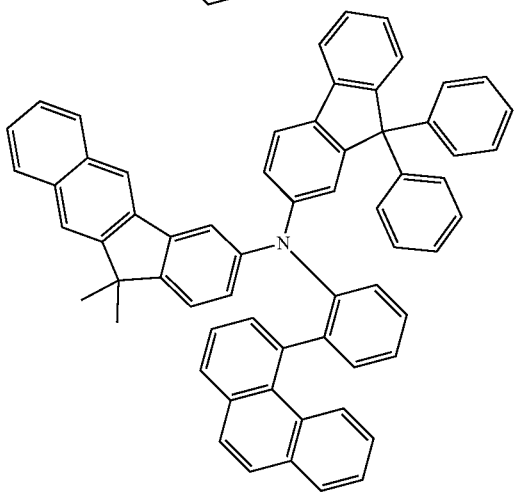
P-9
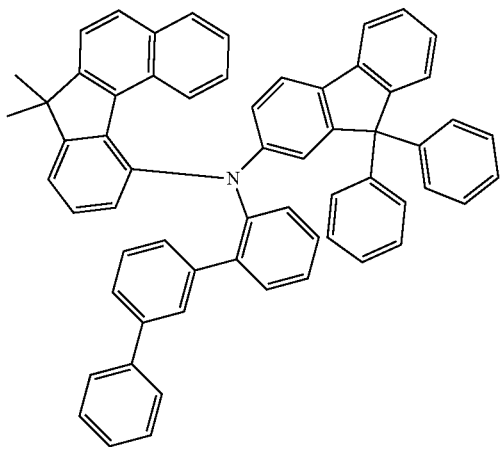
P-10
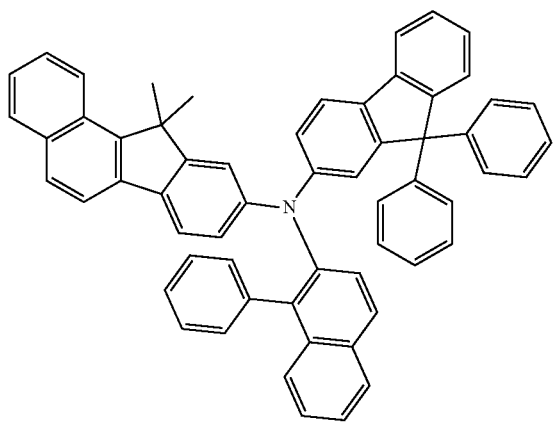
P-11
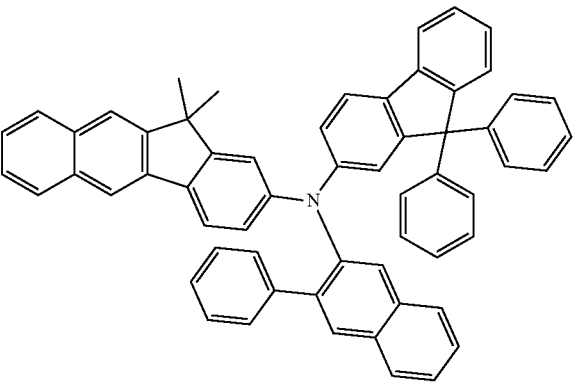

-continued
P-12
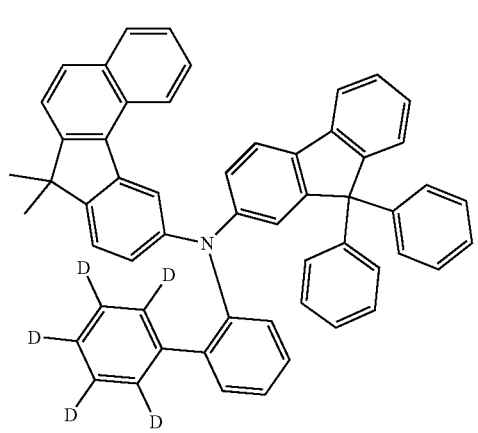
P-13
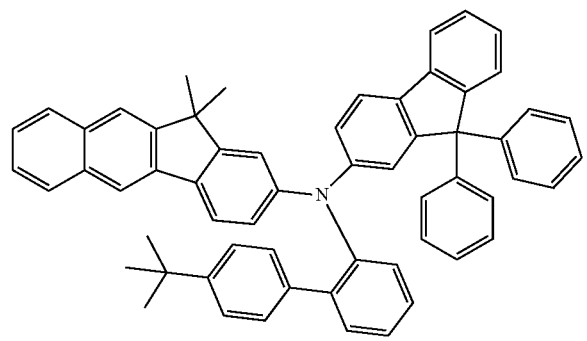
P-14
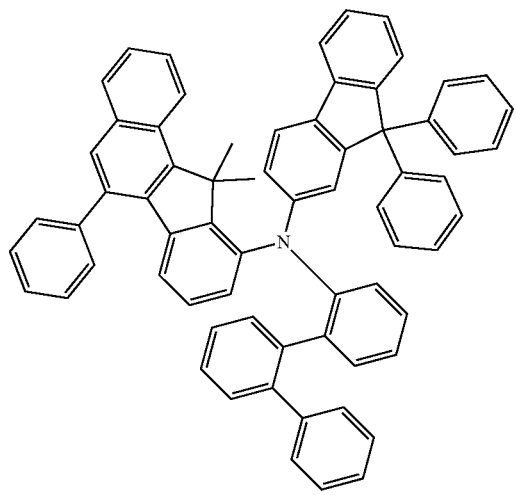
P-15
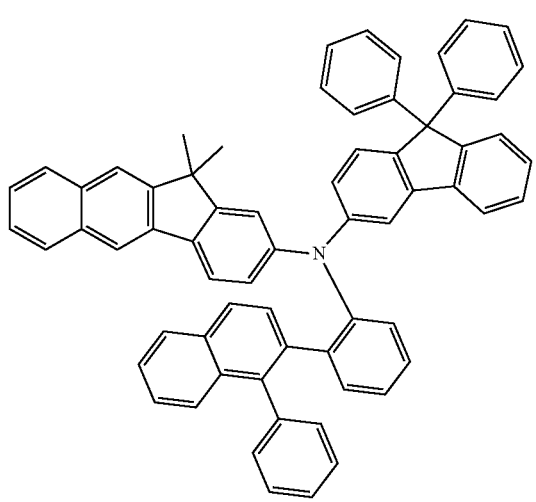
P-16
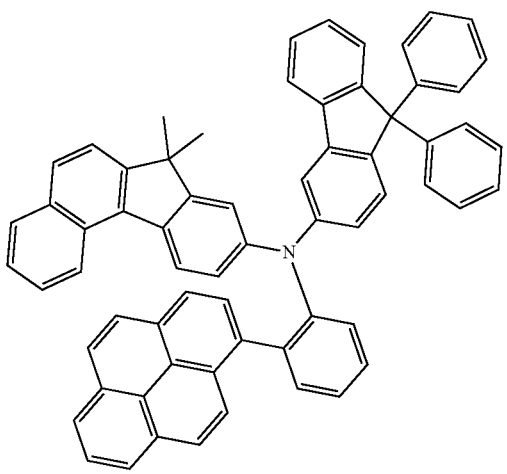
P-17
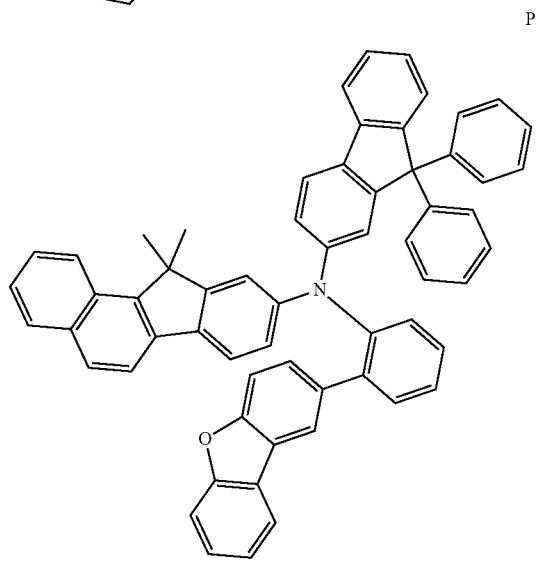

P-18
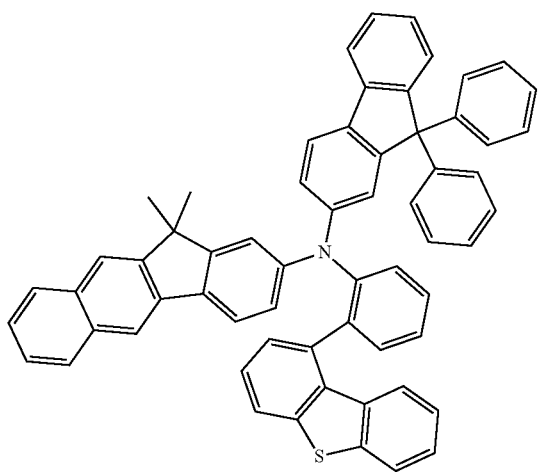
P-21
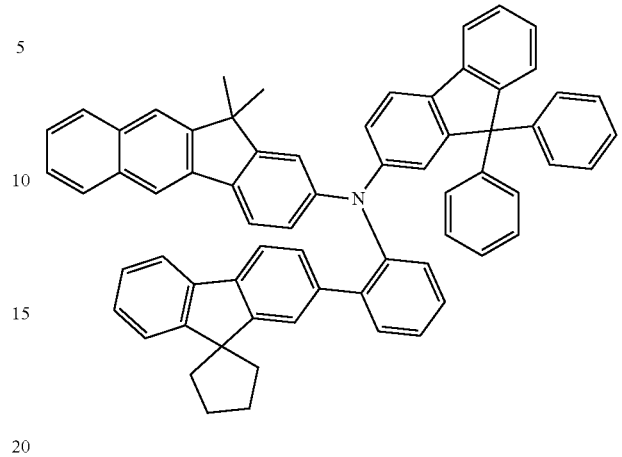
P-19
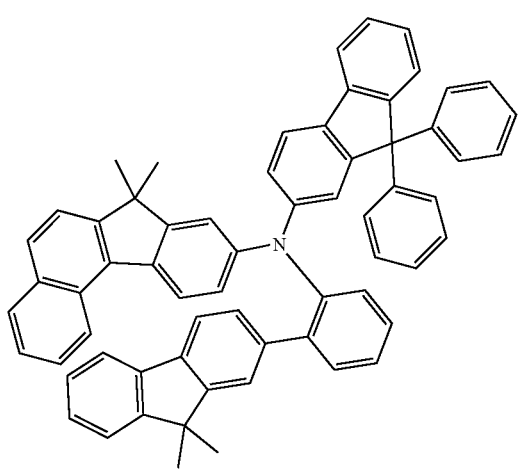
P-22
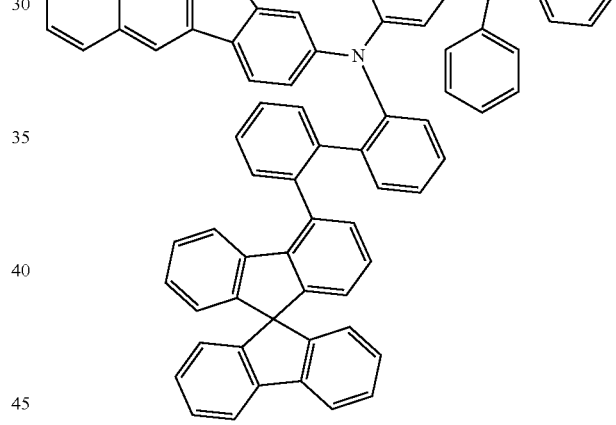
P-20
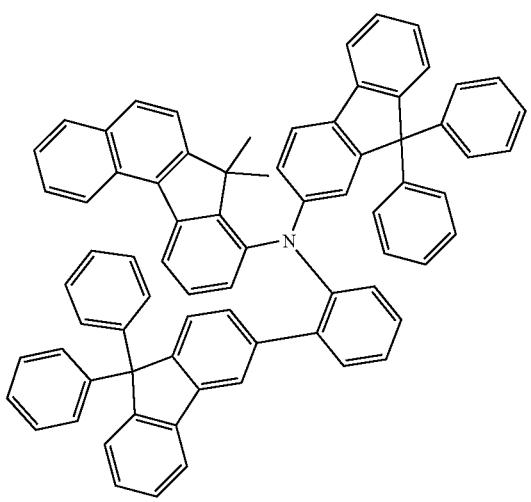
P-23
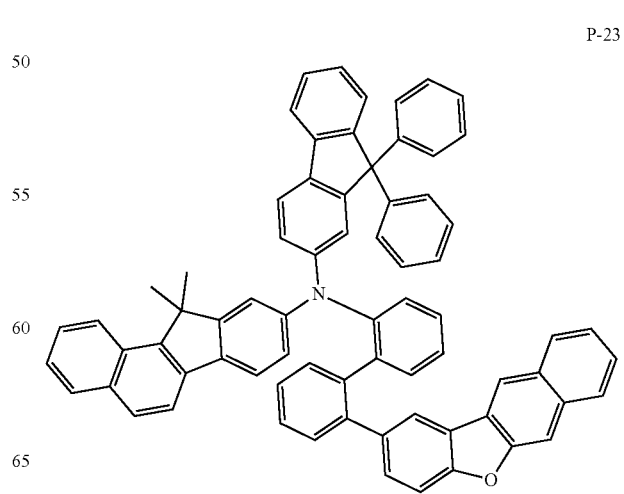

P-24
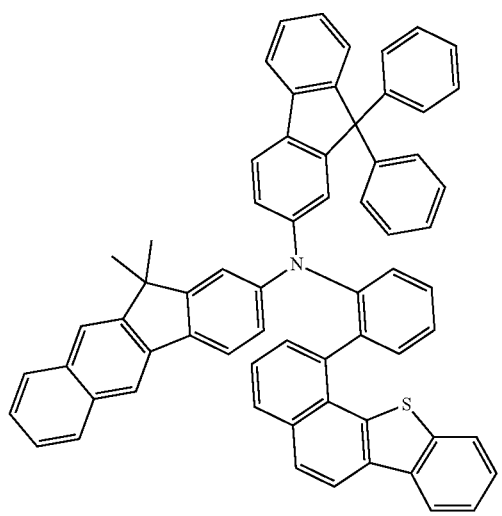
P-27
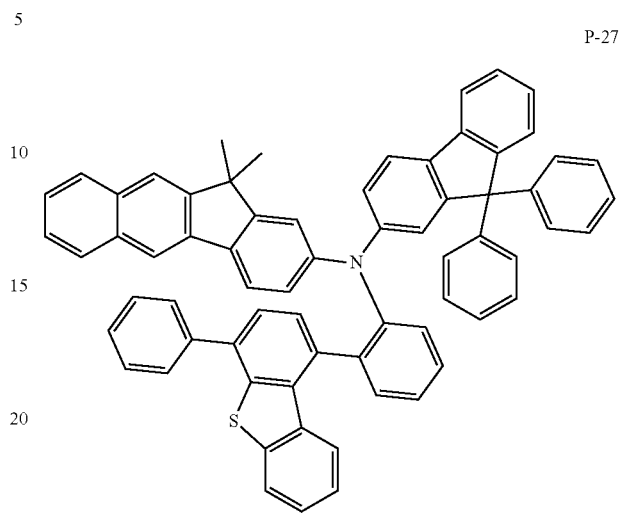
P-25
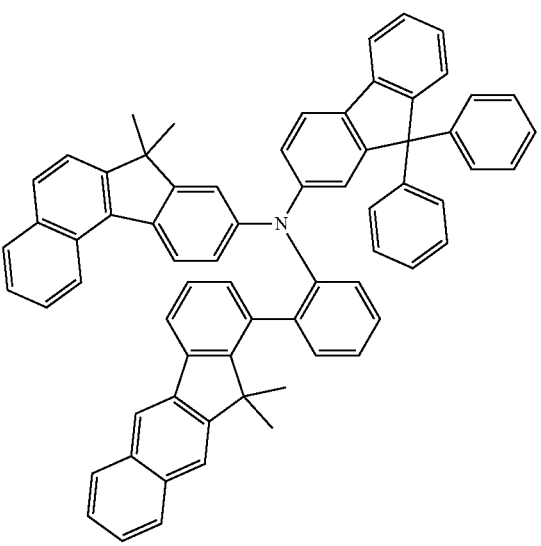
P-28
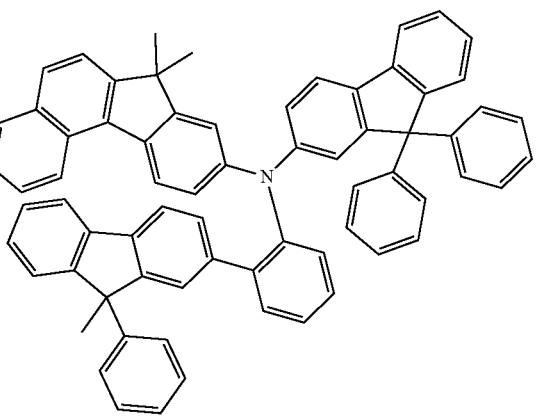
P-26
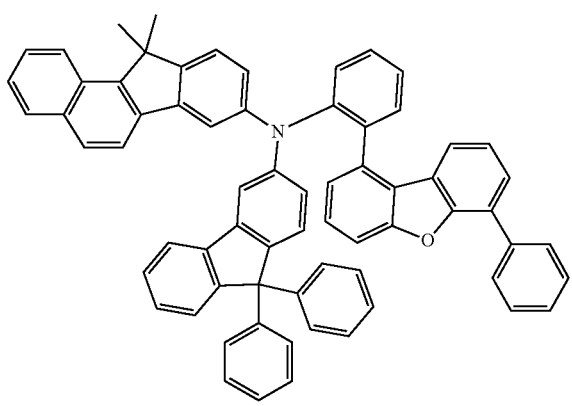
P-29
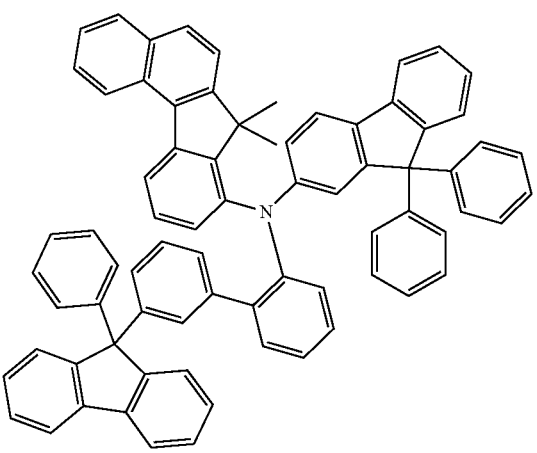

-continued
P-30
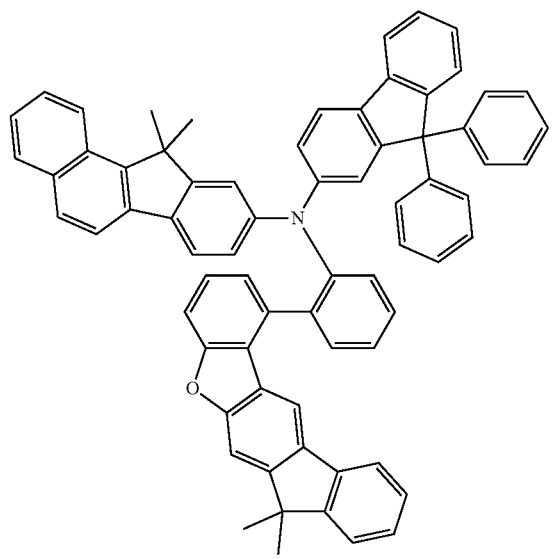
P-31
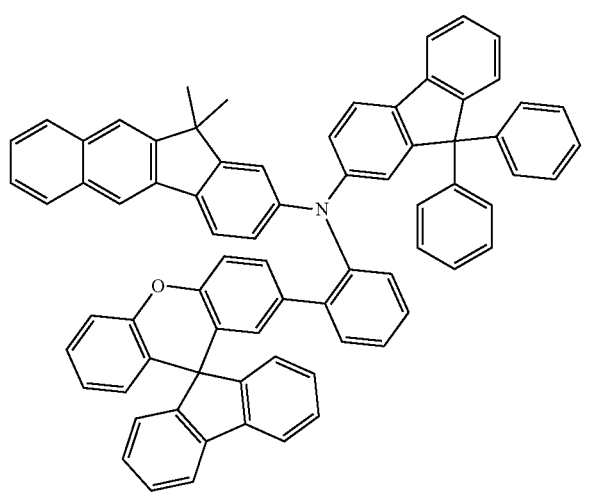
P-32
P-33
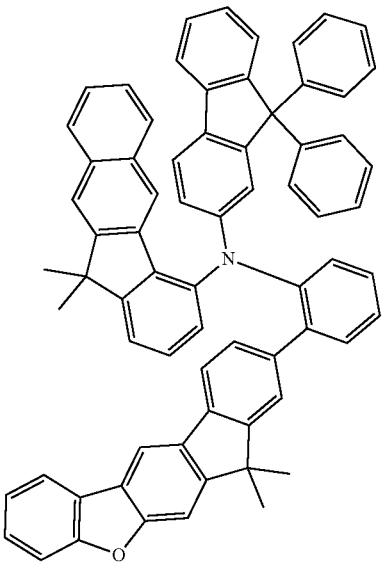
P-34
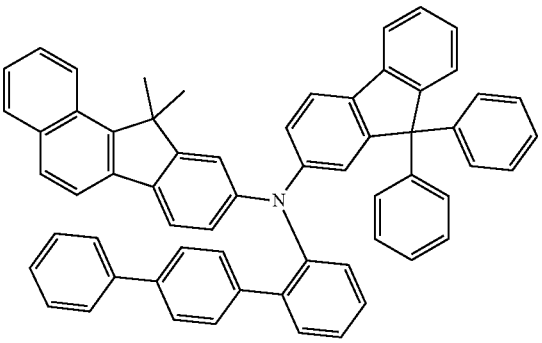
P-35
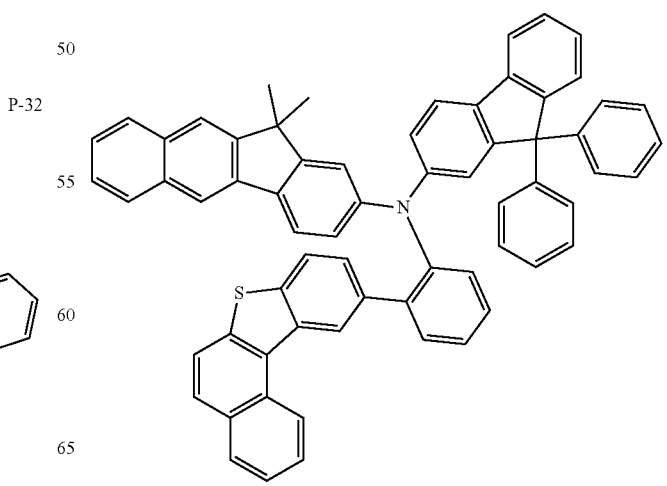

P-36
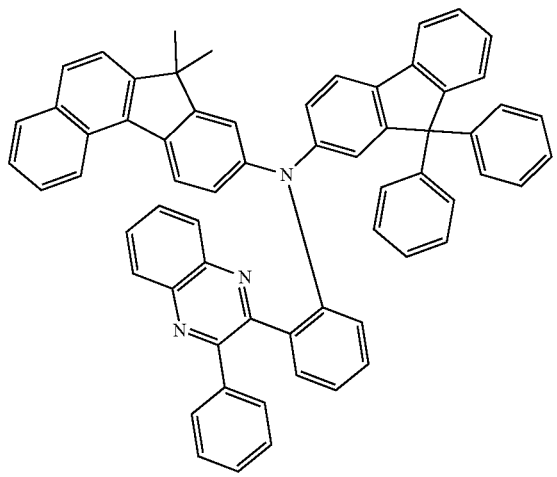
P-37
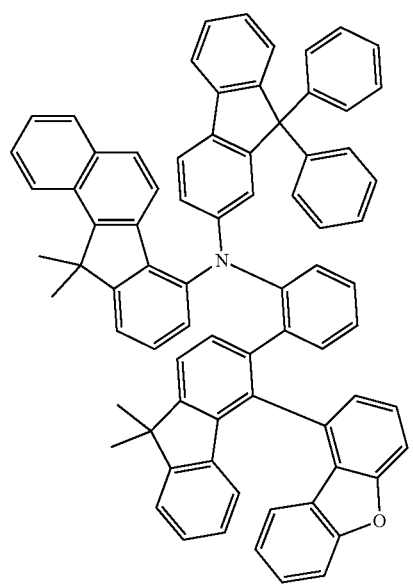
P-38
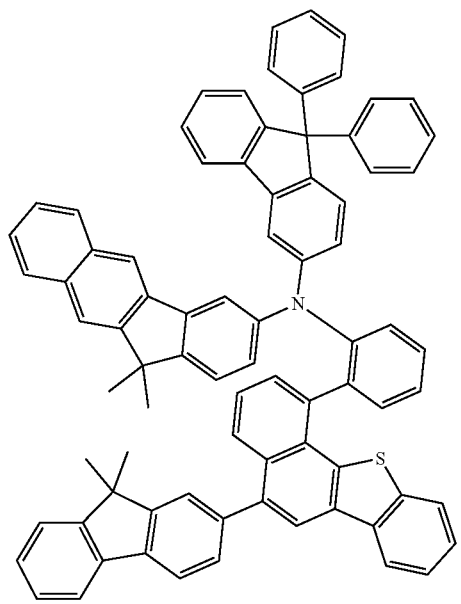
P-39
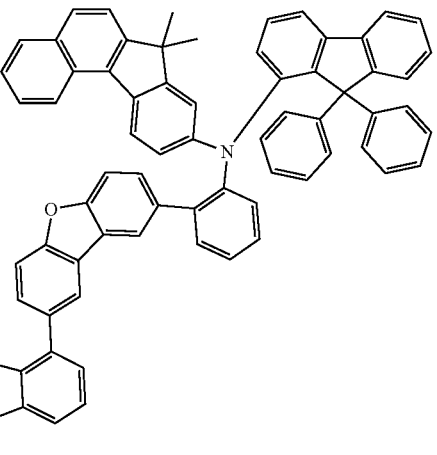
P-40
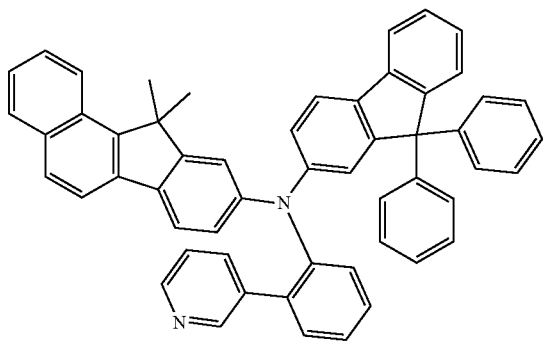
P-41
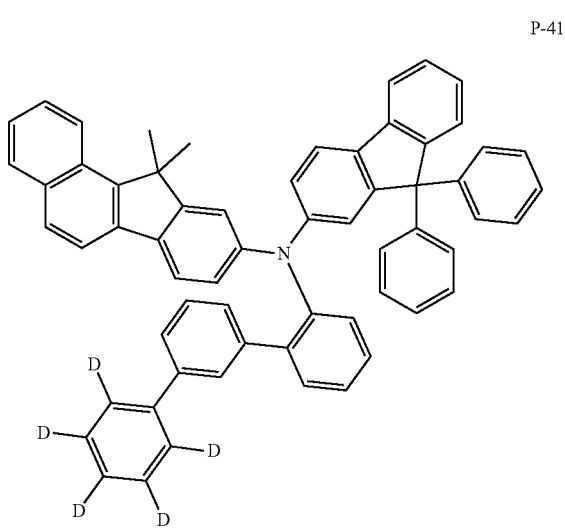

-continued
P-42
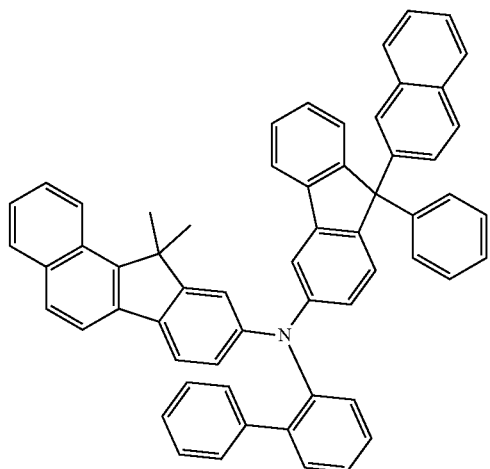
P-43
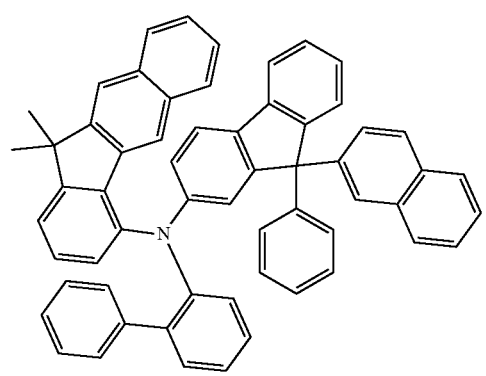
P-44
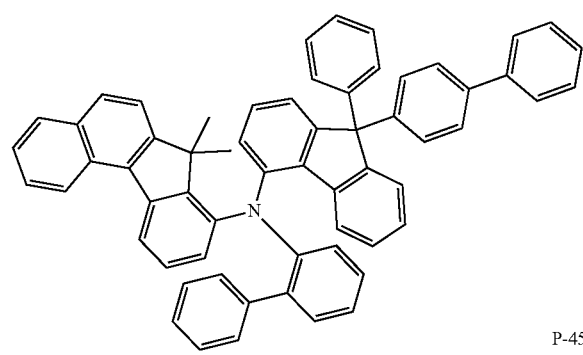
P-45
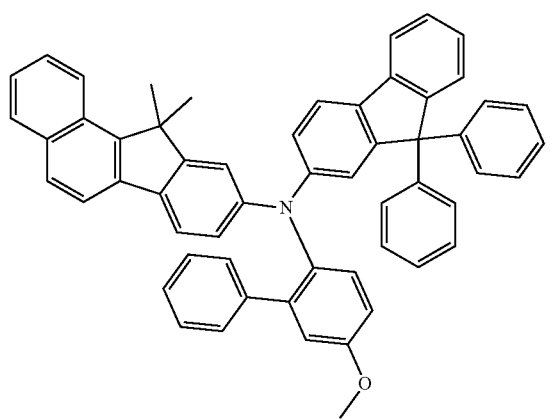
-continued
P-46
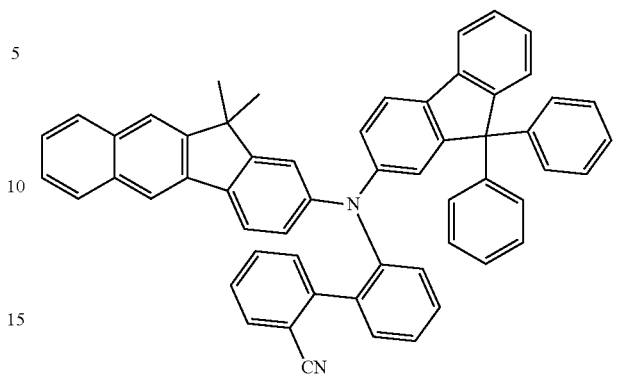
P-47
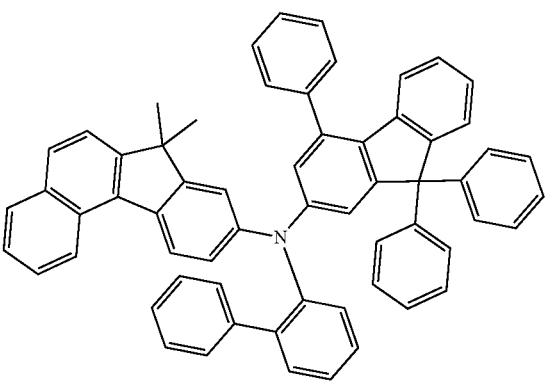
P-48
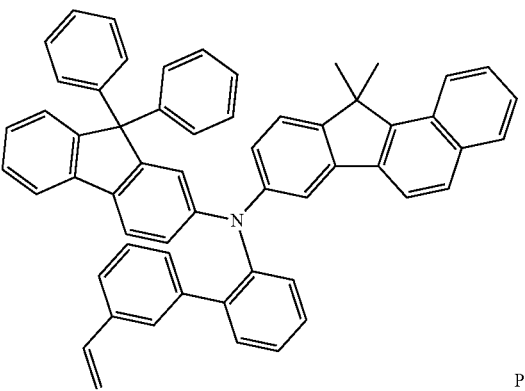
P-49
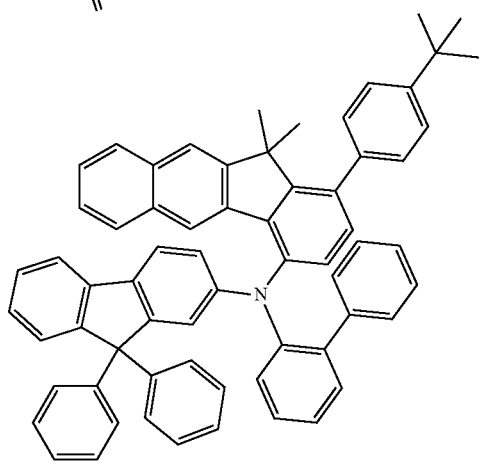

-continued

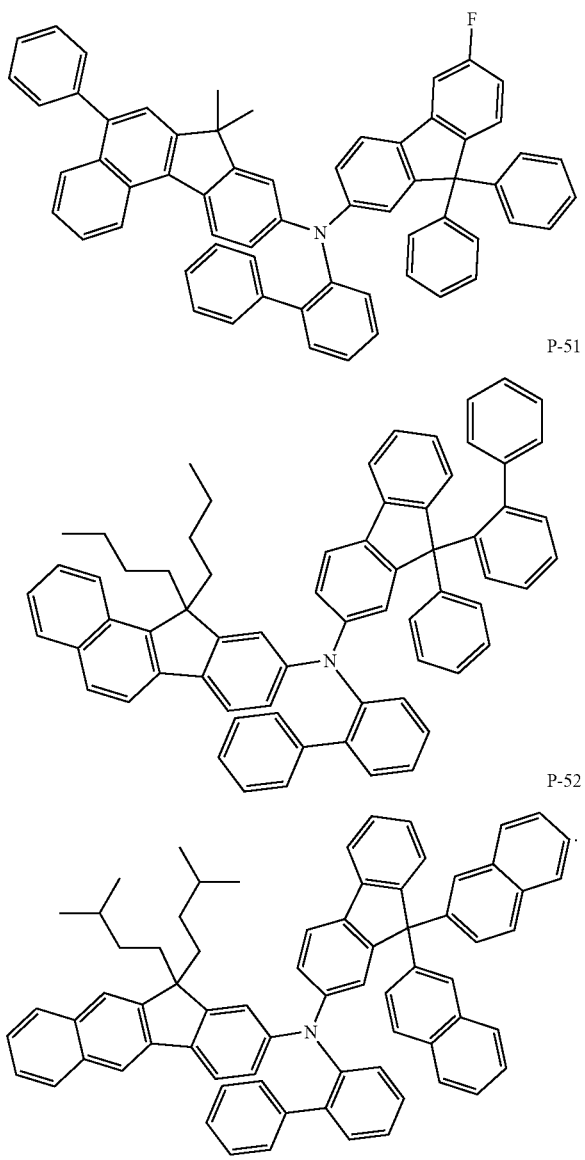

P-50

P-51

P-52

7. An organic electronic element comprising an anode, a cathode, and an organic material layer formed between the anode and the cathode, wherein the organic material layer comprises a single compound or two or more compounds represented by Formula (1) of claim 1.

8. The organic electronic element of claim 7, wherein the organic material layer comprises at least one of a hole injection layer, a hole transport layer, an emitting-auxiliary layer, an emitting layer, an electron transport auxiliary layer, an electron transport layer, and an electron injection layer.

9. The organic electronic element of claim 7, wherein the organic material layer is an emitting-auxiliary layer.

10. The organic electronic element of claim 7, further comprising a light efficiency enhancing layer formed on at least one surface of the anode and the cathode opposite to the organic material layer.

11. The organic electronic element of claim 7, wherein the organic material layer comprises two or more layers including a hole transport layer, an emitting layer, and an electron transport layer sequentially formed on the anode.

12. The organic electronic element of claim 11, wherein the organic material layer further comprises a charge generation layer formed between the two or more layers.

13. A display device comprising the organic electronic element of claim 7, and a control unit for driving the display device.

14. A display device according to claim 13, wherein the organic electronic element is at least one of an OLED, an organic solar cell, an organic photo conductor (OPC), organic transistor (organic TFT) and an element for monochromic or white illumination.

15. An organic electronic element comprising an anode, a cathode, and an organic material layer formed between the anode and the cathode, wherein the organic material layer comprises a single compound or two or more compounds of claim 6.

16. A display device comprising the organic electronic element of claim 15 and a control unit for driving the display device.

* * * * *